United States Patent
Akopian et al.

(10) Patent No.: US 9,925,251 B2
(45) Date of Patent: Mar. 27, 2018

(54) **TREATMENTS FOR *MYCOBACTERIUM TUBERCULOSIS***

(71) Applicant: PRESIDENT AND FELLOWS OF HARVARD COLLEGE, Cambridge, MA (US)

(72) Inventors: Tatos Akopian, West Roxbury, MA (US); Olga Kandror, Newton, MA (US); Alfred Lewis Goldberg, Brookline, MA (US); Ravikiran M. Raju, Cambridge, MA (US); Meera Unnikrishnan, Sienna (IT); Eric J. Rubin, Waban, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 143 days.

(21) Appl. No.: 14/352,440

(22) PCT Filed: Oct. 19, 2012

(86) PCT No.: PCT/US2012/061066
§ 371 (c)(1),
(2) Date: Apr. 17, 2014

(87) PCT Pub. No.: WO2013/059622
PCT Pub. Date: Apr. 25, 2013

(65) Prior Publication Data
US 2014/0243255 A1    Aug. 28, 2014

Related U.S. Application Data

(60) Provisional application No. 61/548,983, filed on Oct. 19, 2011, provisional application No. 61/588,421, filed on Jan. 19, 2012.

(51) Int. Cl.
| | | |
|---|---|---|
| *A61K 39/02* | (2006.01) | |
| *A01N 37/18* | (2006.01) | |
| *A61K 38/00* | (2006.01) | |
| *A61K 38/04* | (2006.01) | |
| *A61K 38/12* | (2006.01) | |
| *A61K 38/16* | (2006.01) | |
| *A61K 38/10* | (2006.01) | |
| *A61P 31/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *A61K 38/55* | (2006.01) | |
| *A61K 39/04* | (2006.01) | |
| *A61K 38/15* | (2006.01) | |
| *A61K 38/48* | (2006.01) | |
| *C07K 5/08* | (2006.01) | |
| *A61K 45/06* | (2006.01) | |
| *A61K 31/055* | (2006.01) | |
| *A61K 31/70* | (2006.01) | |
| *C12N 15/113* | (2010.01) | |
| *C12Q 1/37* | (2006.01) | |
| *C07K 5/097* | (2006.01) | |

(52) U.S. Cl.
CPC .......... *A61K 38/55* (2013.01); *A61K 31/055* (2013.01); *A61K 31/70* (2013.01); *A61K 38/04* (2013.01); *A61K 38/12* (2013.01); *A61K 38/15* (2013.01); *A61K 38/482* (2013.01); *A61K 39/04* (2013.01); *A61K 45/06* (2013.01); *C07K 5/08* (2013.01); *C12N 15/1137* (2013.01); *C12Q 1/37* (2013.01); *C12Y 304/21092* (2013.01); *C07K 5/0821* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 2002/0086843 A1 | 7/2002 | Sudoh et al. | |
| 2002/0106631 A1 | 8/2002 | Alnemri | |
| 2008/0038330 A1* | 2/2008 | Fleischer | A61K 9/127 424/450 |

FOREIGN PATENT DOCUMENTS

| | | |
|---|---|---|
| RU | 2357745 C1 | 6/2009 |
| RU | 2405834 C1 | 12/2010 |
| WO | 1999061003 | 12/1999 |

OTHER PUBLICATIONS

Akopian et al., EMBO J. 31:1529-1541 (2012).*
Johnston et al., PLoS ONE 4:1-9 (2009).*
Zhang, Annu. Rev. Pharmacol. Toxicol. 45:529-564 (2005).*
Caminero et al., Lancet Infect. Dis. 10:621-629 (Sep. 2010).*
Gavrish et al., "Novo23: a Novel Antibiotic with Specific Activity Against *Mycobacterium tuberculosis*," available online at http://www.icaaconline.com/php/icaac2013abstracts/data/papers/2012/F/2012_F-829.htm, Abstract F-829, 1 page (2012).*
Gavrish et al., Chem. Biol. 21:509-518 (2014).*
Chames et al., Brit. J. Pharmacol. 157:220-233 (2009).*
Sherrid et al., 5(7)1 (2010). "Characterization of a CLp protease gene regulator and the reaeration response in *Mycobacterium tuberculosis*.".
Bottcher, T., et al., ChemBioChem 10:663-666 (2009). "Structurally refined β-Lactones as potent inhibitors of devastating bacterial virulence factors.".
Brotz-Oesterhelt, H., et al., Nature Medicine 11(10):1082-1087 (2005). "Dysregualtion of bacterial proteolytic machinery by a new calss of antibiotics.".

(Continued)

*Primary Examiner* — James H Alstrum Acevedo
*Assistant Examiner* — Thea D'Ambrosio
(74) *Attorney, Agent, or Firm* — Nixon Peabody LLP; David S. Resnick; Nicole D. Kling

(57) ABSTRACT

The technology described herein relates to treatments for tuberculosis which target the ClpP1P2 protease complex, including ClpC1. Further embodiments relate to assays and screens for modulators of the ClpP1P2 protease complex, including ClpC1.

3 Claims, 22 Drawing Sheets

(56) References Cited

OTHER PUBLICATIONS

Kirstein, J., et al., EMBO Molecular Medicine 1:37-49 (2009). "The antibiotic ADEP reporgrammes CLPP, switching it from a regulated to an uncontrolled protease.".
Leung, E., et al., Chemistry & Biology 18(9,23):1167-1178 (2011). "Activators of cylindrical proteases as antimicrobials: identification and development of small molecule activators of CLPP protease.".
Schmitt, E.K., et al, Angewandte Chemie 123(26):6011-6013 (2011). "The natural product cyclomarin kills *Mycobacterium tuberculosis* by targeting the CLPC1 subunit of the caseinolytic protease.".

\* cited by examiner

5A Mtb ClpP1P2 has Inhibitor Specificity Characteristic of Serine Endopeptidases

| COMPOUND | % INHIBITION |
|---|---|
| 3,4-Dichloroisocoumarin (0.1 mM) | 100 |
| Z-Leu-Tyr-CMK (0.1 mM) | 78 |
| Ala-Ala-Phe-CMK (0.1 mM) | 68 |
| FP-Biotin* (0.1 mM) | 45 |
| PMSF (2 mM) | 15 |
| Leucine thiol (0.05 mM) | 5 |
| Bestatin (0.05 mM) | 3 |
| Iodine acetic acid (1 mM) | 0 |
| O-phenanthroline (0.25 mM) | 12 |
| EDTA (1mM) | 5 |

*10-(fluoroethoxyphosphynil)-N-(biotinamidopentyl)decanamide

5B Biotinylated Active-site Modifier (FP-Biotin) Binds to WT ClpP1 and ClpP2 Subunits but not to Active Site Mutants

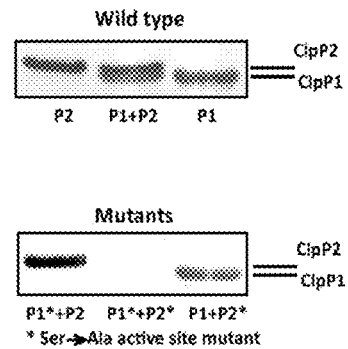

* Ser→Ala active site mutant

5C Inactivation of ClpP1 or ClpP2 Indicates that They Possess Different Substrate Preferences

| Effects of Inactivation of ClpP1 or ClpP2 on ClpP1P2 Function | | | | | |
|---|---|---|---|---|---|
| Enzyme | WT | P2 inactivated | | P1 inactivated | |
| ClpP1 | WT | WT | WT | DCI-treated | mutated |
| ClpP2 | WT | DCI-treated | mutated | WT | WT |
| Substrates | | Relative Activity (%) | | Relative Activity (%) | |
| Z-GGL-amc | 100 | 78 | 67 | 3 | 5 |
| Ac-nLPnLD-amc | 100 | 36 | 45 | 21 | 27 |
| FITC-casein | 100 | -- | 82 | -- | 38 |

Figures 5A-5C

```
Msm_ClpP1/1-215     1   VYQDVVESRYPVTDMRGTGGGINTVQDSTYERLLAERITFLGS      43
Mtb_ClpP1/1-200     1   ..........VSQVTDMRSNSQLSFTDSVYERLLSERILFLGS      34

Msm_ClpP1/1-215    44   QWDDDIANRCAQILFLSAEDPTKDIHLYINSPGGSISAGMAI       86
Mtb_ClpP1/1-200    35   EVNDEIANRLAQILFLAAEDASKDISIYINSPGGSISAGMAI       77

Msm_ClpP1/1-215    87   IDTMKVLAPCDIATYAMGMAASMGEFLLAAGTKGKRYALPHAR      129
Mtb_ClpP1/1-200    78   IDTMVLAPCDIATYAMGMAASMGEFLLAAGTKGKRYALPHAR      120

Msm_ClpP1/1-215   130   LMHQPLGGVTGSAADIAIQAEQFAVIKKEMFRLNAETTGQPIE      172
Mtb_ClpP1/1-200   121   LMHQFLGGVTGSAADIAIQAEQFAVIKKEMFRLNAETTGQPIE      163

Msm_ClpP1/1-215   173   RIEADSDRDRWFTAQEALEYGFVDHIITSASVNEGPGAGLDK     215
Mtb_ClpP1/1-200   164   RIEADSDRDRWMTAQEALEYGFHDHIITRAHVNGEAQ......     200

Msm_ClpP2/1-214     1   MSNIHPSLDARLQPDARYILPSFTEHSSFQVVESNPYNKLFEER      44
Mtb_ClpP2/1-218     1   ...VN.QNSQIQPDARYILPSFTEHSSFQVVESNPYNKLFEER      40

Msm_ClpP2/1-214    45   IFLGVQVDDASANDIMAQLIVESIDPDRDITMYINSPGGSFT      88
Mtb_ClpP2/1-218    41   IFFGVQVDDASANDIMAQLIVESIDPDRDITMYINSPGGSFT      84

Msm_ClpP2/1-214    89   SLMAIYDTMQYVKADIGTVGCGFSDIETQRAEIEMRTLAHLP     132
Mtb_ClpP2/1-218    85   SLMAIYDTMQYVKADIQTVGCQAASAAVILAAGTPGKRLALP     128

Msm_ClpP2/1-214   133   MARVTIHQPALSGVTGQFSLSSVIQQPSDLEQAEIERRLTAEFAKEYGTIDTVLQRHKLSAQTS   176
Mtb_ClpP2/1-218   129   MARVIHQPSLSSVIQQPSDLEQAEIERRLTAEFAKEYGTIDTVLQRKLSAQTA            172

Msm_ClpP2/1-214   177   GKDPAQ RKDTDRDKILTAEEAKEYGTIDTVLQRKLSAQTS     218
Mtb_ClpP2/1-218   173   GKDAGV TKDTDRDKILTAEEAKDIGTIDTVEPKLSAQTA     214
```

FIG. 7C

FIG. 8A
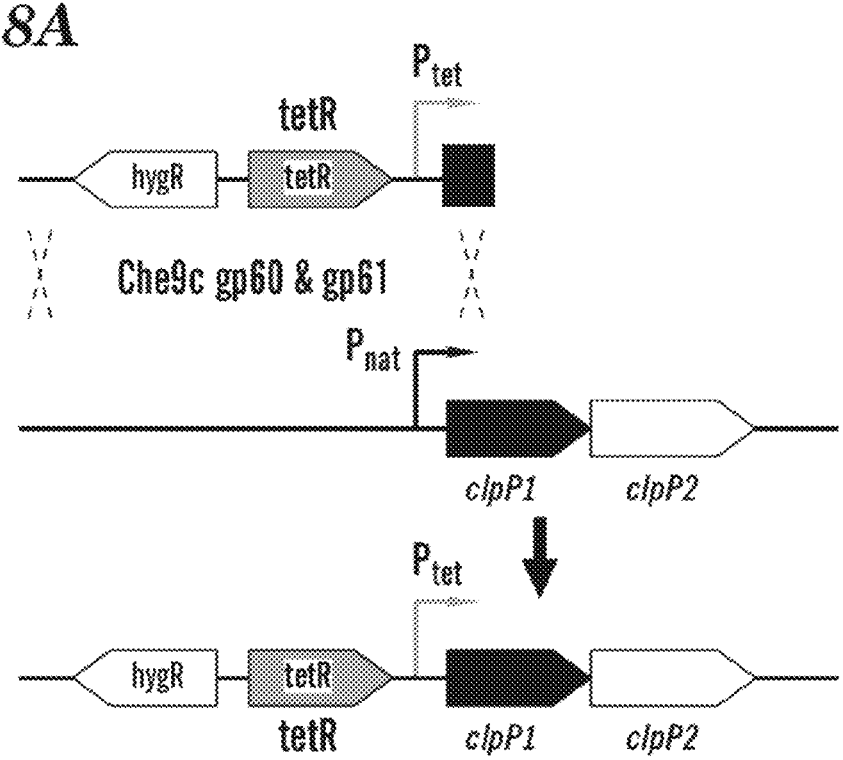
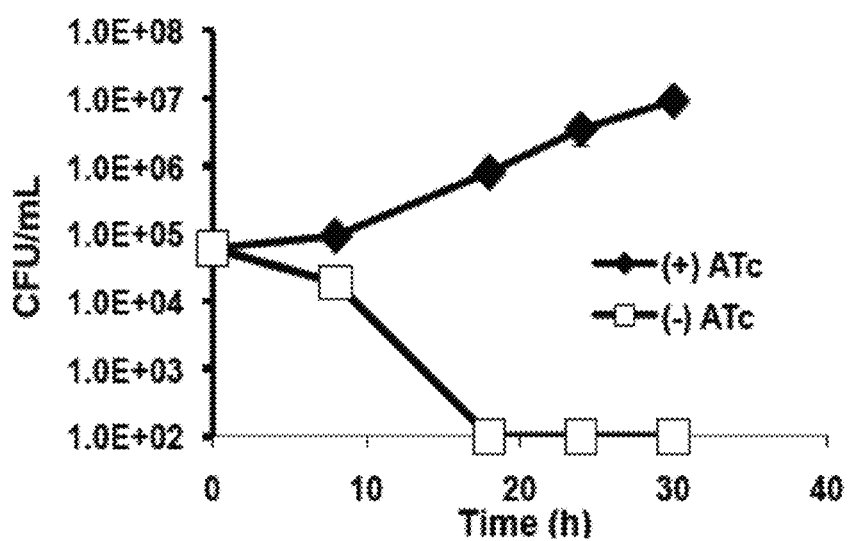
Fig. 8B

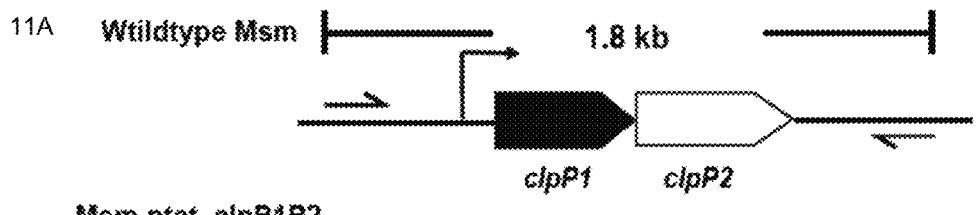
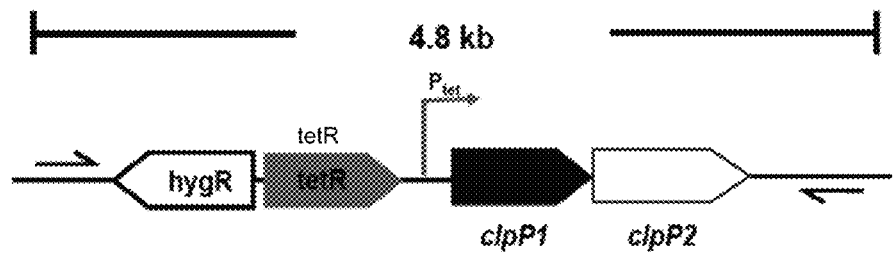
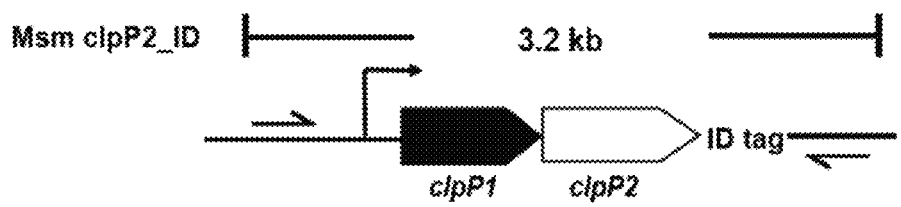
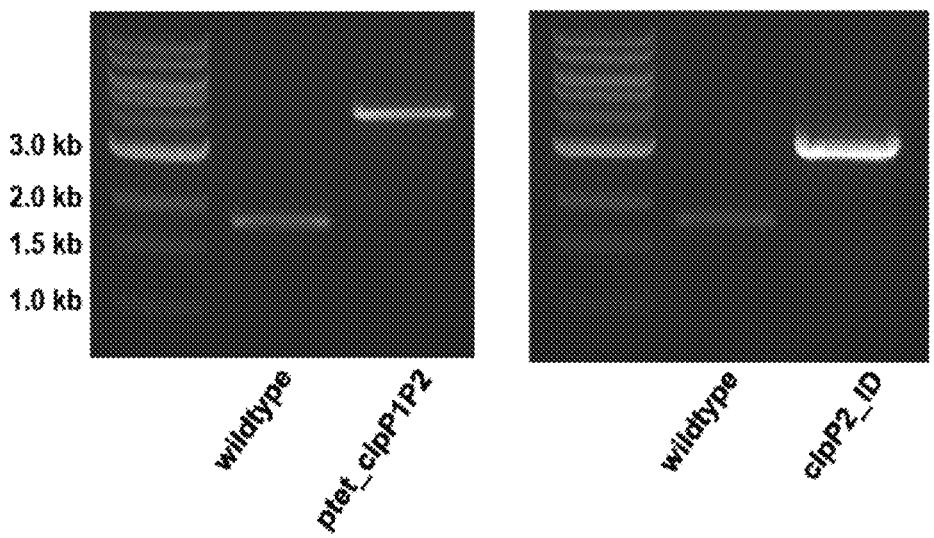
Figures 11A-11B

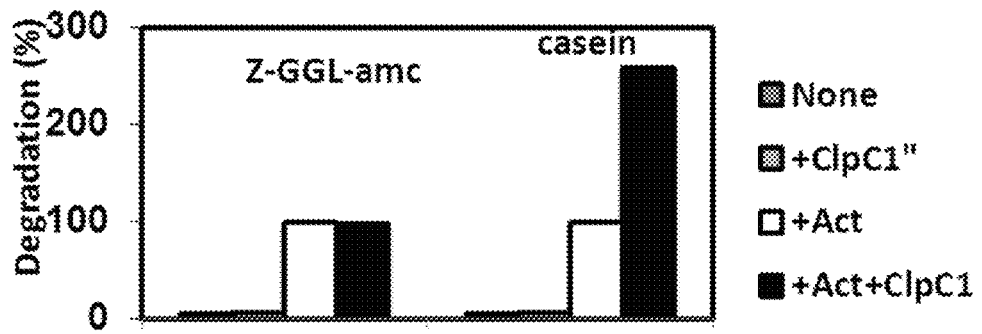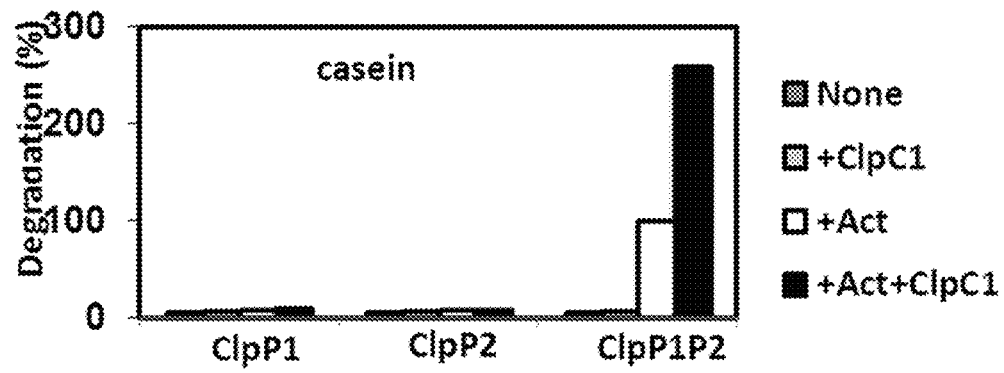
Figure 16

SEQUENCE LISTING

<160> NUMBER OF SEQ ID NOS: 37

<210> SEQ ID NO 1
<211> LENGTH: 200
<212> TYPE: PRT
<213> ORGANISM: Mycobacterium tuberculosis

<400> SEQUENCE: 1

Met Ser Gln Val Thr Asp Met Arg Ser Asn Ser Gln Gly Leu Ser Leu
1               5                   10                  15

Thr Asp Ser Val Tyr Glu Arg Leu Leu Ser Glu Arg Ile Ile Phe Leu
            20                  25                  30

Gly Ser Glu Val Asn Asp Glu Ile Ala Asn Arg Leu Cys Ala Gln Ile
        35                  40                  45

Leu Leu Leu Ala Ala Glu Asp Ala Ser Lys Asp Ile Ser Leu Tyr Ile
    50                  55                  60

Asn Ser Pro Gly Gly Ser Ile Ser Ala Gly Met Ala Ile Tyr Asp Thr
65                  70                  75                  80

Met Val Leu Ala Pro Cys Asp Ile Ala Thr Tyr Ala Met Gly Met Ala
                85                  90                  95

Ala Ser Met Gly Glu Phe Leu Leu Ala Ala Gly Thr Lys Gly Lys Arg
            100                 105                 110

Tyr Ala Leu Pro His Ala Arg Ile Leu Met His Gln Pro Leu Gly Gly
        115                 120                 125

Val Thr Gly Ser Ala Ala Asp Ile Ala Ile Gln Ala Glu Ala Phe Ala
    130                 135                 140

Val Ile Lys Lys Glu Met Phe Arg Leu Asn Ala Glu Phe Thr Gly Gln
145                 150                 155                 160

Pro Ile Glu Arg Ile Glu Ala Asp Ser Asp Arg Asp Arg Trp Phe Thr
                165                 170                 175

Ala Ala Glu Ala Leu Glu Tyr Gly Phe Val Asp His Ile Ile Thr Arg
            180                 185                 190

Ala His Val Asn Gly Glu Ala Gln
        195                 200

<210> SEQ ID NO 2
<211> LENGTH: 214
<212> TYPE: PRT
<213> ORGANISM: Mycobacterium tuberculosis

<400> SEQUENCE: 2

Met Asn Ser Gln Asn Ser Gln Ile Gln Pro Gln Ala Arg Tyr Ile Leu
1 5 10 15

Pro Ser Phe Ile Glu His Ser Ser Phe Gly Val Lys Glu Ser Asn Pro
20 25 30

Tyr Asn Lys Leu Phe Glu Glu Arg Ile Ile Phe Leu Gly Val Gln Val
35 40 45

Asp Asp Ala Ser Ala Asn Asp Ile Met Ala Gln Leu Leu Val Leu Glu
50 55 60

Ser Leu Asp Pro Asp Arg Asp Ile Thr Met Tyr Ile Asn Ser Pro Gly
65 70 75 80

Gly Gly Phe Thr Ser Leu Met Ala Ile Tyr Asp Thr Met Gln Tyr Val
85 90 95

Arg Ala Asp Ile Gln Thr Val Cys Leu Gly Gln Ala Ala Ser Ala Ala
100 105 110

Ala Val Leu Leu Ala Ala Gly Thr Pro Gly Lys Arg Met Ala Leu Pro

```
                 115                 120                 125
Asn Ala Arg Val Leu Ile His Gln Pro Ser Leu Ser Gly Val Ile Gln
            130                 135                 140
Gly Gln Phe Ser Asp Leu Glu Ile Gln Ala Ala Glu Ile Glu Arg Met
145                 150                 155                 160
Arg Thr Leu Met Glu Thr Thr Leu Ala Arg His Thr Gly Lys Asp Ala
                165                 170                 175
Gly Val Ile Arg Lys Asp Thr Asp Arg Asp Lys Ile Leu Thr Ala Glu
            180                 185                 190
Glu Ala Lys Asp Tyr Gly Ile Ile Asp Thr Val Leu Glu Tyr Arg Lys
        195                 200                 205
Leu Ser Ala Gln Thr Ala
    210

<210> SEQ ID NO 3
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Val Ser Gln Val Thr Asp Met Arg Ser Asn Ser Gln Gly Leu Ser Leu
1               5                   10                  15
Thr Asp Ser Val Tyr Glu Arg Leu Leu Ser Glu Arg Ile Ile Phe Leu
            20                  25                  30
Gly Ser Glu Val Asn Asp Glu Ile Ala Asn Arg Leu Cys Ala Gln Ile
        35                  40                  45
Leu Leu Leu Ala Ala Glu Asp Ala Ser Lys Asp Ile Ser Leu Tyr Ile
    50                  55                  60
Asn Ser Pro Gly Gly Ser Ile Ser Ala Gly Met Ala Ile Tyr Asp Thr
65                  70                  75                  80
Met Val Leu Ala Pro Cys Asp Ile Ala Thr Tyr Ala Met Gly Met Ala
                85                  90                  95
Ala Ser Met Gly Glu Phe Leu Leu Ala Ala Gly Thr Lys Gly Lys Arg
            100                 105                 110
Tyr Ala Leu Pro His Ala Arg Ile Leu Met His Gln Pro Leu Gly Gly
        115                 120                 125
Val Thr Gly Ser Ala Ala Asp Ile Ala Ile Gln Ala Glu Gln Phe Ala
    130                 135                 140
Val Ile Lys Lys Glu Met Phe Arg Leu Asn Ala Glu Phe Thr Gly Gln
145                 150                 155                 160
Pro Ile Glu Arg Ile Glu Ala Asp Ser Asp Arg Asp Arg Trp Phe Thr
                165                 170                 175
Ala Ala Glu Ala Leu Glu Tyr Gly Phe Val Asp His Ile Ile Thr Arg
            180                 185                 190
Ala His Val Asn Gly Glu Ala Gln
        195                 200

<210> SEQ ID NO 4
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 4

```
Val Tyr Gln Asp Val Val Glu Ser Arg Tyr Pro Val Val Thr Asp Met
1               5                   10                  15

Arg Gly Thr Gly Gln Gly Leu Asn Leu Val Asp Ser Val Tyr Glu Arg
            20                  25                  30

Leu Leu Ala Glu Arg Ile Ile Phe Leu Gly Ser Gln Val Asp Asp Asp
        35                  40                  45

Ile Ala Asn Arg Leu Cys Ala Gln Ile Leu Leu Ser Ala Glu Asp
50                  55                  60

Pro Thr Lys Asp Ile His Leu Tyr Ile Asn Ser Pro Gly Gly Ser Ile
65                  70                  75                  80

Ser Ala Gly Met Ala Ile Tyr Asp Thr Met Val Leu Ala Pro Cys Asp
                85                  90                  95

Ile Ala Thr Tyr Ala Met Gly Met Ala Ala Ser Met Gly Glu Phe Leu
            100                 105                 110

Leu Ala Ala Gly Thr Lys Gly Lys Arg Tyr Ala Leu Pro His Ala Arg
        115                 120                 125

Ile Leu Met His Gln Pro Leu Gly Gly Val Thr Gly Ser Ala Ala Asp
145                 150                 155                 160

Ile Ala Ile Gln Ala Glu Gln Phe Ala Val Ile Lys Lys Glu Met Phe
145                 150                 155                 160

Arg Leu Asn Ala Glu Phe Thr Gly Gln Pro Ile Glu Arg Ile Glu Ala
                165                 170                 175

Asp Ser Asp Arg Asp Arg Trp Phe Thr Ala Gln Glu Ala Leu Glu Tyr
            180                 185                 190

Gly Phe Val Asp His Ile Ile Thr Ser Ala Ser Val Asn Gly Glu Gly
        195                 200                 205

Pro Gly Ala Gly Leu Asp Lys
    210                 215
```

<210> SEQ ID NO 5
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Val Asn Ser Gln Asn Ser Gln Ile Gln Pro Gln Ala Arg Tyr Ile Leu
1               5                   10                  15

Pro Ser Phe Ile Glu His Ser Ser Phe Gly Val Lys Glu Ser Asn Pro
            20                  25                  30

Tyr Asn Lys Leu Phe Glu Glu Arg Ile Ile Phe Leu Gly Val Gln Val
        35                  40                  45

Asp Asp Ala Ser Ala Asn Asp Ile Met Ala Gln Leu Leu Val Leu Glu
50                  55                  60

Ser Leu Asp Pro Asp Arg Asp Ile Thr Met Tyr Ile Asn Ser Pro Gly
65                  70                  75                  80

Gly Gly Phe Thr Ser Leu Met Ala Ile Tyr Asp Thr Met Gln Tyr Val
                85                  90                  95

Arg Ala Asp Ile Gln Thr Val Cys Leu Gly Gln Ala Ala Ser Ala Ala
            100                 105                 110

Ala Val Leu Leu Ala Ala Gly Thr Pro Gly Lys Arg Met Ala Leu Pro
        115                 120                 125
```

```
Asn Ala Arg Val Leu Ile His Gln Pro Ser Leu Ser Gly Val Ile Gln
130                 135                 140

Gly Gln Phe Ser Asp Leu Glu Ile Gln Ala Ala Glu Ile Glu Arg Met
145                 150                 155                 160

Arg Thr Leu Met Glu Thr Thr Leu Ala Arg His Thr Gly Lys Asp Ala
                165                 170                 175

Gly Val Ile Arg Lys Asp Thr Asp Arg Asp Lys Ile Leu Thr Ala Glu
                180                 185                 190

Glu Ala Lys Asp Tyr Gly Ile Ile Asp Thr Val Leu Glu Tyr Arg Lys
                195                 200                 205

Leu Ser Ala Gln Thr Ala
        210
```

<210> SEQ ID NO 6
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Met Ser Asn Ile His Pro Ser Leu Asp Ala Arg Leu Gln Pro Gln Ala
1               5                   10                  15

Arg Tyr Ile Leu Pro Ser Phe Ile Glu His Ser Phe Gly Val Lys
                20                  25                  30

Glu Ser Asn Pro Tyr Asn Lys Leu Phe Glu Glu Arg Ile Ile Phe Leu
                35                  40                  45

Gly Val Gln Val Asp Asp Ala Ser Ala Asn Asp Ile Met Ala Gln Leu
            50                  55                  60

Leu Val Leu Glu Ser Leu Asp Pro Asp Arg Asp Ile Thr Met Tyr Ile
65                  70                  75                  80

Asn Ser Pro Gly Gly Ser Phe Thr Ser Leu Met Ala Ile Tyr Asp Thr
                85                  90                  95

Met Gln Tyr Val Arg Ala Asp Ile Gln Thr Val Cys Leu Gly Gln Ala
                100                 105                 110

Ala Ser Ala Ala Ala Val Leu Leu Ala Ala Gly Thr Pro Gly Lys Arg
                115                 120                 125

Leu Ala Leu Pro Asn Ala Arg Val Leu Ile His Gln Pro Ala Leu Ser
            130                 135                 140

Gly Val Ile Gln Gly Gln Phe Ser Asp Leu Glu Ile Gln Ala Ala Glu
145                 150                 155                 160

Ile Glu Arg Met Arg Thr Leu Met Glu Thr Thr Leu Ala Arg His Thr
                165                 170                 175

Gly Lys Asp Pro Ala Gln Ile Arg Lys Asp Thr Asp Arg Asp Lys Ile
                180                 185                 190

Leu Thr Ala Glu Glu Ala Lys Glu Tyr Gly Ile Ile Asp Thr Val Leu
                195                 200                 205

Gln Tyr Arg Lys Leu Ser Ala Gln Thr Ser
            210                 215
```

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
gcactgttaa ttaagaagga gatataccta tgcgttcgaa ctcgcag      47

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agtatacagc tgtcactgtg cttctccatt gacctg      36

<210> SEQ ID NO 9
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcactgttaa ttaagaagga gatataccta tgcgctacat cctgccgtc      49

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agtatacagc tgtcaggcgg tttgcgcgga      30

<210> SEQ ID NO 11
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agtatacagc tgtcacaggt cctcctccga gatcagcttc tgctcctgtg cttctccatt      60
gacctg      66

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agtatacagc tggtggtggt ggtggtggtg ctgtgcttct ccattgacct g      51

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic

```
          primer

<400> SEQUENCE: 13
agtatacagc tgtcacaggt cctcctccga gatcagcttc tgctcggcgg tttgcgcgga    60

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agtatacagc tggtggtggt ggtggtggtg ggcggtttgc gcgga                    45

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gatccgcatg cttaattaag aaggag                                         26

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtggtggtga tggatggtgt ttgtatagtt catccatgcc atg                      43

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctgatgtgaa tcggcgtggt ggtgatgatg gtgtttctat ag                       42

<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cggaatatcg atctaggcag cgagagcgta gtcgcgctga tgtgaatcgg c              51

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 19
ccgccgtggc ctgaccatc                                                        19

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcttccgccg acagcaacag g                                                     21

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
catccagggc cagttctc                                                         18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgtggtgttt gccgttct                                                         18

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcacggcata catcatttcg acgccg                                                26

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggcggtttgc gcggagagc                                                        19

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Mca-Lys
<220> FEATURE:
<221> NAME/KEY: MOD_RES
<222> LOCATION: (10)..(10)
<223> OTHER INFORMATION: Dpa(Dnp)-amide

<400> SEQUENCE: 25

Lys Lys Pro Thr Pro Ile Gln Leu Asn Xaa
1               5                   10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 26

His His His His His His
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Mca-Gly
<220> FEATURE:
<221> NAME/KEY: MOD_RES
<222> LOCATION: (9)..(9)
<223> OTHER INFORMATION: Dpa(Dnp)-amide

<400> SEQUENCE: 27

Gly Asn Thr Gln Phe Lys Arg Arg Xaa
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Mca-Gly
<220> FEATURE:
<221> NAME/KEY: MOD_RES
<222> LOCATION: (9)..(9)
<223> OTHER INFORMATION: Dpa(Dnp)-amide

<400> SEQUENCE: 28

Gly His Gln Gln Tyr Ala Met Lys Xaa
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Mca-Gly
<220> FEATURE:
<221> NAME/KEY: MOD_RES
<222> LOCATION: (9)..(9)
<223> OTHER INFORMATION: Dpa(Dnp)-amide

<400> SEQUENCE: 29

Gly Asn Gln Gln Tyr Lys Met Lys Xaa
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Mca-Lys
<220> FEATURE:
<221> NAME/KEY: MOD_RES
<222> LOCATION: (10)..(10)
<223> OTHER INFORMATION: Dpa(Dnp)-amide

<400> SEQUENCE: 30

Lys Lys Pro Thr Pro Ile Gln Leu Asn Xaa
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Mca-Gly
<220> FEATURE:
<221> NAME/KEY: MOD_RES
<222> LOCATION: (9)..(9)
<223> OTHER INFORMATION: Dpa(Dnp)-amide

<400> SEQUENCE: 31

Gly His Gln Gln Tyr Lys Met Lys Xaa
1               5

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Suc-Leu
<220> FEATURE:
<221> NAME/KEY: MOD_RES
<222> LOCATION: (4)..(4)
<223> OTHER INFORMATION: Tyr-amc

<400> SEQUENCE: 32

Leu Leu Val Tyr
1
```

```
<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Suc-Ala
<220> FEATURE:
<221> NAME/KEY: MOD_RES
<222> LOCATION: (4)..(4)
<223> OTHER INFORMATION: Phe-amc

<400> SEQUENCE: 33

Ala Leu Pro Phe
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Suc-Ala
<220> FEATURE:
<221> NAME/KEY: MOD_RES
<222> LOCATION: (4)..(4)
<223> OTHER INFORMATION: Ala-amc

<400> SEQUENCE: 34

Ala Ala Pro Ala
1

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Ala Asp Ser His Gln Arg Asp Tyr Gly Leu Ala Ala Pro Gln Phe
1               5                   10                  15

Ser

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Leu Ala Ala
1

<210> SEQ ID NO 37
<211> LENGTH: 848
<212> TYPE: PRT
```

-continued

<213> ORGANISM: Mycobacterium tuberculosis

<400> SEQUENCE: 37

```
Met Phe Glu Arg Phe Thr Asp Arg Ala Arg Arg Val Val Val Leu Ala
1               5                   10                  15

Gln Glu Glu Ala Arg Met Leu Asn His Asn Tyr Ile Gly Thr Glu His
            20                  25                  30

Ile Leu Leu Gly Leu Ile His Glu Gly Glu Gly Val Ala Ala Lys Ser
        35                  40                  45

Leu Glu Ser Leu Gly Ile Ser Leu Glu Gly Val Arg Ser Gln Val Glu
    50                  55                  60

Glu Ile Ile Gly Gln Gly Gln Gln Ala Pro Ser Gly His Ile Pro Phe
65                  70                  75                  80

Thr Pro Arg Ala Lys Lys Val Leu Glu Leu Ser Leu Arg Glu Ala Leu
                85                  90                  95

Gln Leu Gly His Asn Tyr Ile Gly Thr Glu His Ile Leu Leu Gly Leu
            100                 105                 110

Ile Arg Glu Gly Glu Gly Val Ala Ala Gln Val Leu Val Lys Leu Gly
        115                 120                 125

Ala Glu Leu Thr Arg Val Arg Gln Gln Val Ile Gln Leu Leu Ser Gly
    130                 135                 140

Tyr Gln Gly Lys Glu Ala Ala Glu Ala Gly Thr Gly Gly Arg Gly Gly
145                 150                 155                 160

Glu Ser Gly Ser Pro Ser Thr Ser Leu Val Leu Asp Gln Phe Gly Arg
                165                 170                 175

Asn Leu Thr Ala Ala Ala Met Glu Gly Lys Leu Asp Pro Val Ile Gly
            180                 185                 190

Arg Glu Lys Glu Ile Glu Arg Val Met Gln Val Leu Ser Arg Arg Thr
        195                 200                 205

Lys Asn Asn Pro Val Leu Ile Gly Glu Pro Gly Val Gly Lys Thr Ala
    210                 215                 220

Val Val Glu Gly Leu Ala Gln Ala Ile Val His Gly Glu Val Pro Glu
225                 230                 235                 240

Thr Leu Lys Asp Lys Gln Leu Tyr Thr Leu Asp Leu Gly Ser Leu Val
                245                 250                 255

Ala Gly Ser Arg Tyr Arg Gly Asp Phe Glu Glu Arg Leu Lys Lys Val
            260                 265                 270

Leu Lys Glu Ile Asn Thr Arg Gly Asp Ile Ile Leu Phe Ile Asp Glu
        275                 280                 285

Leu His Thr Leu Val Gly Ala Gly Ala Ala Glu Gly Ala Ile Asp Ala
    290                 295                 300

Ala Ser Ile Leu Lys Pro Lys Leu Ala Arg Gly Glu Leu Gln Thr Ile
305                 310                 315                 320

Gly Ala Thr Thr Leu Asp Glu Tyr Arg Lys Tyr Ile Glu Lys Asp Ala
                325                 330                 335

Ala Leu Glu Arg Arg Phe Gln Pro Val Gln Val Gly Glu Pro Thr Val
            340                 345                 350

Glu His Thr Ile Glu Ile Leu Lys Gly Leu Arg Asp Arg Tyr Glu Ala
        355                 360                 365

His His Arg Val Ser Ile Thr Asp Ala Ala Met Val Ala Ala Ala Thr
    370                 375                 380

Leu Ala Asp Arg Tyr Ile Asn Asp Arg Phe Leu Pro Asp Lys Ala Ile
385                 390                 395                 400
```

```
Asp Leu Ile Asp Glu Ala Gly Ala Arg Met Arg Ile Arg Arg Met Thr
                    405                 410                 415
Ala Pro Pro Asp Leu Arg Glu Phe Asp Glu Lys Ile Ala Glu Ala Arg
                420                 425                 430
Arg Glu Lys Glu Ser Ala Ile Asp Ala Gln Asp Phe Glu Lys Ala Ala
            435                 440                 445
Ser Leu Arg Asp Arg Glu Lys Thr Leu Val Ala Gln Arg Ala Glu Arg
        450                 455                 460
Glu Lys Gln Trp Arg Ser Gly Asp Leu Asp Val Val Ala Glu Val Asp
465                 470                 475                 480
Asp Glu Gln Ile Ala Glu Val Leu Gly Asn Trp Thr Gly Ile Pro Val
                    485                 490                 495
Phe Lys Leu Thr Glu Ala Glu Thr Thr Arg Leu Leu Arg Met Glu Glu
                500                 505                 510
Glu Leu His Lys Arg Ile Ile Gly Gln Glu Asp Ala Val Lys Ala Val
            515                 520                 525
Ser Lys Ala Ile Arg Arg Thr Arg Ala Gly Leu Lys Asp Pro Lys Arg
        530                 535                 540
Pro Ser Gly Ser Phe Ile Phe Ala Gly Pro Ser Gly Val Gly Lys Thr
545                 550                 555                 560
Glu Leu Ser Lys Ala Leu Ala Asn Phe Leu Phe Gly Asp Asp Asp Ala
                    565                 570                 575
Leu Ile Gln Ile Asp Met Gly Glu Phe His Asp Arg Phe Thr Ala Ser
                580                 585                 590
Arg Leu Phe Gly Ala Pro Pro Gly Tyr Val Gly Tyr Glu Glu Gly Gly
            595                 600                 605
Gln Leu Thr Glu Lys Val Arg Arg Lys Pro Phe Ser Val Val Leu Phe
        610                 615                 620
Asp Glu Ile Glu Lys Ala His Gln Glu Ile Tyr Asn Ser Leu Leu Gln
625                 630                 635                 640
Val Leu Glu Asp Gly Arg Leu Thr Asp Gly Gln Gly Arg Thr Val Asp
                    645                 650                 655
Phe Lys Asn Thr Val Leu Ile Phe Thr Ser Asn Leu Gly Thr Ser Asp
                660                 665                 670
Ile Ser Lys Pro Val Gly Leu Gly Phe Ser Lys Gly Gly Gly Glu Asn
            675                 680                 685
Asp Tyr Glu Arg Met Lys Gln Lys Val Asn Asp Glu Leu Lys Lys His
        690                 695                 700
Phe Arg Pro Glu Phe Leu Asn Arg Ile Asp Asp Ile Ile Val Phe His
705                 710                 715                 720
Gln Leu Thr Arg Glu Glu Ile Ile Arg Met Val Asp Leu Met Ile Ser
                    725                 730                 735
Arg Val Ala Gly Gln Leu Lys Ser Lys Asp Met Ala Leu Val Leu Thr
                740                 745                 750
Asp Ala Ala Lys Ala Leu Leu Ala Lys Arg Gly Phe Asp Pro Val Leu
            755                 760                 765
Gly Ala Arg Pro Leu Arg Arg Thr Ile Gln Arg Glu Ile Glu Asp Gln
        770                 775                 780
Leu Ser Glu Lys Ile Leu Phe Glu Val Gly Pro Gly Gln Val Val
785                 790                 795                 800
Thr Val Asp Val Asp Asn Trp Asp Gly Glu Gly Pro Gly Glu Asp Ala
                    805                 810                 815
```

-continued

```
Val Phe Thr Phe Thr Gly Thr Arg Lys Pro Pro Ala Glu Pro Asp Leu
            820                 825                 830

Ala Lys Ala Gly Ala His Ser Ala Gly Gly Pro Glu Pro Ala Ala Arg
            835                 840                 845
```

TREATMENTS FOR *MYCOBACTERIUM TUBERCULOSIS*

CROSS-REFERENCE TO RELATED APPLICATIONS

This Application is a 35 U.S.C. § 371 National Phase Entry Application of International Application No. PCT/US2012/061066 filed Oct. 19, 2012, which designates the U.S., and which claims benefit under 35 U.S.C. § 119(e) of U.S. Provisional Application No. 61/588,422, filed on Jan. 19, 2012 and U.S. Provisional Application No. 61/548,983, filed on Oct. 19, 2011, the contents of each of which are herein incorporated by reference in their entirety.

GOVERNMENT SUPPORT

This invention was made in part with U.S. Government support from grants GM51923-13 and R21NS067598 from the National Institutes of Health and grant 5RO1A1071881-02 from the National Institute of Allergy and Infectious Diseases. The U.S. Government has certain rights in this invention.

FIELD OF INVENTION

The invention relates to methods of treating *Mycobacterium tuberculosis* infections.

SEQUENCE LISTING

The instant application contains a Sequence Listing which has been submitted in ASCII format via EFS-Web and is hereby incorporated by reference in its entirety. Said ASCII copy, created on Oct. 19, 2012, is named 28670072.txt and is 26,915 bytes in size.

BACKGROUND

Tuberculosis is a devastating disease that affects worldwide about 100 million people and causes nearly 2 million deaths annually, making it one of leading causes of infectious disease mortality. It has been estimated that a third of all humans are infected with latent *Mycobacterium tuberculosis* (Mtb). Moreover, Mtb has become increasingly resistant to available antibiotics. Therefore, identifying new targets for drug development (i.e. enzymes that are essential for viability of Mtb) and developing selective inhibitors of their function is critical if we are to conquer this devastating disease. Ideal targets for drug development should be enzymes essential for bacterial viability that differ in physicochemical properties and specificity from those present in humans.

SUMMARY OF INVENTION

The methods and compositions of the invention described herein are based on the inventors' discovery and characterization of the ClpP1P2 protease complex in Mtb. As described herein, the inventors have demonstrated that ClpP1P2 is necessary for growth and virulence of Mtb. ClpP1P2 is a particularly attractive target for drug development and treatment of Mtb infections because no similar enzyme is present in the cytosol of mammalian cells.

One aspect of the invention relates to a method of treating a *Mycobacterium tuberculosis* infection comprising administering to a subject a composition comprising an inhibitor of ClpP1P2 protease.

In some embodiments, the inhibitor of ClpP1P2 protease is a small molecule. In some embodiments, the inhibitor of ClpP1P2 protease is a protein. In some embodiments, the inhibitor of ClpP1P2 protease is an intrabody. In some embodiments, the inhibitor of ClpP1P2 protease is a peptide. In some embodiments, the inhibitor of ClpP1P2 protease is a peptidomimetic. In some embodiments, the inhibitor of ClpP1P2 protease is an aptamer. In some embodiments, the inhibitor of ClpP1P2 protease is a peptide derivative. In some embodiments, the inhibitor of ClpP1P2 protease is a peptide boronate. In some embodiments, the inhibitor of ClpP1P2 protease is a beta-lactone. In some embodiments, the inhibitor of ClpP1P2 protease is a dipeptide. In some embodiments, the inhibitor of ClpP1P2 protease is a tripeptide. In some embodiments, the inhibitor of ClpP1P2 protease is a variant or fragment of ClpP1 and/or ClpP2. In some embodiments, the variant or fragment of ClpP1 and/or ClpP2 is a peptide or peptide mimetic.

In some embodiments, the inhibitor is an inhibitor of ClpC1. In some embodiments, the inhibitor of ClpC1 is selected from the group consisting of: Novo23 and hexchlorophene.

Another aspect of the invention comprises a method of treating a *M. tuberculosis* infection comprising administering to a subject a composition comprising an activator of ClpP1P2 protease. In some embodiments, the activator is an acyldepsipeptide (ADEP).

Another aspect of the invention comprises a method of treating multi-drug resistant tuberculosis (MDR-TB) or extensively drug-resistant tuberculosis (XDR-TB) comprising administering to a subject, a composition comprising an antibiotic, and a composition comprising an inhibitor or activator of ClpP1P2. In some embodiments, the antibiotic is an aminoglycoside or other anti-tuberculosis antibiotic known to those of ordinary skill in the art.

In some embodiments, the antibiotic and inhibitor or activator of ClpP1P2 are co-administered. In some embodiments, the antibiotic and inhibitor or activator of ClpP1P2 are sequentially administered.

In one aspect, the invention comprises a method of enhancing the activity of an antibiotic comprising administering an inhibitor or activator of ClpP1P2 and the antibiotic to a subject in need of treatment for a *M. tuberculosis* infection. In some embodiments, the antibiotic is an aminoglycoside or other anti-tuberculosis antibiotic known to those of ordinary skill in the art.

In some embodiments, the antibiotic and inhibitor or activator of ClpP1P2 are co-administered. In some embodiments, the antibiotic and inhibitor or activator of ClpP1P2 are sequentially administered.

In one aspect, the invention comprises a method of screening for activators of ClpP1P2 comprising, (a) contacting isolated ClpP1P2 with a detectable substrate or product thereof (e.g. an assayable substrate as described elsewhere herein, including but not limited to, Ac-PKM-amc, Ac-PWM-amc, and Ac-ARM-amc) and a candidate agent, (b) measuring the resulting level of the detectable substrate or product thereof and (c) and comparing the level of the signal from the detectable substrate with a reference signal, wherein a higher level of signal from the detectable substrate of product thereof as compared to the reference indicates the candidate agent is an activator of ClpP1P2.

In one aspect, the invention comprises a method of screening for inhibitors ClpP1P2 comprising, (a) contacting isolated ClpP1P2 with a detectable substrate or product thereof (e.g. an assayable substrate as described elsewhere herein, including but not limited to, Ac-PKM-amc, Ac- PWM-amc, and Ac-ARM-amc), a candidate agent, and a control activator, (b) measuring the resulting level of signal from the detectable substrate and (c) and comparing the level of signal from the detectable substrate or product thereof with a reference signal, wherein a lower level of signal from the detectable substrate or product thereof as compared to the reference indicates the candidate agent is an inhibitor of ClpP1P2.

In one aspect, the invention comprises a method of screening for a modulator of ClpP1P2 or member of the ClpP1P2 complex, the method comprising; contacting isolated ClpP1P2 with a detectable substrate, an activator, and a candidate agent; measuring the resulting level of signal from the detectable substrate; and comparing the level of signal from the detectable substrate with a reference signal, wherein a statistically significantly different level of signal from the detectable substrate as compared to the reference indicates the candidate agent is a modulator of ClpP1P2 or a member of the ClpP1P2 complex.

In one aspect, the invention comprises a method of screening for a substrate of ClpP1P2 comprising; contacting isolated ClpP1P2 with a detectable candidate substrate and a control activator; and measuring the resulting level of signal from the detectable substrate; wherein a detectable signal from the detectable candidate substrate indicates the candidate substrate is a substrate of ClpP1P2.

In some embodiments of the methods of screening, the the isolated ClpP1P2 is further contacted with isolated ClpC1. In some embodiments, the substrate comprises the tripeptide Pro-Lys-Met. In some embodiments, the substrate is N-acetyl-Pro-Lys-Met-aminomethylcoumarin (Ac-Pro-Lys-Met-amc).

In one aspect, the technology described herein relates to a substrate comprising a tripeptide having the sequence of Pro-Lys-Met. In some embodiments, the substrate can further comprise a detectable label. In some embodiments, the substrate is N-acetyl-Pro-Lys-Met-aminomethylcoumarin (Ac-Pro-Lys-Met-amc).

In one aspect, the technology described herein relates to the use of a substrate as described herein in an assay, the assay comprising determining the amount or rate of cleavage of the substrate in the presence of ClpP1P2.

In one aspect, the technology described herein relates to a kit comprising a substrate comprising the tripeptide X-X-Y, wherein X is any amino acid and Y is selected from the group consisting of Met, Leu, Phe, Ala, Asp, and Lys. In some embodiments, the substrate comprises the tripeptide X-X-Met, wherein X is any amino acid. In some embodiments, the substrate comprises the tripeptide X-Lys-Met, wherein X is any amino acid. In some embodiments, the substrate comprises the tripeptide Pro-X-Met, wherein X is any amino acid. In some embodiments, the substrate comprises the tripeptide Pro-B-Met, wherein B is selected from the group consisting of: Arg, Lys, or His. In some embodiments, the substrate comprises the tripeptide Pro-Lys-Met. In some embodiments, the substrate comprising the tripeptide is detectably labeled. In some embodiments, the substrate consists of the tripeptide and a detectable label. In some embodiments, the substrate comprises a tripeptide having the sequence of Pro-Lys-Met and wherein the tripeptide is detectably labeled. In some embodiments, the substrate is N-acetyl-Pro-Lys-Met-aminomethylcoumarin (Ac-Pro-Lys-Met-amc). In some embodiments, the kit can further comprise one or more reagents selected from the group consisting of isolated ClpP1; isolated ClpP2; isolated ClpC1; an activator of ClpP1P2; and a reagent for detecting the detectable label.

Definitions

For convenience, certain terms employed herein in the specification, examples and appended claims are collected here. Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As used herein, the terms "administering" and "introducing" are used interchangeably and refer to the placement of a modulator of ClpP1P2 protease into a subject by a method or route which results in at least partial localization of such agents at a desired site, such as a site of a *M. tuberculosis* bacterium, such that a desired effect(s) is produced.

The terms "subject" and "individual" are used interchangeably herein, and refer to an animal, for example, a human to whom treatment, including prophylactic or therapeutic treatment is provided. For treatment of those conditions or disease states that are specific for a specific animal such as a human subject, the term subject refers to that specific animal. A subject or animals can also include mammals such as rats, mice, rabbits, sheep, cats, dogs, cows, pigs, and non-human primates.

The phrases "parenteral administration" and "administered parenterally" as used herein, refer to modes of administration other than enteral and topical administration, usually by injection, and includes, without limitation, intravenous, intraperitoneal, intramuscular, intraarterial, intrathecal, intraventricular, intracapsular, intraorbital, intracardiac, intradermal, transtracheal, subcutaneous, subcuticular, intraarticular, sub capsular, subarachnoid, intraspinal, intracerebrospinal, and intrasternal injection and infusion. The phrases "systemic administration," "administered systemically", "peripheral administration" and "administered peripherally" as used herein refer to the administration of the modulator of ClpP1P2 protease other than directly into a target site, tissue, or organ, such as the lung, such that it enters the subject's circulatory system and, thus, is subject to metabolism and other like processes.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, a bispecific or multispecific polypeptide agent. Each carrier must be "acceptable" in the sense of being compatible with the other ingredients of the formulation and not injurious to the patient. The terms such as "excipient", "carrier", "pharmaceutically acceptable carrier" or the like are used interchangeably herein.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder associated with *M. tuberculosis* infection. Treatment is generally "effective" if one or more symptoms or clinical markers are reduced. Alternatively, treatment is "effective" if the progression of a disorder is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of the disorder, stabilized (i.e., not worsening) state of the disorder, delay or slowing of disorder progression, amelioration or palliation of the disorder state, and remission (whether partial or total), whether detectable or undetectable. The term "treatment" of a disorder also includes providing relief from the symptoms or side-effects of the disorder (including palliative treatment).

The term "agent" refers to any entity which is normally not present or not present at the levels being administered to a cell, tissue or subject. The agent can be selected from a group comprising: chemicals; small molecules; nucleic acid sequences; nucleic acid analogues; proteins; peptides; aptamers; antibodies; or functional fragments thereof. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, the term "peptide" is used in its broadest sense to refer to compounds containing amino acids, amino acid equivalents or other non-amino groups, while still retaining the desired functional activity of a peptide. Peptide equivalents can differ from conventional peptides by the replacement of one or more amino acids with related organic acids (such as PABA), amino acids or the like or the substitution or modification of side chains or functional groups. The peptides can be linear or cyclic. A peptide can be modified to include one or more of D-amino acids, beta-amino acids, chemically modified amino acids, naturally occurring non-proteogenic amino acids, rare amino acids, and chemically synthesized compounds that have properties known in the art to be characteristic of an amino acid. As used herein, the term "proteogenic" indicates that the amino acid can be incorporated into a protein in a cell through well-known metabolic pathways.

As used herein, the term "peptidomimetic" refers to a molecule which is capable of folding into a defined three-dimensional structure similar to a natural peptide. Peptides and peptidomimetics include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. The peptide or peptidomimetic can be about 5-50 amino acids long, e.g., about 5, 10, 15, 20, 25, 30, 35, 40, 45, or 50 amino acids long.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA, ribosomal DNA and cDNA. Other suitable nucleic acid molecules are RNA, including mRNA, rRNA and tRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, which are each incorporated herein by reference in their entirety.

The term "vector", as used herein, refers to a nucleic acid construct designed for delivery to a host cell or transfer between different host cells. As used herein, a vector can be viral or non-viral.

As used herein, the term "expression vector" refers to a vector that has the ability to incorporate and express heterologous nucleic acid fragments in a cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain a transgenic gene in place of non-essential viral genes. The vector and/or particle may be utilized for the purpose of transferring any nucleic acids into cells either in vitro or in vivo. Numerous forms of viral vectors are known in the art.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene, and polypeptides obtained by translation of mRNA transcribed from a gene. In some embodiments, an expression product is transcribed from a sequence that does not encode a polypeptide, such as a microRNA.

The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons)

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" typically means a decrease by at least about 5%-10% as compared to a reference level, for example a decrease by at least about 20%, or at least about 30%, or at least about 40%, or at least about 50%, or at least about 60%, or at least about 70%, or at least about 80%, or at least about 90% decrease or any decrease between 10-90% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% increase or more or any increase between 10-90% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

BRIEF DESCRIPTION OF THE DRAWINGS

FIG. 1A depicts Coomassie staining of ClpP1 (2.3 μg) and ClpP2 (2.7 μg) after purification. FIG. 1B depicts sequences of ClpP1 (SEQ ID NO: 01) and ClpP2 (SEQ ID NO: 02) proteins expressed in M. smegmatis. Arrows indicate the sites of proteolytic processing determined by Mass Spec and N terminal sequencing of ClpP1 and ClpP2 purified as in FIG. 1A. FIG. 1C demonstrates that ClpP1P2 possesses peptidase activity but only in the presence of activating di-peptide Z-Leu-Leu. ClpP1 or ClpP2 alone did not show any peptidase activity in the absence or presence of the activator. Enzymatic activity was measured fluorometrically using Z-Gly-Gly-Leu-amc. FIG. 1D demonstrates that activators also stimulate degradation of longer peptides (Mca-KKPTPIQLNDpa(Dnp)-amide (SEQ ID NO: 25)) and proteins (FITC casein). FIG. 1D discloses SEQ ID NO: 31.

FIG. 3A depicts size-exclusion chromatography of ClpP1, ClpP2, and ClpP1/ClpP2 mixture was carried out in the absence (upper panel) and presence (lower panel) of activator Z-Leu-Leu using Sephacryl S300 column. Peptidase activity was measured with Z-Gly-Gly-Leu-amc. P3-thyroglobulin—670K, β-globulin—158K, ovalbumin—44K, and E. coli ClpP—300K were used as molecular mass standards. FIG. 3B demonstrates the change in fluorescence emission spectrum of ClpP1/ClpP2 mixture upon addition of activator, which indicates a conformational change upon complex formation between ClpP1 and ClpP2. The addition of activator to ClpP1/ClpP2 mixture shifted the peak of ClpP1 Trp174 emission from 345 to 330 nm (lower panel), while no change was observed for ClpP1 alone (upper panel).

FIG. 4A demonstrates that activity of ClpP1P2 at different ClpP1:ClpP2 ratios. Constant amounts of ClpP2 (0.85 μg) were mixed with increasing amounts of ClpP1, and Z-Gly-Gly-Leu-amc hydrolysis was measured in the presence of activator. Similar results were obtained with constant amounts of ClpP1 and increasing amounts of ClpP2 (data not shown). FIG. 4B depicts cross-linking of ClpP1P2 subunits by glutaraldehyde. After 0.5 h and 20 h incubation at room temperature of ClpP1P2 (12 μg) with 0.125% glutaraldehyde, the reaction mixture was analyzed by SDS PAGE, followed by mass spectrometry. Two high molecular weight bands corresponding to seven crosslinked subunits were found to contain exclusively ClpP1 or ClpP2 peptides, indicating that each ring contains 7 identical ClpP1 or ClpP2 subunits.

FIGS. 5A-5C demonstrate that both ClpP1 and ClpP2 in ClpP1P2 complex form functional active sites with different substrate preferences. FIG. 5A demonstrates that ClpP1P2 protease has inhibitor sensitivity characteristic of serine proteases. Peptidase activity was measured after 30 min preincubation of 1.2 μg of the enzyme with or without inhibitors at room temperature with 0.1 mM Z-Gly-Gly-Leu-amc. FIG. 5B demonstrates the binding of the active-site inhibitor to each subunit. 1.2 μg of ClpP1, ClpP2, or ClpP1/ClpP2 mixture was incubated for 30 min with biotinylated active-site inhibitor fluoroethoxiphosphynil. The binding of the inhibitor was determined by SDS PAGE followed by Western blot analysis with anti-biotin antibody. FIG. 5C depicts the individual input of ClpP1 and ClpP2 in the enzymatic activity of ClpP1P2, ClpP1 or ClpP2 by inactivating by pretreatment with dichloroisocoumarin (0.1 mM) or by an active site mutation (active site Ser to Ala). The inactivated ClpP1 or ClpP2 was then mixed with its normal counterpart in the presence of activator Z-Leu-Leu, and hydrolysis of hydrophobic and acidic peptide substrates and casein was measured.

FIG. 3A showing the dissociation of ClpP1 and ClpP2 tetradecamers into heptamers and their re-association into mixed ClpP1P2 complex in the presence of activator;

FIG. 3B showing physical interaction between the rings; and FIG. 4B demonstrating cross-linking of only one type of subunits within the rings.

FIGS. 7A-7D demonstrate that Mtb ClpP1 and ClpP2 interact in vivo, forming a multi-component protease, and share substantial homology with ClpP1 and ClpP2 homologs in Msm. FIG. 7A depicts C-terminally myc-tagged Mtb ClpP1 and 6xHis (SEQ ID NO: 26)-tagged Mtb ClpP2 expressed in Msm. Lysate (lane 1) was prepared and loaded onto a Ni-column. After extensive washing (lanes 2,3), Ni-bound material was eluted with 50 mM (lane 4), 100 mM (lane 5), 250 mM (lane 6, 7) of imidazole, and analyzed by Western blot using anti α-myc and α-6xHis (SEQ ID NO: 26) antibodies. FIG. 7B depicts Fraction 6 from FIG. 7A bound to an anti-myc column (lane 1). The flow through (lane 2), and bound material (lane 3) were analyzed by Western blot with anti-α-myc and α-6xHis (SEQ ID NO: 26) antibodies. FIG. 7C depicts the results of sequencing bands representing ClpP1 (Mtb is SEQ ID NO: 03; Msm is SEQ ID NO: 04) and ClpP2 (Mtb is SEQ ID NO: 05; Msm is SEQ ID NO: 06) from FIG. 7B by MS/MS, revealing the presence of both Mtb and Msm homologs. Species specific peptides are indicated by black lines above (Msm) or below (Mtb) the sequences. FIG. 7D is a graph of cleavage of fluorescent peptide Z-Gly-Gly-Leu-amc measured in the presence of 1 μg ClpP1, 1 μg Clp2, and the activating peptide Z-Leu-Leu (see accompanying paper). Addition of 5 μg of catalytically inactive mutants of either ClpP1 (ClpP1S) or ClpP2 (ClpP2S) markedly inhibited cleavage by the ClpP1P2 protease. Results graphed are a representative sample of results obtained.

FIGS. 8A-8H demonstrate that both ClpP1 and ClpP2 are essential for normal growth in mycobacteria. FIG. 8A depicts a schematic representation of mycobacterial recombineering, employed to replace the endogenous promoter of the clpP1P2 operon with an ATc-inducible promoter (Msm strain ptet_clpP1P2). FIG. 8B depicts growth curves of Msm ptet_clpP1P2 in the presence (50 ng/mL) or absence of inducer ATc. Data are represented as mean CFU/mL +/− standard deviation. FIG. 8C depicts growth curves of Msm ptet_clpP1P2 complemented with clpP1, clpP2 or both clpP1 and clpP2 in the absence of inducer ATc. Data are represented as mean CFU/mL +/− standard deviation. FIG. 8D depicts a schematic representation of genetic strategy used to create a tetracycline inducible conditional Msm ClpP2 mutant (Msm strain ptet_ClpP2). FIG. 8E depicts growth curves of Msm ptet_clpP2 in the presence (50 ng/mL) or absence of inducer ATc. Msm ptet_clpP2 was also complemented with clpP2 in the absence of ATc. Data are represented as mean OD600 +/− standard deviation. Dashed lines represent assumed growth rates until first measured growth point. FIG. 8F depicts a schematic representation of the inducible degradation system used to inducibly deplete ClpP2 (Msm strain clpP2_ID). Induction of HIV-2 protease with ATc leads to cleavage of the HIV-2 protease cutting site and exposure of an SsrA tag on the tagged protein. Cleavage by HIV protease and subsequent degradation can be tracked via the epitope tags included on the inducible degradation tag. FIG. 8F discloses SEQ ID NOS 35, 36 and 36, respectively, in order of appearance. FIG. 8G demonstrates that the degradation of ClpP2 in clpP2_ID was tracked by Western blot in the absence or presence of inducer ATc. Blots were probed with α-flag (loss indicates HIV-2 protease cleavage), α-myc (loss indicates target degradation), and α-RpoB (loading control). FIG. 8H depicts growth curves of Msm clpP2_ID in the absence or presence (50 ng/mL) of inducer ATc. Msm clpP2_ID was also complemented with clpP2 in the presence of ATc. Data are represented as mean CFU/mL +/− standard deviation.

FIG. 9A depicts growth curves of Msm ptet_clpP2 in growth medium containing low (1 ng/mL) or high (100 ng/mL) concentrations of inducer ATc, in the presence of either no drug (top left), chloramphenicol (top right, 7.5 μg/mL), streptomycin (bottom left, 0.125 μg/mL), or amikacin (bottom left, 0.03 μg/mL). Data are represented as mean $OD_{600}$ +/− standard deviation. Dashed lines represent assumed growth rates until first measured growth point. FIG. 9B demonstrates an increase in fluorescence (RFU, 485/520) and initial growth curve ($OD_{600}$) of Msm clpP2_ID expressing the fusion construct GFP-SsrA on a constitutively expressing plasmid, in the presence and absence of inducer, ATc. Data are represented as mean RFU or $OD_{600}$ +/− standard deviation. FIG. 9C depicts depletion of ClpP2 and an increase in GFP-SsrA in Msm clpP2_ID expressing the fusion construct GFP-SsrA on a constitutively expressing plasmid was tracked by Western blot. Blots were probed with α-GFP, α-myc, α-flag, and α-RpoB (loading control).

FIG. 10A depicts growth curves for Mtb overexpressing wildtype ClpP1, ClpP1-Ser98Ala, or ClpP1-His123Ala, via an ATc-inducible expression vector. Data are represented as mean $OD_{600}$ +/− standard deviation. Dashed lines represent assumed growth rates until first measured growth point. FIG. 10B depicts bacterial multiplication of wildtype Mtb containing empty vector (Control) and Mtb overexpressing the mutant allele ClpP1-His123Ala in lungs (left, N=5/group) and in spleens (right, N=5/group) of C57/B16 mice after intravenous injection of a mixture of control and mutant strains at a ratio of 1:1. Mice were fed with chow with or without inducer doxycycline. Fold increase of colony forming units per organ represents increase on day 27 from day 1. Data are represented as mean CFU/organ +/− standard deviation.

FIGS. 11A-11B depict schematics and electrophoresis gels demonstrating the replacement of the endogenous promoter of clpP1 and clpP2 in Msm with a tetracycline-inducible promoter. FIG. 11A shows a representation of the wildtype Msm DNA and the construct which were introduced to create the ptet_clpP1P2 and ptet_clpP2 strains. FIG. 11B depicts the results of PCR to confirm the mycobacterial recombineering. Primers specific to the 5'-UTR and 3'-UTR (RMR13 and RMR16, arrows) were used to distinguish wildtype Msm (expected fragment: 1.8 kb), Msm ptet_ClpP1P2 (expected size: 4.8 kb), and Msm clpP2_ID (expected size 3.2 kb). For each construct, at least one primer was outside homology region used for recombineering in order to ensure specific insertion into the endogenous chromosome.

FIG. 13A is a graph demonstrating that ClpC1 activates casein but not peptide degradation by ClpP1P2. ClpP1P2 (2.5 µg), ClpC1 (32 µg) were mixed in 100 µl of reaction buffer containing 2 mM ATP and 8 mM $MgCl_2$ in the presence or absence of the peptide activator. Enzymatic activity was measured fluorometrically using Z-Gly-Gly-Leu-AMC or FITC-casein as substrates. The rate of degradation of ClpP1P2 in the presence of the activator was taken as 100%. FIG. 13B depicts a graph demonstrating that ClpC1 activates casein degradation by ClpP1P2 but not by ClpP1 or ClpP2 alone. Degradation of FITC-casein by ClpP1 (2.5 µg), ClpP2 (2.9 µg), or ClpP1P2 (2.7 µg) was measured as in FIG. 13A. FIG. 13C is a graph demonstrating that the stimulation of FITC-casein degradation by ClpP1P2 requires ATP and the peptide activator. Degradation was measured as in FIGS. 13-13B with different concentrations of ClpC1. FIG. 13D is a graph demonstrating that casein stimulates ATPase activity of ClpC1. 2 mg of ClpC1 were incubated with 5 mg FITC-casein in 20 ml of reaction buffer for 30 min and the ATPase activity was measured by Malachite Green method. In control experiments, the effects of ClpP1P2 (4 mg) and the peptide activator on ClpP1 ATPase activity was measured under same conditions.

FIG. 16 depicts graphs demonstrating that ClpC1 activates protein degradation by ClpP1P2 only in the presence of dipeptide activator and ATP.

DETAILED DESCRIPTION OF THE INVENTION

Figures 1A, 1B, 1C, 1D:
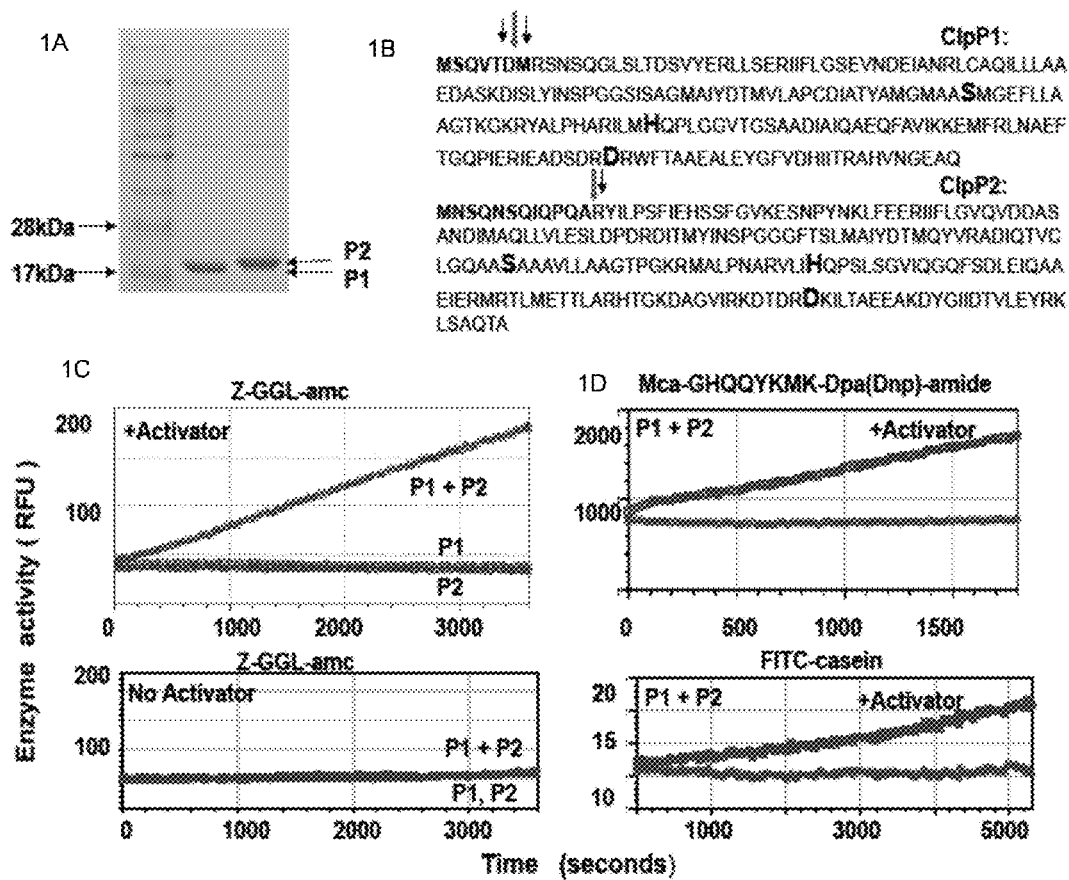
FIGS. 1A-1D depict the purification of processed but inactive ClpP1 and ClpP2 and reconstitution of the active ClpP1P2 complex.

The inventors have demonstrated that ClpP1 and ClpP2 function as complex (ClpP1P2). This protease complex is necessary for growth and virulence *M. tuberculosis* of Mtb. The inventors have also demonstrated that inhibition of ClpP1P2 complex protease activity is detrimental to the virulence and survival of *Mycobacterium*. Accordingly, aspects of the invention described herein are directed to methods of treating Mtb infections by inhibiting ClpP1P2. Methods of enhancing the efficacy of existing antibiotics and methods of treating drug-resistant Mtb infections are also provided. Since ClpP1P2 is essential for Mtb survival and activators of Clp proteases have been associated with indiscriminate proteolysis and toxicity, another aspect of the invention is directed to methods for treating Mtb infections by administration of an activator of ClpP1P2 protease. The inventors have further developed quantitative assays for ClpP1P2 activity that are amenable to high-throughput screens. Accordingly, additional aspects of the invention are directed to methods of screening for modulators of ClpP1P2 protease activity.

ClpP1P2 Protease

Intracellular protein degradation is critical for maintaining cellular homeostasis through protein quality control and regulation of numerous biological pathways (Inger and Brondsted, 2009; Goldberg, 2003). ClpP is a highly conserved, multimeric serine protease originally discovered (Hwang et al., 1987; Katayama-Fujimura et al., 1987) and extensively characterized in *E. coli* (Maurizi et al., 1990b; Maurizi et al., 1998; Maurizi et al., 1994; Yu and Houry, 2007). ClpP homologs exist in a wide range of bacteria, as well as in mitochondria and chloroplasts in eukaryotes (Porankiewicz et al., 1999). By itself, *E. coli* ClpP is able to rapidly hydrolyze only unfolded oligopeptides, but not large globular proteins. The degradation of large proteins requires the presence of an AAA ATPase complex, such as ClpA or ClpX in *E. coli* or ClpC in other species (Kress et al., 2009). These hexameric structures associate with both ends of ClpP to form the active 4-ring ATP-dependent protease (Kim et al., 2001; Maurizi, 1991; Maurizi et al., 1998). These ATPases bind selectively certain protein substrates, unfold them, and translocate the linearized polypeptides into the ClpP proteolytic chamber for degradation (Hoskins et al., 1998; Ishikawa et al., 2001; Ortega et al., 2000; Reid et al., 2001). In addition to substrate recognition, the mitochondrial ClpX complex promotes the assembly of the ClpP complex into an active form (Kang et al., 2005).

In *E. coli*, the ClpXP protease complex has several roles, including regulation of the DNA damage response and degradation of SsrA-tagged peptides stalled on the ribosome (Farrell et al., 2005; Pruteanu and Baker 2009). ClpP also increases the virulence of several pathogenic organisms, including *Listeria monocytogenes*, where the protease is required for the production of α-listeriolysin (Gaillot et al., 2001; Gaillot et al., 2000). In most bacteria, Clp protease is dispensable for normal growth, and in fact, prior to the present report, the only organism in which ClpP has been found to be essential is *Caulobacter crescentus*, where Clp degrades CtrA, an inhibitor of G1-S cell cycle transition (Jenal and Fuchs, 1998).

Most organisms possess a single clpP gene, while some microorganisms (e.g. *Streptomyces, Actinomycetes*, and *Cyanobacteria*) and plants (e.g. *Arabidopsis thaliana*) have two or more clpPs (Butler et al., 2006; Peltier et al., 2004; Peltier et al., 2001; Porankiewicz et al., 1999; Viala and Mazodier, 2002; Viala et al., 2000). The functional significance of these multiple species is unclear. Mtb contains two clpP genes, clpP1 and clpP2, both of which are essential for viability (Sassetti et al., 2003). As described herein, the proteases encoded by clpP1 and clpP2 are required for the growth of Mtb and for virulence during murine infection. As demonstrated herein, ClpP1 and ClpP2 are active only in a mixed complex designated ClpP1P2. Since ClpP1 and ClpP2 are not present in the cytosol of mammalian cells and are markedly different from the mitochondrial Clp, ClpP1 and P2 are highly attractive drug targets.

Modulators of ClpP1P2

A modulator of ClpP1P2 is an agent that either inhibits or increases the protease activity of the ClpP1P2 protease compared to the activity of ClpP1P2 in the absence of the agent.

As used herein, an "inhibitor of ClpP1P2" refers to a compound or agent that reduces ClpP1P2 protease activity. In the aspect of the invention relating to inhibitors of ClpP1P2, inhibition of ClpP1P2 protease activity can be least 10%, at least 20%, at least 30%, at least 50%, at least 75%, at least 80%, at least 90%, at least 95%, at least 98% or more. Preferably, an inhibitor of ClpP1P2 useful in the methods of treating Mtb infections described herein should inhibit ClpP1P2 to the extent that survival and/or growth of the bacterium is decreased at least 10%, at least 20%, at least 30%, at least 50%, at least 75%, at least 80%, at least 90%, at least 95%, at least 98% or more. An inhibitor of ClpP1P2 can be a small molecule; a nucleic acid; a nucleic acid analogue; a protein; an intrabody; a peptide; a peptidomimetic; an aptamer; a peptide derivative; a peptide boronate; a beta-lactone; a dipeptide; a tripeptide; and variants or fragments of ClpP1 and/or ClpP2. In some embodiments, the variant or fragment of ClpP1 and/or ClpP2 is a peptide or peptidomimetic.

As used herein, an "activator of ClpP1P2" refers to a compound or agent that increases ClpP1P2 protease activity. In the aspect of the invention relating to activators of ClpP1P2, activation of ClpP1P2 protease activity can be least 10%, at least 20%, at least 50%, at least 100%, at least 200%, at least 300%, at least 500% or more. Preferably, an activator of ClpP1P2 useful in the methods of treating Mtb infections described herein should activate ClpP1P2 to the extent that survival and/or growth of the bacterium is decreased by at least 10%, at least 20%, at least 30%, at least 50%, at least 75%, at least 80%, at least 90%, at least 95%, at least 98% or more. An activator of ClpP1P2 can be a small molecule; a nucleic acid; a nucleic acid analogue; a protein; an intrabody; a peptide; a peptidomimetic; an aptamer; a peptide derivative; a peptide boronate; a beta-lactone; a dipeptide; a tripeptide; or an acyldepsipeptide (ADEP).

ClpP1P2 activity can be measured by methods well known to those skilled in the art. In certain embodiments, ClpP1P2 activity is measured using detection of a fluorogenic substrate, e.g. as described elsewhere herein. Bacterial growth and survival can be measured by methods well known to those skilled in the art. In one embodiment, bacterial virulence and survival are measured using the murine model of tuberculosis infection described in Example 2 herein.

In certain embodiments provided herein, the modulator of ClpP1P2 activity is an agent which modulates the expression of clpP1 or clpP2.

As used herein, the terms "compound" or "agent" are used interchangeably and refer to molecules and/or compositions that modulate ClpP1P2 activity. The compounds/agents include, but are not limited to, chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies and intrabodies, or fragments thereof.

As used herein, the terms "candidate compound" or "candidate agent" refer to a compound or agent and/or compositions thereof that are to be screened for their ability to modulate ClpP1P2 activity.

Modulators of ClpP1P2 can be produced recombinantly using methods well known to those of skill in the art (see Sambrook et al., Molecular Cloning: A Laboratory Manual (2 ed.), Cold Spring Harbor Laboratory Press, Cold Spring Harbor, N.Y., USA (1989)). Alternatively, modulators of ClpP1P2 can be obtained commercially e.g. dichloroisocoumarin (D7910; Sigma-Aldrich, St. Louis Mo.).

Candidate compounds and agents can be screened for their ability to modulate ClpP1P2 activity in vitro. The modulation of ClpP1P2 activity can also be monitored in vivo. In one embodiment, candidate agents are screened using the assays for ClpP1P2 activity described below herein. In one embodiment, modulation of ClpP1P2 activity is detected by infecting mice with Mtb as described elsewhere herein and administering a candidate agent. A candidate agent can be identified as a possible modulator of ClpP1P2 activity if, for example, lower mortality or less severe symptoms are observed in the infected mice.

Candidate agents are typically first screened for their ability to modulate ClpP1P2 activity in vitro and those candidate agents with such modulatory effects are identified. Positive modulatory agents are then tested for efficacy with respect to modulation of ClpP1P2 in an in vivo infection assay.

Generally, compounds can be tested at any concentration that can modulate expression or protein activity relative to a control over an appropriate time period. In some embodiments, compounds are tested at concentration in the range of about 0.1 nM to about 1000 mM. In one embodiment, the compound is tested in the range of about 0.1 µM to about 20µM, about 0.1 µM to about 10 µM, or about 0.1 µM to about 5 µM. In one embodiment, compounds are tested at 1 µM.

Depending upon the particular embodiment being practiced, the test compounds can be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

To screen candidate agents, an in vitro assay system and/or a cell-based assay system can be used. For example, candidate agents can be screened for binding to a gene or protein encoded by a gene, screened for altering the expression level of a gene, or screened for modulating activity/function of a protein encoded by a gene.

In one embodiment, protein/peptide candidate agents (including antibodies, or fragments thereof or ClpP1 or ClpP2 peptides or peptidomimetics) can be assessed for their ability to bind an encoded protein in vitro. Examples direct binding assays include, but are not limited to, labeled in vitro protein-protein binding assays, electrophoretic mobility shift assays, immunoassays for protein binding, ELISA assays, co-immunoprecipitation assays, competition assays (e.g. with a known binder), and the like. See, e.g., U.S. Pat. Nos. 4,366,241; 4,376,110; 4,517,288; and 4,837,168; and also Bevan et al., Trends in Biotechnology 13:115-122, 1995; Ecker et al., Bio/Technology 13:351-360, 1995; and Hodgson, Bio/Technology 10:973-980, 1992. The test agent can also be identified by detecting a signal that indicates that the agent binds to a protein of interest e.g., fluorescence quenching or FRET. Test agent polypeptides can also be monitored for their ability to bind nucleic acid in vitro, e.g. ELISA-format assays can be a convenient alternative to gel mobility shift assays (EMSA) for analysis of protein binding to nucleic acid. Binding of a test agent to an encoded protein provides an indication the agent may be a modulator of protein activity.

In one embodiment, the candidate agent is assayed for the ability to modulate the biological activity or function of a protein encoded by a gene, e.g. the fluorogenic assays for ClpP1P2 activity described herein.

In one embodiment the test agent is assayed for the ability to modulate transcription of a gene, e.g. a gene encoding ClpP1 or ClpP2. Transcriptional assay are well known to those of skill in the art (see e.g. U.S. Pat. Nos. 7,319,933, 6,913,880,). For example, modulation of expression of a gene can be examined in culture by transient or stable transformation of a reporter expression vector into cultured cells. Candidate agents can be assayed for ability to inhibit or increase expression of a reporter gene (e.g., LacZ gene) under the control of a transcription regulatory element (e.g., promoter sequence) of a gene. An assay vector bearing the transcription regulatory element that is operably linked to the reporter gene can be transfected into a bacterial strain for assays of promoter activity. Reporter genes typically encode polypeptides with an easily assayed enzymatic activity that is naturally absent from the host cell. Vectors expressing a reporter gene under the control of a transcription regulatory element of a gene can be prepared using routinely practiced techniques and methods of molecular biology (see, e.g., e.g., Sambook et al., supra; Brent et al., supra).

In addition to a reporter gene, the vector can also comprise elements necessary for propagation or maintenance in the host cell. Any readily transfectable bacterial strain may be used to assay expression of the reporter gene from the vector, e.g., laboratory strains of *E. coli*, or the Msm strain described elsewhere herein.

Alternatively, modulation of mRNA levels can be assessed using, e.g., biochemical techniques such as Northern hybridization or other hybridization assays, nuclease protection assay, reverse transcription (quantitative RT-PCR) techniques and the like. Such assays are well known to those in the art. In one embodiment, nuclear "run-on" (or "run-off") transcription assays are used (see e.g. Methods in Molecular Biology, Volume: 49, Sep. 27, 1995, Page Range: 229-238). Arrays can also be used; arrays, and methods of analyzing mRNA using such arrays have been described previously, e.g. in EP0834575, EP0834576, WO96/31622, U.S. Pat. No. 5,837,832 or WO98/30883. WO97/10365 provides methods for monitoring of expression levels of a multiplicity of genes using high density oligonucleotide arrays.

In certain embodiments, the modulator of ClpP1P2 is a small molecule. By way of a non-limiting example, dichloroisocoumarin is an inhibitor of ClpP1P2.

Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule (Woburn, Mass.), Panvera (Madison, Wis.), Ryan Scientific (Mt. Pleasant, S.C.), and Enzo Life Sciences (Plymouth Meeting, Pa.). These libraries can be screened for ability to modulate ClpP1P2 using e.g. methods described herein.

In one embodiment the candidate agent is assayed for the ability to inhibit translation of a gene (US Patent Publication 2007/0218079 contains a description of prokaryotic RNAi and is incorporated herein by reference in its entirety). Gene translation can be measured by quantitation of protein expressed from a gene, for example by Western blotting, by an immunological detection of the protein, ELISA (enzyme-linked immunosorbent assay), Western blotting, radioimmunoassay (RIA) or other immunoassays and fluorescence-activated cell analysis (FACS) to detect protein.

Gene silencing or RNAi can be used. In certain embodiments, contacting a cell with the modulator of ClpP1P2 results in a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one embodiment, the mRNA levels are decreased by at least about 70%, about 80%, about 90%, about 95%, about 99%, about 100%. In certain embodiments, the modulator of ClpP1P2 comprises an expression vector or viral vector comprising the RNAi molecule.

In some embodiments, in order to increase nuclease resistance in an agent comprising a nucleic acid as disclosed herein, one can incorporate non-phosphodiester backbone linkages, as for example methylphosphonate, phosphorothioate or phosphorodithioate linkages or mixtures thereof. Other functional groups may also be joined to the oligonucleoside sequence to instill a variety of desirable properties, such as to enhance uptake of the oligonucleoside sequence through cellular membranes, to enhance stability or to enhance the formation of hybrids with the target nucleic acid, or to promote cross-linking with the target (as with a psoralen photo-cross-linking substituent). See, for example, PCT Publication No. WO 92/02532 which is incorporated herein in by reference.

In certain embodiments, the modulator of ClpP1P2 is an intrabody, i.e. an intracellular antibody (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). Monoclonal antibodies are prepared using methods well known to those of skill in the art. Methods for intrabody production are well known to those of skill in the art, e.g. as described in WO 2002/086096. Antibodies will usually bind with at least a KD of about 1 mM, more usually at least about 300 μM, typically at least about 10 μM, more typically at least about 30 μM, preferably at least about 10 μM, and more preferably at least about 3 μM or better.

In certain embodiments, the modulator of ClpP1P2 is a protein or peptide. A peptide agent can be a fragment of a naturally occurring protein, or a mimic or peptidomimetic of a protein of ClpP1P2 or a substrate of ClpP1P2. Agents in the form of a protein and/or peptide or fragment thereof can be designed to modulate a gene or protein involved in ClpP1P2 activity as described herein, i.e. modulate gene expression or encoded protein activity. Such agents are intended to encompass proteins which are normally absent as well as proteins normally endogenously expressed within a cell, e.g. expressed at low levels. Examples of useful proteins are mutated proteins, genetically engineered proteins, peptides, synthetic peptides, recombinant proteins, chimeric proteins, modified proteins and fragments thereof. Modulation of gene expression or protein activity can be direct or indirect. In one embodiment, a protein/peptide agent directly binds to a protein encoded by a gene identified herein, or directly binds to a nucleic acid of a gene identified herein.

Peptides can be screened for inhibitory activity. Peptide libraries, e.g. combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The candidate agents can be naturally occurring proteins or their fragments. Such candidate agents can be obtained from a natural source, e.g., a cell or tissue lysate. Libraries of polypeptide agents can also be prepared, e.g., from a cDNA library commercially available or generated with routine methods. The candidate agents can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides. In some methods, the candidate agents are polypeptides or proteins.

The candidate agents can also be nucleic acids. Nucleic acid candidate agents can be naturally occurring nucleic acids, random nucleic acids, or "biased" random nucleic acids. For example, digests of prokaryotic or eukaryotic genomes can be similarly used as described above for proteins.

Libraries of candidate agents to be screened can also be generated based on structural studies of the proteins, or their fragments, encoded by the genes identified herein. Such structural studies allow the identification of candidate agents that are more likely to bind to the proteins and modulate their activity. The three-dimensional structures of the proteins can be studied in a number of ways, e.g., crystal structure and molecular modeling. Methods of studying protein structures using x-ray crystallography are well known in the literature. See Physical Bio-chemistry, Van Holde, K. E. (Prentice-Hall, New Jersey 1971), pp. 221-239, and Physical Chemistry with Applications to the Life Sciences, D. Eisenberg & D. C. Crothers (Benjamin Cummings, Menlo Park 1979). Computer modeling of structures provides another means for designing candidate agents to screen for modulators. Methods of molecular modeling have been described in the literature, e.g., U.S. Pat. No. 5,612,894 entitled "System and method for molecular modeling utilizing a sensitivity factor," and U.S. Pat. No. 5,583,973 entitled "Molecular modeling method and system." In addition, protein structures can also be determined by neutron diffraction and nuclear magnetic resonance (NMR). See, e.g., Physical Chemistry, 4th Ed. Moore, W. J. (Prentice-Hall, New Jersey 1972), and NMR of Proteins and Nucleic Acids, K. Wuthrich (Wiley-Interscience, New York 1986).

In some embodiments, the candidate agent is a beta-lactone. Beta-lactones can include, but are not limited to, trans-beta-lactones, beta-propiolactone, saturated aliphatic beta-lactones, beta-butyrolactone, beta-isobutyrolactone, beta-valerolactone, beta-isovalerolactone, beta-n-caprolactone, alpha-ethylbeta-propiolactone, alpha-isopropyl-beta-propiolactone, alpha-butyl-beta-propiolactone, alpha isopropyl-beta-propiolactone, beta isopropyl-beta-propiolactone, alpha-butyl-beta-propiolactone, alpha-methyl-beta-butyrolactone, beta-ethyl-beta-butyrolactone, alpha-ethyl-beta-butyrolactone, beta-methyl, beta-valerolactone, alpha-methyl beta-propiolactone, lactones of betahydroxy-mono-carboxylic acids containing cycloalkyl, aryl and aralkyl substituents such as betacyclohexyl-beta-propiolactone, beta-phenyl-betapropiolactone, alpha-phenyl-beta-propiolactone, beta-taenzyl-beta-propiolactone and derivatives thereof. Beta-lactones can include the compounds described in Bottcher and Sieber Am Chem Soc 2008 130:14400-14401; which is incorporated by reference herein in its entirety. Beta-lactones are of the general structure (I):

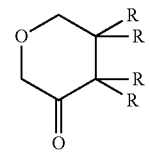

(I)

wherein R is hydrogen or an unreactive hydrocarbon group (i.e., a hydrocarbon group free from aliphatic unsaturation) and may be prepared in the manner described in U.S. Pat. No. 2,356,459. Still other known beta-lactones include lactones of unsaturated betahydroxy carboxylic acids, mono-beta lactones of dicarboxylic acid and di-lactones of dicarboxylic acids in which at least one of the lactones is beta, examples of which are alpha, alpha-dimethyltaeta-propiolactone-beta-carboxylic acid; trimethyl-beta-propiolactone-beta-carboxyllc acid; beta, beta-dimethyl-beta-propiolactone-alpha-carboxylic acid; trimethyl-beta-propiolactonealpha-carboxylic acid, the beta-delta-dilactone of citrylidene malonic acid and derivatives thereof. In addition to these compounds are other compounds containing the structure (II):

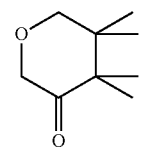

(II)

but having the valences on the alpha and beta carbons attached to groups containing elements other than or in addition to carbon and hydrogen such as oxygen, nitrogen, sulfur and halogen, whether in essentially unreactive structure such as nitro groups and ether linkages or in radicals containing reactive hydrogen such as amino and hydroxy, are also beta-lactones and hence are included within the generic class of beta-lactones. Examples of such latter compounds are alpha or beta-nitrophenyl-beta-propiolactone; beta (Onitro-m-chlorophenyl)-beta-propiolactone; beta(O-nitro-m-methoxyphenyl)-beta-propiolactone; alpha-hydroxy-beta-phenyl-beta-propiolactone and alpha-bromo-beta, beta-dimethyl-betapropiolactone-alpha-carboxylic acid and derivatives thereof.

In some embodiments, the beta lactone has the following structures (III, IV, and V) or is a derivative of any of structures III, IV, and V including as described by Bottcher and Sieber. Chem Bio Chem 2009 10:663-666, which is incorporated by reference herein in its entirety.

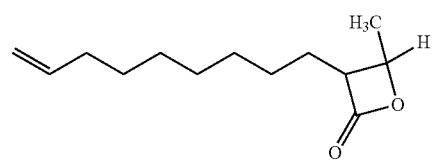

(III)

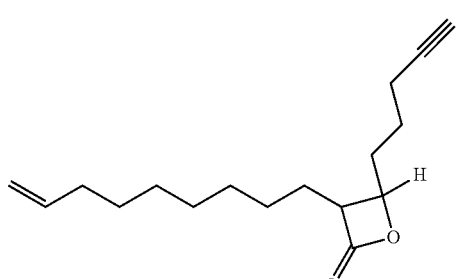

(IV)

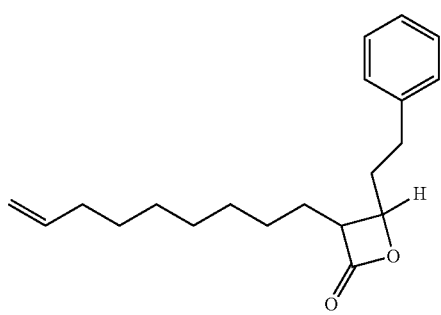

(V)

In some embodiments, the candidate agent is a peptide boronate. Peptide boronates are potent transition-state analogue inhibitors of serine proteinases. Peptide boronates can include any peptide, peptide derivative or peptidomimetic comprising at least one boron atom. The boron atom can be present in a boronic acid, boronate ester, or boronate salt group.

In some embodiments, the candidate agent is an acyldepsipeptide (ADEP). Acyldepsispeptides have the general formula (VI) and are described in U.S. Pat. No. 7,405,201 which is incorporated herein by reference in its entirety.

(VI)

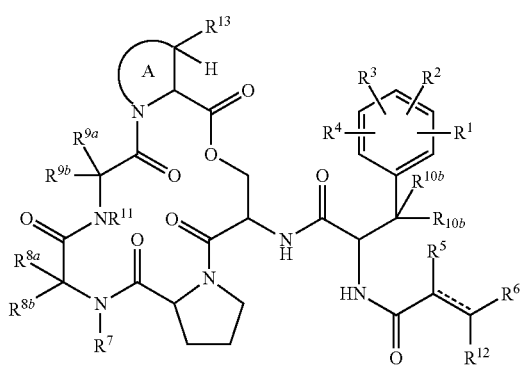

In some embodiments, the candidate agent is ADEP2, ADEP3 or ADEP4 as described in Brotz-Oesterhelt et al. Nature Medicine 2005 11:1082-7; which is incorporated by reference herein in its entirety.

In some embodiments, the candidate agent is an activator of self-compartmentalizing proteases as described in Leung et al. Chemistry & Biology 2011 18:1167-1178. By way of non-limiting example, the candidate agent can have the formula of any of Formulas VII-XIV or be a derivative or analog of any of Formulas VII-XIV. In some embodiments, the candidate agent can be N-1-[2-(phenylthio)ethyl]-2-methyl-2-{[5-(trifluoromethyl)-2-pyridyl]sulfonyl}propanamide (or 2-(5-(trifluoromethyl)pyridin-2-ylsulfonyl)-2-methyl-N-(2-(phenylthio)ethyl)propanamide) (ACP1; Structure VII).

VII

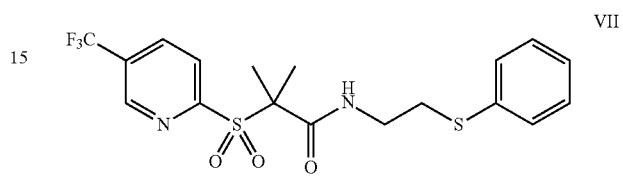

In some embodiments, the candidate agent can be 3-(tert-butoxy)-2-{[2-[(5-(tertbutoxy)-2-{[(9-H-9-fluorenyl-methoxy)carbonyl]amino}-5-oxopentanoyl)amino]-3-(tert-butylsulfanyl)propanoyl]amino}butanoic acid (ACP2; Structure VIII).

VIII

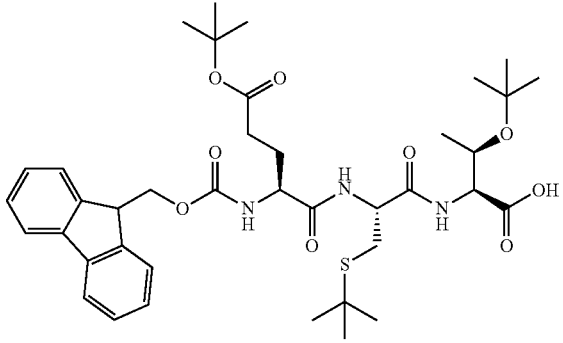

In some embodiments, the candidate agent can be [4-(7-chloroquinolin-4-yl)piperazino](cyclohexyl)Methanone (ACP3; Structure IX).

IX

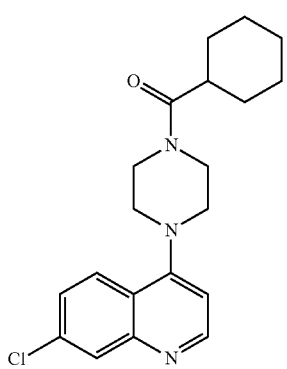

In some embodiments, the candidate agent can be ethyl 2-(2,2-dichloro vinyl)-4-hydroxy4-(3-nitrophenyl)-6-oxocyclohexanecarboxylate (ACP4; Structure X).

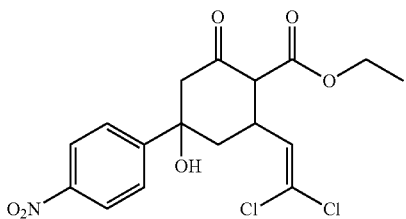

X

In some embodiments, the candidate agent can be ethyl 4-(4-bromophenyl)-2-(2,2-dichlorovinyl)-4-hydroxy-6-oxo-cyclohexanecarboxylate (ACP5; Structure XI).

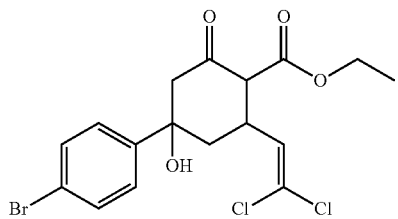

XI

In some embodiments, the candidate agent can be 2-(5-(trifluoromethyl)pyridin-2-ylsulfonyl)-2-methyl-N-(3-phenylpropyl)propanamide (ACP1a; Structure XII).

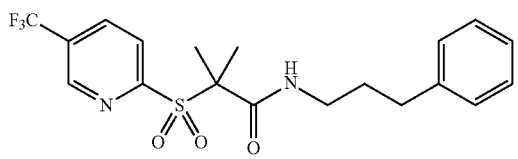

XII

In some embodiments, the candidate agent can be N-(2-(2-chlorophenylthio)ethyl)-2-(5-(trifluoromethyl)pyridin-2-ylsulfonyl)-2-methylpropanamide (ACP1b; Structure XIII).

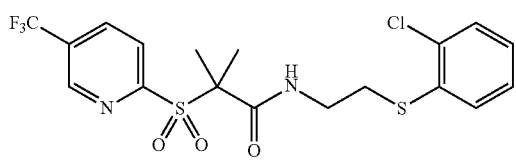

XIII

In some embodiments, the candidate agent can have the formula of Structure XIV.

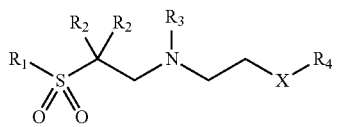

Structure XIV

Wherein $R_1$ is substituted or unsubstituted aryl or heteroaryl; Each $R_2$ is independently hydrogen, $C_{1-4}$alkyl; $R_3$ is hydrogen, $C_{1-4}$alkyl, protecting group; $R_4$ is substituted or unsubstituted aryl or heteroaryl; X is S, O, $NR_3$, or C.

In some embodiments, $R_1$ is aryl. In some embodiments, $R_1$ is substituted or unsubstituted bicyclic aryl. In some embodiments, $R_1$ is unsubstituted aryl. In some embodiments, $R_1$ is substituted aryl. In some embodiments, $R_1$ is substituted with one, two, three, four, or five substituents. In some embodiments, all substituents are the same. In some embodiments, all substituents are different. In some embodiments, at least two substituents are the same. In some embodiments, $R_1$ is a substituted phenyl.

In some embodiments, $R_1$ is a substituted or unsubstituted bicyclic heteroaryl. In some embodiments, $R_1$ is a substituted aryl. In some embodiments, $R_1$ is substituted heteroaryl. In some embodiments, $R_1$ is substituted heteroaryl. In some embodiments, $R_1$ is substituted with one, two, three, four, or five substituents. In some embodiments, all substituents are the same. In some embodiments, all substituents are different. In some embodiments, at least two substituents are the same. In some embodiments, $R_1$ is a substituted pyridine.

In some embodiments, $R_2$ is hydrogen. In some embodiments, $R_2$ is $C_{1-4}$alkyl. In some embodiments, $R_2$ is methyl, ethyl, propyl, or butyl. In some embodiments, each $R_2$ are different. In some embodiments, both $R_2$ are the same. In some embodiments, both $R_2$ are methyl.

In some embodiments, $R_3$ is hydrogen. In some embodiments, $R_3$ is $C_{1-4}$alkyl. In some embodiments, $R_3$ is methyl, ethyl, propyl, or butyl. In some embodiments, $R_3$ is N-protecting group, as known to one of ordinary skill in the art.

In some embodiments, $R_4$ is aryl. In some embodiments, $R_1$ is substituted or unsubstituted bicyclic aryl. In some embodiments, $R_4$ is unsubstituted aryl. In some embodiments, $R_4$ is substituted aryl. In some embodiments, $R_1$ is substituted with one, two, three, four, or five substituents. In some embodiments, all substituents are the same. In some embodiments, all substituents are different. In some embodiments, at least two substituents are the same. In some embodiments, $R_4$ is unsubstituted phenyl. In some embodiments, $R_4$ is substituted phenyl.

In some embodiments, $R_4$ is a substituted or unsubstituted bicyclic heteroaryl. In some embodiments, $R_4$ is a substituted aryl. In some embodiments, $R_4$ is a substituted heteroaryl. In some embodiments, $R_4$ is substituted heteroaryl. In some embodiments, $R_4$ is substituted with one, two, three, four, or five substituents. In some embodiments, all substituents are the same. In some embodiments, all substituents are different. In some embodiments, at least two substituents are the same.

In some embodiments, the candidate compound that is screened and identified to modulate expression of a gene identified herein, or identified to modulate the activity of a protein encoded by a gene identified herein, can modulate ClpP1P2 activity by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more higher relative to an untreated control.

The ClpP1P2 modulatory compounds or agents may function directly in the form in which it is administered. Alternatively, the agent can be modified or utilized intracellularly to produce something which modulates the gene, e.g. introduction of a nucleic acid sequence into the cell and its transcription resulting in the production of an inhibitor or activator of gene expression or protein activity.

The agent may comprise a vector. Many vectors useful for transferring exogenous genes into target cells are available, e.g. the vectors may be episomal, e.g., plasmids, virus derived vectors or may be integrated into the target cell genome, through homologous recombination or random integration. Plasmid vectors can include, but are not limited to, pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif, which is hereby incorporated by reference), pQE, pIH821, pGEX, pET series (see Studier et. al., "Use of T7 RNA Polymerase to Direct Expression of Cloned Genes," *Gene Expression Technology*, vol. 185 (1990), which is hereby incorporated by reference in its entirety). Many viral vectors are known in the art and can be used as carriers of a nucleic acid modulatory compound into the cell, e.g. lambda vector system gt11, gt WES.tB, Charon 4. The nucleic acid incorporated into the vector can be operatively linked to an expression control sequence when the expression control sequence controls and regulates the transcription and translation of that polynucleotide sequence.

The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence. In some examples, transcription of a nucleic acid modulatory compound is under the control of a promoter sequence (or other transcriptional regulatory sequence) which controls the expression of the nucleic acid in a cell-type in which expression is intended. It will also be understood that the modulatory nucleic acid can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

In some embodiments, the modulator of ClpP1P2 is an inhibitor of an ATPase. Some ClpP proteases by themselves are inactive or able to hydrolyze only small peptides, and degradation of proteins occurs in association with ATPase complexes that bind and translocate substrates. Without wishing to be bound by theory, the inventors contemplate that *M. tuberculosis* ClpP1P2 could function in vivo in a similar manner with, for example Mtb ClpC1 or ClpX as responsible ATPases. The *M. tuberculosis* genome contains two such genes. Both ClpC and ClpX, are also essential for viability. Therefore, these ATPases are also attractive drug targets. Without wishing to be bound by theory, one possibility is that these regulatory ATPases in vivo induce the same structural changes in ClpP1P2 as the activator peptides described herein.

An inhibitor of ATPase (i.e. ClpC and/or ClpX) can be a small molecule; a nucleic acid; a nucleic acid analogue; a protein; an intrabody; a peptide; a peptidomimetic; an aptamer; or a peptide derivative. Examples of inhibitors of ATPases are ouabain, vanadate and A-32887. In some embodiments, the inhibitor of ATPase is an inhibitor of the AAA family of hexameric ATPases. Non-limiting examples of inhibitors of the AAA family of hexameric ATPases include $N^2,N^4$-dibenzylquinazoline-2,4-diamine (DBeQ) (as described in Chou et al PNAS 2011 108:4834; which is incorporated by reference herein in its entirety).

In some embodiments, an inhibitor of ClpP1P2 activity can be a modulator of ClpC1, i.e. an agent that increases or decreases ClpC1 activity such that the activity of ClpP1P2 is decreased. Non-limiting examples of modulators of ClpC1 include hexachlorophene and Novo23 (see, e.g. Garvish et al., "A novel antimicrobial from uncultured bacteria with specific activity against *Mycobacterium tuberculosis*." Sixth Annual New England TB Symposium Program Book. Jun. 28, 2012; page 27; which is incorporated by reference herein in its entirety). Such modulators can be obtained commercially, e.g. hexachlorophene (Cat No. H4625; Sigma-Aldrich, St. Louis, Mo.).

In some embodiments, the modulator of ClpP1P2 is a modulator of ATPase. By way of non-limiting example, a modulator of ATPase can be cyclomarin (see Schmitt et al. Angew Chem Int Ed Engl 2011 50:5889-5891; which is incorporated by reference herein in its entirety).

Treatment of *Mycobacterium tuberculosis* Infections

One aspect of the invention relates to a method of treating *M. tuberculosis* (Mtb) infections. These methods comprise administering to a patient a therapeutically effective amount of an inhibitor or activator of ClpP1P2.

Suitable methods for administration of a composition of the present invention include but are not limited to peritoneal, subcutaneous, topical, or oral administration. In one embodiment of the methods described herein, the composition is administered orally. In one embodiment of the methods described herein, the composition is administered intravenously.

In some embodiments, the inhibitor or activator of ClpP1P2 is administered to a subject to whom another antibiotic is also being administered. In some embodiments the other antibiotic is an aminoglycoside. In some embodiments, the inhibitor or activator of ClpP1P2 and the other antibiotic are administered concurrently. In some embodiments, the inhibitor or activator of ClpP1P2 and the other antibiotic are administered sequentially. The method of combining administration of an inhibitor or activator of ClpP1P2 and another antibiotic can be based upon factors such as desired routes of administration, dosages desired, type of antibiotics, severity of the infection, the patient's responsiveness to treatment and other parameters that are assessed by one of ordinary skill in the art in selecting a course of treatment for a particular subject.

Current treatment standards for Mtb infection include a 6 month treatment using the WHO recommended treatment regimen (DOTS, Directly Observed Treatment, Short-course), which consists of 4 drugs isoniazid, rifampacin, pyrazinamide and ethambutol used in combination (WHO Report on the Tuberculosis Epidemic, 2000) over a course of 6 months. In some embodiments, an inhibitor or activator of ClpP1P2 protease can be administered to a patient in addition to isoniazid, rifampacin, pyrzainamide, and ethambutol or in place of one of these antibiotics.

In some embodiments, the pharmaceutical composition comprising an inhibitor or activator of ClpP1P2 comprises additional agents to treat Mtb infections and/or symptoms and complications of an Mtb infection. By way of example, in the case of a subject with an Mtb infection, antibiotics can be administered to treat the infection and administration of steroids or nutritional supplements can also be useful.

Antibiotics used to treat an Mtb infection include, but are not limited to rifampicin, isoniazid, aminoglycosides (i.e. amikacin or kanamycin), polypeptides (i.e. capreomycin), fluoroquinolones, (moxifloxacin or ciprofloxacin), thioamides (i.e. ethionamide or prothionamide), cycloserine, and para-aminosalicylic acid.

Steroids are typically administered to patients with tuberculosis meningitis and tuberculosis pericarditis. Examples of steroids include, but are not limited to, prednisone and dexamethasone.

Nutritional supplements can include, but are not limited to arginine and Vitamin D.

Surgery is also a treatment option for Mtb infections. Surgeries can include, but are not limited to lobectomy and pneumonectomy.

As described elsewhere herein, contacting *Mycobacterium* with the antibiotics streptomycin or amikacin (i.e. aminoglycosides) resulted in much greater inhibition of bacterial growth when ClpP1P2 activity was also compromised. Inhibiting ClpP1P2 activity has an additive effect on inhibiting bacterial growth when administered in combination with existing antibiotics. Protein synthesis is a common target of antibiotic action. Without wishing to be bound by theory, modulation of ClpP1P2 protease activity compromises the cell's ability to address malfunctions in the protein synthesis process. Therefore, the cell is less able to compensate for the perturbation of cellular processed caused by the other antibiotic agent, rendering the other antibiotic more effective. Thus, one aspect of the invention is directed to a method of enhancing the activity of an antibiotic comprising administering an inhibitor or activator of ClpP1P2 and the antibiotic to a subject in need of treatment for a *M. tuberculosis* infection. The antibiotic can be any antibiotic useful in treatment of *M. tuberculosis* infections. In some embodiments, the antibiotic is an aminoglycoside.

Modulators of ClpP1P2 protease activity represent a novel class of antibiotics targeting an essential enzyme required for both survival and virulence of the bacterium. Accordingly, another aspect of the invention is directed to a method of treating multi-drug resistant tuberculosis (MDR-TB) or extensively drug-resistant tuberculosis (XDR-TB) comprising administering to a subject (a) a composition comprising an antibiotic; and (b) a composition comprising an inhibitor or activator of ClpP1P2. In some embodiments, the antibiotic is an aminoglycoside.

Dosage

The dosage of an inhibitor or activator of ClpP1P2 administered according to the methods described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to the treatment regimen.

The dosage ranges for the administration of an inhibitor or activator of ClpP1P2 depend upon the form of the inhibitor or activator of ClpP1P2, and its potency, as described further herein, and are amounts large enough to produce the desired effect in which the symptoms, markers, signs, and/or incidence of Mtb infection are reduced. The dosage should not be so large as to cause substantial adverse side effects. Generally, the dosage can vary with the age, condition, and sex of the patient and can be determined by one of ordinary skill in the art. The dosage can also be adjusted by the individual physician in the event of any complication or based upon the subject's sensitivity to the inhibitor or activator of ClpP1P2. Typically, the dosage ranges from 0.0001 mg/kg body weight to 500 mg/kg body weight. In some embodiments, the dose range is from 0.01 mg/kg body weight to 100 mg/kg body weight. In some embodiments, the dose range is from 0.1 mg/kg body weight to 50 mg/kg body weight.

A composition comprising an inhibitor or activator of ClpP1P2 can be administered over a period of time, such as over a 5 minute, 10 minute, 15 minute, 20 minute, or 25 minute period. The administration can be repeated, for example, on a regular basis, such as hourly for 3 hours, 6 hours, 12 hours or longer or such as biweekly (i.e., every two weeks) for one month, two months, three months, four months or longer. When multiple doses are administered, the doses can be separated from one another by, for example, one hour, three hours, six hours, eight hours, one day, two days, one week, two weeks, or one month.

After an initial treatment regimen, the treatments can be administered on a less frequent basis. For example, after administration biweekly for three months, administration can be repeated once per month, for six months or a year or longer. In some embodiments, administration is chronic, e.g., one or more doses daily over a period of weeks or months.

Administration of a composition comprising an inhibitor or activator of ClpP1P2 can reduce levels of a marker or symptom of Mtb infection by at least 10%, at least 15%, at least 20%, at least 25%, at least 30%, at least 40%, at least 50%, at least 60%, at least 70%, at least 80% or at least 90% or more.

It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity. Effective doses may be extrapolated from dose-response curves derived from, for example, animal model test bioassays or systems.

Dosages for a particular patient or subject can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum or tissue half-life of the inhibitor or activator of ClpP1P2 as disclosed herein, or functional derivatives thereof, and the condition of the patient, as well as, for example, the body weight of the patient to be treated. The size of the dose is also determined by the existence, nature, and extent of any adverse side-effects that accompany the administration of a particular composition, formulation, or the like in a particular subject. Therapeutic compositions comprising an inhibitor or activator of ClpP1P2 or functional derivatives thereof are optionally tested in one or more appropriate in vitro and/or in vivo animal models of disease, such as the murine model of Mtb infection described herein, to confirm efficacy, evaluate tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the $LD_{50}$ of the relevant formulation, and/or observation of any side-effects of an inhibitor or activator of ClpP1P2 or functional derivatives thereof at various concentrations, e.g., as applied to the mass and overall health of the patient. In determining the effective amount of an inhibitor or activator of ClpP1P2 or functional derivatives thereof to be administered in the treatment of adhesions, the physician evaluates, among other criteria, circulating plasma levels, formulation toxicities, and progression of the condition.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage of such compounds lies preferably within a range of circulating concentrations that include the $ED_{50}$ with little or no toxicity. The dosage may vary within this range depending upon the dosage form employed and the route of administration utilized.

With respect to the therapeutic methods of the invention, it is not intended that the administration of the inhibitor or activator of ClpP1P2 be limited to a particular mode of administration, dosage, or frequency of dosing; the present invention contemplates all modes of administration, including intramuscular, intravenous, inhalation, intranasal, oral, intraperitoneal, intravesicular, intraarticular, intralesional, subcutaneous, or any other route sufficient to provide a dose adequate to treat an Mtb infection.

Subjects

Certain aspects of the invention described herein relate to administering an inhibitor or activator of ClpP1P2 to a patient in need of a treatment for an Mtb infection. In some embodiments, the invention comprises first diagnosing the subject, such as a human patient, as having an Mtb infection or suffering from the symptoms of an Mtb infection.

Subjects having an Mtb infection or suffering from the symptoms of an Mtb infection can be identified by a physician using current methods of diagnosing Mtb infections. Symptoms and/or complications of Mtb infection useful in making such diagnoses include, but are not limited to chronic cough, blood-tinged sputum, fever, chest pain, pallor, chills, fatigue, night sweats, and weight loss. If Mtb infection spreads to organs other than the lungs, a variety of symptoms can arise that are specific to the particular organ infected. Test and diagnostic tools that may aid in a diagnosis of Mtb infection include, but are not limited to x-rays, chest x-rays, tuberculin skin test, blood tests, microscopic examination of bodily fluids, microbiological culture of bodily fluids, chest photofluorography, the Ziehl-Neelsen stain, auramine-rhodamine stain, fluorescent microscopy, PCR tests, amplified *mycobacterium tuberculosis* direct test (MTD, Gen-Probe) or an interferon gamma release assay (IGRA).

Subjects can have an elevated risk of having or developing an Mtb infection for a number of reasons. Risk factors that predispose a subject to Mtb include, but are not limited to, certain polymorphisms in the IL12B gene, a family history of Mtb infection, treatment with immunosuppressive drugs, cigarette use, treatment for rheumatoid arthritis with anti-TNFα therapy, illegal drug use, low BMI, AIDS, silicosis, exposure to silica particles, diabetes mellitus, jejunoileal bypass, renal and cardiac transplantation, carcinoma of the head or neck, other neoplasms and incarceration in a prison.

Pharmaceutical Formulations

In one embodiment, a therapeutically effective amount of a composition of the invention is administered to a subject. A "therapeutically effective amount" is an amount of a composition comprising an inhibitor or activator of ClpP1P2 sufficient to produce a measurable improvement in a symptom or marker of Mtb infection. Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, severity of infection and the physical condition and prior medical history of the subject being treated. Determination and adjustment of a therapeutically effective dose, as well as evaluation of when and how to make such adjustments, are known to those of ordinary skill in the art of medicine.

In one embodiment of the methods described herein, a minimally therapeutic dose is administered. The term "minimally therapeutic dose" refers to the smallest dose, or smallest range of doses, determined to be a therapeutically effective amount as that term is used herein.

In some embodiments, a pharmaceutical composition comprises an inhibitor or activator of ClpP1P2, and optionally a pharmaceutically acceptable carrier. The compositions encompassed by the invention may further comprise at least one pharmaceutically acceptable excipient.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the inhibitor or activator of ClpP1P2.

Suitable formulations also include aqueous and non-aqueous sterile injection solutions which can contain antioxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS, for example in the range of in one embodiment about 0.1 to 10 mg/ml, in another embodiment about 2.0 mg/ml; and/or mannitol or another sugar, for example in the range of in one embodiment 10 to 100 mg/ml, in another embodiment about 30 mg/ml; phosphate-buffered saline (PBS), and any other formulation agents conventional in the art.

As described in detail below, the pharmaceutical compositions of the present invention comprising an inhibitor or activator of ClpP1P2 can be specially formulated for administration to a subject in solid, liquid or gel form. By way of non-limiting example, pharmaceutical compositions can be for use in oral administration. Additionally, an inhibitor or activator of ClpP1P2 can be injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960. Examples of dosage forms include, but are not limited to: solutions; gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

Parenteral Dosage Forms

In some embodiments, parenteral dosage forms of an inhibitor or activator of ClpP1P2 can also be administered to a subject who is in need of a treatment for an Mtb infection by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration to a patient, including, but not limited to, administration of DUROS®-type dosage forms, and dose-dumping.

Suitable vehicles that can be used to provide parenteral dosage forms of the inhibitor or activator of ClpP1P2 as disclosed within are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Sterile compositions for parenteral administration may preferably be aqueous or non-aqueous solutions, suspensions or emulsions. Solvents or vehicles that can be used include water, propylene glycol, a polyethylene glycol, plant oils, in particular olive oil, injectable organic esters, for example ethyl oleate, or other suitable organic solvents. These compositions may also comprise adjuvants, in particular wetting agents, tonicity agents, emulsifiers, dispersants and stabilizers. The sterilization may be performed in several ways, for example by aseptic filtration, by incorporating sterilizing agents into the composition, by irradiation or by heating. They may also be prepared in the form of sterile solid compositions that may be dissolved at the time of use in sterile water or any other injectable sterile medium. The sterile compositions can include sterile aqueous solutions which can also contain buffers, diluents and other suitable additives such as, but not limited to, penetration enhancers, carrier compounds and other pharmaceutically acceptable carriers or excipients. Aqueous suspensions can further contain substances which increase the viscosity of the suspension including, for example, sodium carboxymethylcellulose, sorbitol and/or dextran.

Formulations useful in the methods described herein can also include surfactants. Many organized surfactant structures have been studied and used for the formulation of drugs. Suitable surfactants include fatty acids and/or esters or salts thereof, bile acids and/or salts thereof. In certain embodiments of the invention the surfactant can be anionic, cationic, or nonionic. The use of surfactants in drug products, formulations and in emulsions has been reviewed (Rieger, in Pharmaceutical Dosage Forms, Marcel Dekker, Inc., New York, N.Y., 1988, p. 285).

Vesicles, such as liposomes, have attracted great interest because of their specificity and the duration of action they offer from the standpoint of drug delivery. Liposomes are unilamellar or multilamellar vesicles which have a membrane formed from a lipophilic material and an aqueous interior. The aqueous portion contains the composition to be delivered. Liposomes can be cationic (Wang et al., Biochem. Biophys. Res. Commun., 1987, 147, 980-985), anionic (Zhou et al., Journal of Controlled Release, 1992, 19, 269-274), or nonionic (Hu et al. S. T. P. Pharma. Sci., 1994, 4, 6, 466). Liposomes can comprise a number of different phospholipids, lipids, glycolipids, and/or polymers which can impart specific properties useful in certain applications and which have been described in the art (Allen et al., FEBS Letters, 1987, 223, 42; Wu et al., Cancer Research, 1993, 53, 3765; Papahadjopoulos et al. Ann. N.Y. Acad. Sci., 1987, 507, 64; Gabizon et al. PNAS, 1988, 85, 6949; Klibanov et al. FEBS Lett., 1990, 268, 235; Sunamoto et al. Bull. Chem. Soc. Jpn., 1980, 53, 2778; Illum et al. FEBS Lett., 1984, 167, 79; Blume et al. Biochimica et Biophysica Acta, 1990, 1029, 91; Hughes et al. Methods Mol Biol. 2010; 605:445-59; U.S. Pat. Nos. 4,837,028; 5,543,152; 4,426,330; 4,534,899; 5,013,556; 5,356,633; 5,213,804; 5,225,212; 5,540,935; 5,556,948; 5,264,221; 5,665,710; European Patents EP 0 445 131 B1; EP 0 496 813 B1; and European Patent Publications WO 88/04924; WO 97/13499; WO 90/04384; WO 91/05545; WO 94/20073; WO 96/10391; WO 96/40062; WO 97/0478).

The compositions of the present invention can be prepared and formulated as emulsions or microemulsions. Emulsions are typically heterogeneous systems of one liquid dispersed in another in the form of droplets usually exceeding 0.1 μm in diameter and have been described in the art. Microemulsion can be defined as a system of water, oil and amphiphile which is a single optically isotropic and thermodynamically stable liquid solution and can comprise surfactants and cosurfactants. Both of these drug delivery means have been described in the art (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 199, 245, & 335; Higuchi et al., in Remington's Pharmaceutical Sciences, Mack Publishing Co., Easton, Pa., 1985, p. 301; Leung and Shah, in: Controlled Release of Drugs: Polymers and Aggregate Systems, Rosoff, M., Ed., 1989, VCH Publishers, New York, pages 185-215; Schott, in Remington's Pharmaceutical Sciences, Mack Publishing Co., Easton, Pa., 1985, p. 271; Constantinides et al., Pharmaceutical Research, 1994, 11, 1385-1390; Ritschel, Meth. Find. Exp. Clin. Pharmacol., 1993, 13, 205; Ho et al., J. Pharm. Sci., 1996, 85, 138-143; Lee et al., Critical Reviews in Therapeutic Drug Carrier Systems, 1991, p. 92; U.S. Pat. Nos. 6,191,105; 7,063,860; 7,070,802; 7,157,099).

Compounds that alter or modify the solubility of a pharmaceutically acceptable salt of an inhibitor or activator of ClpP1P2 as disclosed herein can also be incorporated into the parenteral dosage forms of the disclosure, including conventional and controlled-release parenteral dosage forms. Such formulations can comprise a controlled-dosage form of the inhibitor or activator of ClpP1P2, e.g. a biodegradable hydrogel comprising an inhibitor or activator of ClpP1P2.

Oral Administration

Formulations for oral administration may be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including EDTA, citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethylammonio-1-propanesulfonate), Big-CHAPS (N, N-bis(3-D-gluconamidopropyl)-cholamide), chlorobutanol, octoxynol-9, benzyl alcohol, phenols, cresols, and alkyl alcohols. An especially preferred oral absorption enhancer for the present invention is sodium lauryl sulfate. Oral formulations and their preparation are described in detail in U.S. Pat. No. 6,887,906, US Publn. No. 20030027780, and U.S. Pat. No. 6,747,014, each of which is incorporated herein by reference.

The oral formulations of the agents described herein, i.e. inhibitors or activators of ClpP1P2, further encompass, in some embodiments, anhydrous pharmaceutical compositions and dosage forms comprising the agents as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure described herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Administration Via Inhalation

An inhibitor or activator of ClpP1P2 as described herein can be administered directly to the airways in the form of an aerosol or by nebulization. Therapeutic agents can be administered as aerosols, packaged in a pressurized aerosol container together with suitable propellants, for example, hydrocarbon propellants like propane, butane, or isobutane with conventional adjuvants. In other embodiments, the agent can be administered in a non-pressurized form such as in a nebulizer or atomizer.

The term "nebulization" is well known in the art to include reducing liquid to a fine spray. Preferably, by such nebulization small liquid droplets of uniform size are produced from a larger body of liquid in a controlled manner. Nebulization can be achieved by any suitable means, including by using many nebulizers known and marketed today. As is well known, any suitable gas can be used to apply pressure during the nebulization, with preferred gases being those which are chemically inert to the therapeutic agent. Exemplary gases include, but are not limited to, nitrogen, argon or helium.

In some embodiments, a therapeutic agent can be administered directly to the airways in the form of a dry powder by use of an inhaler. Exemplary inhalers include metered dose inhalers and dry powdered inhalers. Suitable powder compositions include, by way of illustration, powdered preparations of a therapeutic agent as described herein thoroughly intermixed with lactose, or other inert powders acceptable for, e.g., intrabronchial administration. The powder compositions can be administered via an aerosol dispenser or encased in a breakable capsule which may be inserted by the subject into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994);

French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

Controlled-Release Formulations

In some embodiments, an inhibitor or activator of ClpP1P2 can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, 0, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm & Haas, Spring House, Pa. USA).

Combination Therapies

In some embodiments the methods of the invention for the treatment of an Mtb infection as described herein can also be used in combination with any other therapy known in the art for the treatment of Mtb infection, symptoms and/or complications arising from an Mtb infection or conditions which are associated with Mtb infection. An inhibitor or activator of ClpP1P2 can be administered as the primary therapeutic agent or can be co-administered with one or more additional therapeutic agents.

Efficacy

Efficacy of treatment can be assessed, for example by measuring a marker, indicator, symptom or incidence of a Mtb infection as described herein or any other measurable parameter appropriate, e.g. coughing, fatigue, etc. The Mtb infection can also be examined by, for example, x-ray or IGRA. It is well within the ability of one skilled in the art to monitor efficacy of treatment or prevention by measuring any one of such parameters, or any combination of parameters.

Effective treatment is evident when there is a statistically significant improvement in one or more markers, indicators, or symptoms of an Mtb infection, or by a failure to worsen or to develop symptoms where they would otherwise be anticipated. As an example, a favorable change of at least 10% in a measurable parameter of Mtb infection, and preferably at least 20%, 30%, 40%, 50% or more can be indicative of effective treatment. Efficacy for a given inhibitor or activator of ClpP1P2 or formulation of that drug can also be judged using an experimental animal model known in the art for a condition described herein. When using an experimental animal model, efficacy of treatment is evidenced when a statistically significant change in a marker is observed, e.g. the extent of the Mtb infection or mortality.

Screens for Modulators of ClpP1P2

Provided herein are methods for identifying agents which are modulators of ClpP1P2 protease activity, i.e. inhibitors or activators of ClpP1P2, and/or agents which are members of the ClpP1P2 enzymatic complex (i.e. agents, e.g. peptides, polypeptides, or small molecules which bind, to ClpP1P2 and/or another agent bound to ClpP1P2 and influence the enzymatic activity and/or specificity of ClpP1P2).

In one aspect, the technology described herein comprises a method of screening for activators of ClpP1P2 comprising, (a) contacting isolated ClpP1P2 with a detectable substrate and a candidate agent, (b) measuring the resulting level of the detectable substrate and (c) and comparing the level of the signal from the detectable substrate with a reference signal, wherein a higher level of signal from the detectable substrate as compared to the reference indicates the candidate agent is an activator of ClpP1P2.

In one aspect, the technology described herein comprises a method of screening for inhibitors ClpP1P2 comprising, (a) contacting isolated ClpP1P2 with a detectable substrate, a candidate agent, and a control activator, (b) measuring the resulting level of signal from the detectable substrate and (c) and comparing the level of signal from the detectable substrate with a reference signal, wherein a lower level of signal from the detectable substrate as compared to the reference indicates the candidate agent is an inhibitor of ClpP1P2.

In one aspect, the technology comprises a method of screening for a modulator of ClpP1P2 or member of the ClpP1P2 complex, the method comprising; contacting isolated ClpP1P2 with a detectable substrate, an activator, and a candidate agent; measuring the resulting level of signal from the detectable substrate; and comparing the level of signal from the detectable substrate with a reference signal, wherein a statistically significantly different level of signal from the detectable substrate as compared to the reference indicates the candidate agent is a modulator of ClpP1P2 or a member of the ClpP1P2 complex. As used herein, the term "ClpP1P2 complex" refers to a ClpP1P2 protease and any other molecule and/or agent which is bound to the ClpP1P2 protease, either by directly binding to ClpP1P2 or by indirectly binding, e.g. by binding to a molecule which is itself bound to ClpP1P2. A member of the ClpP1P2 complex can be an activator or an inhibitor of ClpP1P2 protease activity and/or modulate the rate and/or specificity of ClpP1P2 protease.

In one aspect, the technology described herein comprises a method of screening for a substrate of ClpP1P2 comprising; contacting isolated ClpP1P2 with a detectable candidate substrate and a control activator; and measuring the resulting level of signal from the detectable substrate; wherein a detectable signal from the detectable candidate substrate indicates the candidate substrate is a substrate of ClpP1P2.

In some embodiments, any of the foregoing methods can further comprise contacting the isolated ClpP1P2 with isolated ClpC1.

In some embodiments the isolated ClpP1P2 is obtained by expressing ClpP1 and/or ClpP2 in *M. smegmatis* as described elsewhere herein. In some embodiments, the isolated ClpP1P2 is obtained by expressing ClpP1 and/or ClpP2 in *Escherichia coli* as described elsewhere herein. In some embodiments, the ClpP1 and/or ClpP2 are expressed as wild-type forms of the genes. In some embodiments the ClpP1 and/or ClpP2 are expressed as activated forms as described elsewhere herein, i.e. ClpP1 and/or ClpP2 are expressed without the N-terminal portion of the protein which is cleaved to create active forms in vivo. In some embodiments, ClpP1 and ClpP2 are expressed in any bacterial expression system or are synthesized in vitro. ClpP1 and ClpP2 can be expressed and isolated using methods well known to those of ordinary skill in the art, e.g. as described in Sanbrook et al, Molecular Cloning: A Laboratory Manual (3$^{rd}$ Ed) 2001, CSH Press, Cold Spring Harbor, N.Y. Isolated ClpC1 can be obtained by similar methods. The amino acid sequences of ClpP1, ClpP2, and ClpC1 are known in the art (see, e.g. SEQ ID NO: 1 (amino acid sequence of ClpP1); SEQ ID NO: 2 (amino acid sequence of ClpP2), and SEQ ID NO: 37 (amino acid sequence of ClpC1)). One of skill in the art can readily design nucleic acid sequences encoding such polypeptide sequences or naturally-occurring nucleic acid sequences can be used, e.g. the sequences known to encode Mtb ClpP1, ClpP2, and ClpC1.

In some embodiments, the candidate agent is a small molecule, a nucleic acid, a nucleic acid analogue, a protein, an intrabody, a peptide, a peptidomimetic, an aptamer, a peptide derivative, a peptide boronate, a beta-lactone, a dipeptide, a tripeptide, a variant or fragment of ClpP1 and/or ClpP2 or an acyldepsipeptide (ADEP). In some embodiments, the candidate agent is part of a library of candidate agents.

In some embodiments, the control activator is any agent that can activate ClpP1P2 such that activity of ClpP1P2 is detectable prior to the addition of a candidate agent in the assay being used. In some embodiments, the control activator is an N-blocked peptide aldehyde. In some embodiments, the control activator is a dipeptide aldehyde. In some embodiments, the control activator is Z-Leu-Leu. In some embodiments, the control activator is Z-Leu-Leu-alcohol. In some embodiments, the control activator is Z-Leu-Leu-aldehyde. In some embodiments, the control activator is Z-Leu-Nle-aldehyde. In some embodiments, the control activator is Z-Leu-Leu-aldehyde. In some embodiments, the control activator is Z-Leu. In some embodiments, the control activator is Z-Leu-alcohol. In some embodiments, the control activator is Z-Gly-Leu. In some embodiments, the control activator is Z-Gly-Gly-Leu.

Measuring and Comparing a Signal from a Detectable Substrate

Enzymatic activity is determined based upon specific cleavage of an enzyme substrate conjugated with e.g. a fluorochrome into a readily detectable moiety. The use of substrate molecules comprising fluorescently detectable moieties in conventional assays of enzymatic activities is well established, and can be used in the present invention.

In some embodiments, the detectable substrate can be any substrate bound by ClpP1P2 and cleaved such that the signal of a detectable label is altered upon cleavage. In some embodiments, the detectable label can be any moiety that, when cleaved from an enzymatic substrate by the activity of the enzyme, forms a detectable moiety (e.g., emits light), but that is not detectable in its conjugated state. As used herein, the term "detectable label" refers to a composition detectable by visual, spectroscopic, photochemical, biochemical, immunochemical, or chemical means. Detectable labels include, but are not limited to, fluorescent compounds, isotopic compounds, chromogenic compounds, chelating agents, dyes, quantum dot labels, colloidal gold, latex particles, ligands (e.g., biotin), bioluminescent materials, chemiluminescent agents, enzymes, electron-dense reagents, and haptens or proteins for which antisera or monoclonal antibodies are available. Other detectable labels for use in the invention include magnetic beads or magnetic resonance imaging labels. The various means of detection include but are not limited to spectroscopic, photochemical, radiochemical, biochemical, immunochemical, or chemical means.

Preferred detectable labels for use in the present invention include fluorescent or chromogenic moieties, including, without limitation, fluoresceine isothiocyanate, phycoerythrin, Texas red, rhodamine, free or chelated lanthanide series salts, 4-methylumbelliferone or fluorescein. M-nitrophenyl or p-nitrophenyl compounds also may be used. In some embodiments, the detectable moiety is 7-amido-4-methylcoumarin (amc).

The detectable label is chemically attached to the detectable enzyme substrate in a manner that cleavage by an enzyme results in the detectable label being freed from the conjugate. Techniques which can be used in making the conjugates are known to those of ordinary skill in the art.

In some embodiments, the product of the enzyme interaction is determined by spectrometric measurement, including fluorimetry or colorimetry. By way of non-limiting example, the specific enzyme substrate may comprise a 7-amido-4-methylcoumarin (AMC) derivative, which on interaction with ClpP1P2 releases AMC which is monitored fluorimetrically. Alternatively, the substrate may comprise a nitrophenyl, nitroaniline or similar type of derivative, which on interaction with the enzyme gives rise to a colored product which is monitored colorimetrically. In some embodiments, the substrate is Z-Gly-Gly-Leu-amc (Catalog # BML-ZW8505-0005, Enzo Life Sciences; Plymouth Meeting, Pa.). In some embodiments, the substrate is Suc-Ala-Ala-Phe-ame (Catalog # AMC084, MP Biochemicals, LLC; Solon, Ohio). In some embodiments, the substrate is Ala-Ala-Phe-amc (Catalog #3201-v, PeptaNova; Sandhausen, Germany). In some embodiments, the substrate is Ac-nLPnLD-amc. In some embodiments, the substrate is FITC-casein. In some embodiments, the substrate is Ac-nLPnLD-amc. In some embodiments, the substrate is Mca-GNTQFKRR-Dpa(Dnp)-amide (SEQ ID NO: 27). In some embodiments, the substrate is Mca-GHQQYAMK-Dpa(Dnp)-amide (SEQ ID NO: 28). In some embodiments, the substrate is Ac-nLPnLD-amc. In some embodiments, the substrate is Mca-GNQQYKMK-Dpa(Dnp)-amide (SEQ ID NO: 29). In some embodiments, the substrate is Mca-KKPTPIQLN-Dpa(Dnp)-amide (SEQ ID NO: 30). In some embodiments, the substrate is Suc-LY-amc. In some embodiments, the substrate is AC-PKM-amc. In some embodiments, the substrate is Ac-PWM-amc. In some embodiments, the substrate is Ac-ARM-amc.

In some embodiments, the substrate comprises the tripeptide X-X-Met, wherein X can be any amino acid, e.g. any naturally occurring amino acid. In some embodiments, the substrate comprises the tripeptide X-Lys-Met, wherein X can be any amino acid, e.g. any naturally occurring amino acid. In some embodiments, the substrate comprises the tripeptide Pro-X-Met, wherein X can be any amino acid, e.g. any naturally occurring amino acid. In some embodiments, the substrate comprises the tripeptide Pro-B-Met, wherein B can be any basic amino acid, e.g. Arg, Lys, or His.

In some embodiments, the substrate comprises the tripeptide Pro-Lys-Met.

In some embodiments, the substrate comprises the tripeptide X-X-Y, wherein X can be any amino acid, e.g. any naturally occurring amino acid and Y is selected from the group consisting of Leu, Phe, Ala, Asp, and Lys.

In some embodiments, the substrate is an N-acetyl tripeptide-aminomethylcoumarin. In some embodiments, the substrate is N-acetyl X-X-Met-aminomethylcoumarin, wherein X can be any amino acid, e.g. any naturally occurring amino acid. In some embodiments, the substrate is N-acetyl X-Lys-Met-aminomethylcoumarin, wherein X can be any amino acid, e.g. any naturally occurring amino acid. In some embodiments, the substrate is N-acetyl Pro-X-Met-aminomethylcoumarin, wherein X can be any amino acid, e.g. any naturally occurring amino acid. In some embodiments, the substrate is N-acetyl Pro-B-Met-aminomethylcoumarin, wherein B can be any basic amino acid, e.g. Arg, Lys, or His.

In some embodiments, the substrate is N-acetyl-Pro-Lys-Met-aminomethylcoumarin (Ac-Pro-Lys-Met-amc).

In some embodiments, the substrate is N-acetyl X-X-Y-aminomethylcoumarin, wherein X can be any amino acid, e.g. any naturally occurring amino acid and Y is selected from the group consisting of Leu, Phe, Ala, Asp, and Lys.

In some embodiments, in order to more precisely define ClpP1P2 substrate preferences or to identify a new or improved substrate, a library of fluorescent tripeptide substrates is screened. Without wishing to be bound by theory, precisely defining active site binding preferences allows the design and synthesis of more potent inhibitors of ClpP1P2 activity. In some embodiments, based on the structures of the best substrates, boronate or aldehyde derivatives (that inhibit serine proteases) are synthesized and their potency against ClpP1P2 tested. In some embodiments, screening of a library of boronates for potential inhibitors of ClpP1P2 activity is conducted. In some embodiments, beta-lactones, which have been recently shown to inhibit ClpP in *Staphylococcus aureus* (Bottcher, T., and Sieber, S. A. (2008) J Am Chem Soc 130, 14400-14401) are screened. In some embodiments, identified inhibitors are used in a counterscreen with human proteasome purified from HeLa cells to eliminate agents that may affect host protein degradation.

In some embodiments, a 2-step screen for inhibitors of activators of ClpP1P2 is conducted. Without wishing to be bound by theory, in addition to inhibitors of ClpP1P2, potent activators should be deleterious for *M. tuberculosis*, since a new class of antibiotics, acyldepsipeptides, has been shown to cause toxicity in gram positive bacteria by causing uncontrolled activation of ClpP (Kirstein et al. (2009) *EMBO Mol Med* 1, 37-49). In some embodiments, a 2-step high throughput effort to identify both types of regulators is conducted. Phase 1 consists of looking for small molecules that cause dramatic stimulation of ClpP1P2 activity in the absence of a standard activator. Phase II is conducted in the presence of a standard activator and is aimed at finding compounds that inhibit ClpP1P2 activity. In some embodiments, candidates will be also used in a counterscreen with mammalian proteasomes to eliminate agents that may affect the major proteolytic activity in human cytosol.

In some embodiments, the library of candidate activators of ClpP1P2 comprises acyldepsipeptides (ADEPs).

In some embodiments, the selection of candidate agents for screening, or the modification of candidate agents for screening comprises perfusing crystals of ClpP1P2 with candidate agents and then solving the structure of the complex to determine how candidate agents are binding ClpP1P2 or are bound by ClpP1P2.

In some embodiments, candidate agents identified as modulators of ClpP1P2 using any of the methods described herein, are tested for their effect on microbial growth and viability in vivo. In some embodiments, one or more of the fluorescent substrates described herein is used to monitor ClpP1P2 activity in living cells. In some embodiments, this allows evaluation of drug uptake, which is a known obstacle in anti-mycobacterial drug development.

Instruments for measuring fluorescence or other emissions are well-known in the art. Spectrometers for detecting fluorescence and other emissions are available from PerkinElmer and Thermo Scientific, for example. In some embodiments, the system of the present invention utilizes a detection means which comprises a light emitter and a light sensor, preferably integrated into a single unit. The system further comprises a data processor capable of analyzing the emissions data and providing a read-out or result. In some embodiments, the detection means and the data processor are integrated for this purpose.

The system further may comprise a means for transmitting the data to a receiver, such as a computer. The transmitting means may comprise wireless transmission, e.g., via a cellular network or wireless internet, or may be a direct connection e.g., via a USB connection to the receiving computer, i.e. the data processor, which analyzes the results and provides a read-out.

When the level of signal from the detectable moiety is determined, one skilled in the art, or optionally, the data processor (e.g. a computer) can compare the level of signal from the detectable moiety obtained in the presence of the candidate agent to a reference level. The signal is higher or lower than the reference level if it is higher or lower by a statistically significant amount.

The reference level can be the level of signal of the detectable moiety when no candidate agent is present. In some embodiments, the reference level is the level of signal of the detectable moiety when a control activator is present. In some embodiments a control activator is used to determine the reference level in order to screen for an inhibitor. In some embodiments, a control activator is used to determine the reference level in order to screen for an activator which can activate ClpP1P2 to a greater extent than the control activator.

In some embodiments, the assay to which the candidate agent is added, and/or the reference level can comprise additional agents in order to screen for interactions between two or more modulators and/or potential modulators of ClpP1P2 activity.

Aspects of the technology described herein further relate to kits comprising the compositions described herein and kits for practicing the methods described herein. In some embodiments the technology described herein can relate to a substrate and/or a kit comprising a substrate. Such a substrate and/or kit can be directed to determining the activity of ClpP1P2 and/or screening for modulators of ClpP1P2 activity as described elsewhere herein. A kit is any manufacture (e.g., a package or container) comprising at least one reagent, e.g., a substrate, for determining and/or measuring the activity of ClpP1P2 and/or ClpC1, the manufacture being promoted, distributed, or sold as a unit for performing the methods or assays described herein.

In one aspect, described herein is a substrate comprising a tripeptide having the sequence of Pro-Lys-Met. In some embodiments, the substrate can further comprise a detectable label. In some embodiments, the substrate can be N-acetyl-Pro-Lys-Met-aminomethylcoumarin (Ac-Pro-Lys-Met-amc). In one aspect, described herein is the use of the substrate in an assay, the assay comprising determining the amount or rate of cleavage of the substrate in the presence of ClpP1P2.

In one aspect, described herein is a kit comprising a substrate comprising the tripeptide X—X—Y, wherein X is any amino acid and Y is selected from the group consisting of Met, Leu, Phe, Ala, Asp, and Lys. In some embodiments, the substrate can comprise the tripeptide X-X-Met, wherein X is any amino acid. In some embodiments, the substrate can comprise the tripeptide X-Lys-Met, wherein X is any amino acid. In some embodiments, the substrate can comprise the tripeptide Pro-X-Met, wherein X is any amino acid. In some embodiments, the substrate can comprise the tripeptide Pro-B-Met, wherein B is selected from the group consisting of: Arg, Lys, or His. In some embodiments, the substrate can comprise the tripeptide Pro-Lys-Met. In some embodiments, the substrate comprising the tripeptide can be detectably labeled. In some embodiments, the substrate can consist of the tripeptide and a detectable label. In some embodiments, the substrate can comprise a tripeptide having the sequence of Pro-Lys-Met wherein the tripeptide is detectably labeled. In some embodiments, the substrate can be N-acetyl-Pro-Lys-Met-aminomethylcoumarin (Ac-Pro-Lys-Met-amc).

The kits described herein can optionally comprise additional components useful for performing the methods and assays described herein. By way of example, the kit can comprise fluids (e.g., buffers) suitable for suspending e.g. ClpP1, ClpP2 and/or ClpP1P2, one or more sample compartments, an instructional material which describes performance of a method as described herein, a sample of a known reference modulator of ClpP1P2 activity and the like. In some embodiments, the kit can further comprise one or more reagents selected from the group consisting of: isolated ClpP1; isolated ClpP2; isolated ClpC1; an activator of ClpP1P2; and a reagent for detecting the detectable label.

Kits can further comprise suitable packaging and/or instructions for use of the kit and/or substrate. The kits can include appropriate instructions and information for preparing and performing an assay or screen as described herein, and any other relevant information. The instructions can be in any suitable format, including, but not limited to, printed matter, videotape, computer readable disk, or optical disc.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The technology described herein is further illustrated by the following examples which in no way should be construed as being further limiting.

Some embodiments of the technology described herein can be defined according to any of the following numbered paragraphs:

1. A method of treating a *Mycobacterium tuberculosis* infection comprising administering to a subject a composition comprising an inhibitor of ClpP1P2 protease.
2. The method of paragraph 1, wherein the inhibitor is selected from the group consisting of: a small molecule; a nucleic acid; a nucleic acid analogue; a protein; an intrabody; a peptide; a peptidomimetic; an aptamer; a peptide derivative; a peptide boronate; a beta-lactone; a dipeptide; a tripeptide; and variants or fragments of ClpP1 and/or ClpP2.
3. The method of paragraph 2, wherein the variant or fragment of ClpP1 and/or ClpP2 is a peptide or peptide mimetic.
4. The method of paragraph 2, wherein the inhibitor is an inhibitor of ClpC1.
5. The method of paragraph 4, wherein the inhibitor of ClpC1 is selected from the group consisting of: Novo23 and hexchlorophene.
6. A method of treating a *M. tuberculosis* infection comprising administering to a subject a composition comprising an activator of ClpP1 P2 protease.
7. The method of paragraph 6, wherein the activator is an acyldepsipeptide (ADEP).
8. A method of treating multi-drug resistant tuberculosis (MDR-TB) or extensively drug-resistant tuberculosis (XDR-TB) comprising administering to a subject; a composition comprising an antibiotic; and a composition comprising an inhibitor or activator of ClpP1P2.
9. The method of paragraph 8, wherein the antibiotic is an aminoglycoside.
10. The method of any of paragraphs 8-9, wherein the inhibitor or activator of ClpP1P2 is selected from the group consisting of:
    a small molecule; a nucleic acid; a nucleic acid analogue; a protein; an intrabody; a peptide; a peptidomimetic; an aptamer; a peptide derivative; a peptide boronate; a beta-lactone; a dipeptide; a tripeptide; an ADEP and variants or fragments of ClpP1 and/or ClpP2.

11. The method of paragraphs 8-10, wherein the inhibitor is an inhibitor of ClpC1.
12. The method of paragraph 11, wherein the inhibitor of ClpC1 is selected from the group consisting of: Novo23 and hexchlorophene.
13. The method of any of paragraphs 8-12, wherein the antibiotic and inhibitor or activator of ClpP1P2 are co-administered.
14. The method of any of paragraphs 8-12, wherein the antibiotic and inhibitor or activator of ClpP1P2 are sequentially administered.
15. A method of enhancing the activity of an antibiotic comprising administering an inhibitor or activator of ClpP1P2 and the antibiotic to a subject in need of treatment for a M. tuberculosis infection.
16. The method of paragraph 15, wherein the antibiotic is an aminoglycoside.
17. The method of any of paragraphs 15-16, wherein the inhibitor or activator of ClpP1P2 is selected from the group consisting of:
    a small molecule; a nucleic acid; a nucleic acid analogue; a protein; an intrabody; a peptide; a peptidomimetic; an aptamer; a peptide derivative; a peptide boronate; a beta-lactone; a dipeptide; a tripeptide; an ADEP and variants or fragments of ClpP1 and/or ClpP2.
18. The method of any of paragraphs 15-17, wherein the inhibitor is an inhibitor of ClpC1.
19. The method of paragraph 18, wherein the inhibitor of ClpC1 is selected from the group consisting of: Novo23 and hexchlorophene.
20. The method of any of paragraphs 15-19, wherein the antibiotic and inhibitor or activator of ClpP1P2 are co-administered.
21. The method of any of paragraphs 15-19, wherein the antibiotic and inhibitor or activator of ClpP1P2 are sequentially administered.
22. A method of screening for activators of ClpP1P2 comprising;
    contacting isolated ClpP1P2 with a detectable substrate and a candidate agent;
    measuring the resulting level of signal from the detectable substrate;
    and comparing the level of signal from the detectable substrate with a reference signal,
    wherein a higher level of signal from the detectable substrate as compared to the reference indicates the candidate agent is an activator of ClpP1P2.
23. A method of screening for inhibitors ClpP1P2 comprising;
    contacting isolated ClpP1P2 with a detectable substrate, a candidate agent, and a control activator;
    measuring the resulting level of signal from the detectable substrate;
    and comparing the level of signal from the detectable substrate with a reference signal,
    wherein a lower level of signal from the detectable substrate as compared to the reference indicates the candidate agent is an inhibitor of ClpP1P2.
24. A method of screening for a modulator of ClpP1P2 or member of the ClpP1P2 complex, the method comprising;
    contacting isolated ClpP1P2 with a detectable substrate, an activator, and a candidate agent; measuring the resulting level of signal from the detectable substrate; and comparing the level of signal from the detectable substrate with a reference signal,
    wherein a statistically significantly different level of signal from the detectable substrate as compared to the reference indicates the candidate agent is a modulator of ClpP1P2 or a member of the ClpP1P2 complex.
25. A method of screening for a substrate of ClpP1P2 comprising;
    contacting isolated ClpP1P2 with a detectable candidate substrate and a control activator; and
    measuring the resulting level of signal from the detectable substrate;
    wherein a detectable signal from the detectable candidate substrate indicates the candidate substrate is a substrate of ClpP1P2.
26. The method of any of paragraphs 22-25, wherein the isolated ClpP1P2 is further contacted with isolated ClpC1.
27. The method of any of paragraphs 22-26, wherein the substrate comprises the tripeptide Pro-Lys-Met.
28. The method of paragraph 27, wherein the substrate is N-acetyl-Pro-Lys-Met-aminomethylcoumarin (Ac-Pro-Lys-Met-amc).
29. A substrate comprising a tripeptide having the sequence of Pro-Lys-Met.
30. The substrate of paragraph 29, further comprising a detectable label.
31. The substrate of paragraph 30, wherein the substrate is N-acetyl-Pro-Lys-Met-aminomethylcoumarin (Ac-Pro-Lys-Met-amc).
32. The use of the substrate of any of paragraphs 29-31 in an assay, the assay comprising determining the amount or rate of cleavage of the substrate in the presence of ClpP1P2.
33. A kit comprising a substrate comprising the tripeptide X-X-Y, wherein X is any amino acid and Y is selected from the group consisting of Met, Leu, Phe, Ala, Asp, and Lys.
34. The kit of paragraph 33, wherein the substrate comprises the tripeptide X-X-Met, wherein X is any amino acid.
35. The kit of paragraph 34, wherein the substrate comprises the tripeptide X-Lys-Met, wherein X is any amino acid.
36. The kit of paragraph 34, wherein the substrate comprises the tripeptide Pro-X-Met, wherein X is any amino acid.
37. The kit of paragraph 36, wherein the substrate comprises the tripeptide Pro-B-Met, wherein B is selected from the group consisting of:
    Arg, Lys, or His.
38. The kit of any of paragraphs 37, wherein the substrate comprises the tripeptide Pro-Lys-Met.
39. The kit of any of paragraphs 33-38, wherein the substrate comprising the tripeptide is detectably labeled.
40. The kit of any of paragraphs 33-39, wherein the substrate consists of the tripeptide and a detectable label.
41. The kit of any of paragraphs 33-40, wherein the substrate comprises a tripeptide having the sequence of Pro-Lys-Met and wherein the tripeptide is detectably labeled.
42. The kit of paragraph 40, wherein the substrate is N-acetyl-Pro-Lys-Met-aminomethylcoumarin (Ac-Pro-Lys-Met-amc).
43. The kit of any of paragraphs 33-42, further comprising one or more reagents selected from the group consisting of:
    isolated ClpP1; isolated ClpP2; isolated ClpC1; an activator of ClpP1P2; and a reagent for detecting the detectable label.

EXAMPLES

Example 1: The Active ClpP Protease from *Mycobacterium tuberculosis* is a Complex Composed of a Heptameric ClpP1 and a ClpP2 Ring Mtb contains two clpP genes, clpP1 and clpP2, both of which are essential for viability (Sassetti et al, 2003) and infectivity, as shown in Example 2. Although both appear to encode serine proteases, prior attempts (Benaroudj et al, 2011; Ingvarsson et al, 2007) to express and characterize Mtb ClpP1 and ClpP2 in *E. coli* yielded complexes that lacked proteolytic activity, as did our initial attempts to express ClpP1 and ClpP2 in *E. coli*. The inventors hypothesized that those attempts failed because they were based on the assumption that ClpP1 and ClpP2 are distinct enzymes, while in fact, the active enzyme in vivo is a mixed complex.

It is demonstrated herein that ClpP1 and ClpP2, when overproduced independently, form tetradecameric complexes that lack any proteolytic activity. However, when these complexes are mixed together in the presence of certain small activating molecules, these tetradecamers dissociate into heptameric rings, which then re-associate into a mixed tetradecameric complex that is capable of degrading model peptides as well as some unstructured proteins. These low molecular weight activators clearly represent a novel form of enzyme regulation and stimulate ClpC1C2 activity in a very different manner from the regulatory ATPase complex, ClpC1, which are shown herein to specifically enhance the degradation of proteins. Thus, ClpP1P2 differs markedly from other members of the ClpP family and has a number of highly unusual structural, enzymatic and regulatory properties. These unique qualities of ClpP1P2, taken together with its essential role during infection, make it an attractive target for drug development.

Isolation of Processed ClpP1 and ClpP2.

Figures 3A, 3B:
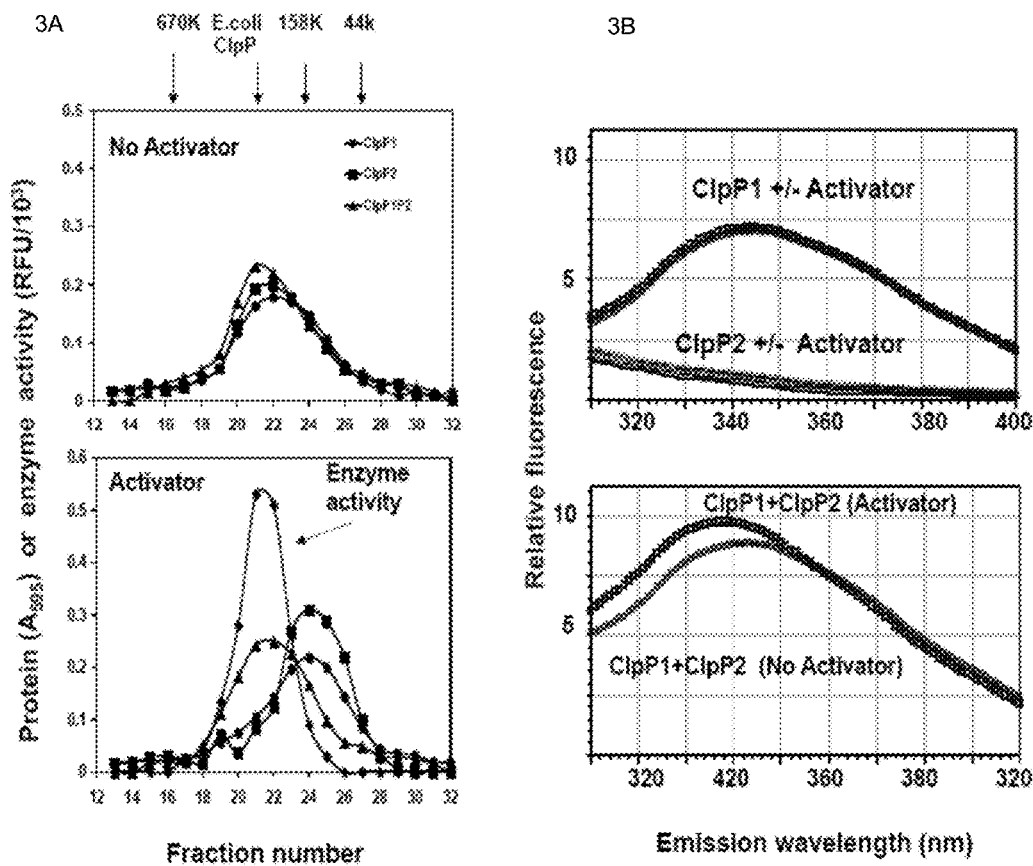
FIGS. 3A-3B demonstrate that with an activator present, ClpP1 and ClpP2 tetradecamers dissociate into heptamers but ClpP1/ClpP2 mixture forms an enzymatically active tetradecamer.

Mtb ClpP1 or ClpP2 genes were expressed as C-terminal fusions with 6xHis (SEQ ID NO: 26) and/or Myc tags under the control of a tetracycline-inducible promoter. Since previous efforts to produce active ClpP1 and ClpP2 in *E. coli* were unsuccessful (Benaroudj et al, 2011; Ingvarsson et al, 2007) ClpP1 and ClpP2 were separately expressed under conditions resembling those in Mtb by using the closely related nonpathogenic species *M. smegmatis*. Purification on a Ni-NTA agarose column yielded large amounts of nearly pure proteins, each with an apparent molecular weight of ~22 kDa (FIG. 1A). When ClpP1 and ClpP2 were subjected to gel filtration on a S-300 Sephacryl column, both were eluted as single homogenous peaks with a molecular mass of about 300 kDa (FIG. 3A, top panel). Thus, both ClpP1 and ClpP2 had the same elution profile as *E. coli* ClpP and appeared to be 14-subunit 2-ring complexes.

The ClpP1 and ClpP2 bands from the SDS PAGE were digested by trypsin and chymotrypsin and analyzed by MS/MS. Eighty-three peptides were identified for ClpP1 (92% coverage by amino acids) and 70 peptides for ClpP2 (94% coverage). Although mass spectrometry thus demonstrated nearly all the expected peptides, N-terminal sequencing indicated that ~70% of both proteins were N-terminally processed with major cleavage sites at $Asp^6$-$Met^7$ for ClpP1 and $Ala^{12}$-$Arg^{13}$ for ClpP2 (FIG. 1B). (In addition, minor cleavages were also detected at $Thr^5$-$Asp^6$ and $Met^7$-$Arg^8$ for ClpP1 and $Arg^{13}$-$Tyr^{14}$ for ClpP2.) It is noteworthy that the extent of this processing varied in different preparations and correlated with their ability to support enzymatic activity. Thus, N-terminal processing of both gene products appears important for the formation of the active enzyme. Moreover, when full-length mutant forms of ClpP1 and ClpP2, which lacked enzymatic activity (see below), were expressed in *M. smegmatis*, a much smaller fraction of N-terminally processed forms could be detected. Therefore, it is likely that the proteolytic processing of mycobacterial ClpPs occurs primarily through an autocatalytic mechanism (possibly involving collaboration with the *M. smegmatis* enzymes). Accordingly, ClpP1 is cleaved after Asp (FIG. 1B), which as shown below, is one of the preferred sites for MtbClpP (see below, Table 2).

In subsequent studies, the constructs were therefore expressed corresponding to the processed versions directly and more homogenous preparations were obtained with higher activities. It is noteworthy that these shorter forms, which do not require N-terminal processing, could also be efficiently produced in *E. coli*.

ClpP1 and ClpP2 Form a Mixed ClpP1P2 Protease that Requires Certain Short Peptides for Activation.

Neither ClpP1 nor ClpP2 alone had peptidase activity (FIG. 1C), although both formed tertadecameric structures characteristic of the ClpP family. Because both genes are essential (Ollinger et al, 2011; Raju, 2011, In Press; Sassetti et al, 2003), it was hypothesized that ClpP1 and ClpP2 are not two distinct enzymes, but instead associate to form a novel, mixed proteolytic complex. To test this possibility, it was first attempted to co-express Mtb ClpP1 and ClpP2 in *M. smegmatis*. The two proteins associated in vivo since they could be co-immunoprecipitated from the cell extract (see Example 2 herein). However, due to wide variations in the levels of ClpP1 and ClpP2 expression, the ratios between the co-purified ClpP1 and ClpP2 varied markedly in different preparations, and this heterogeneity prevented rigorous study of the active complex. Therefore, the subunits were expressed separately and reconstitution of a mixed complex from pure components was attempted. In fact, mixing pure ClpP1 and ClpP2 together in high concentrations (up to 0.5 mg/ml) resulted in the appearance of very low peptidase activity against the fluorogenic substrate of *E. coli* ClpP, Suc-Leu-Tyr-AMC.

During attempts to identify transition-state specific inhibitors of this low activity, the discovery that a group of N-blocked peptide aldehydes that were substrate analogs not only did not inhibit, but actually stimulated this activity over 1000 fold was made. A similar dramatic activation was even found with certain related blocked peptides. For example, as shown in FIG. 1C, a mixture of ClpP1 and ClpP2 was inactive in hydrolyzing the Z-Gly-Gly-Leu-AMC or the quenched fluorescent substrate Mca-GHQQYKMK-Dpa (Dnp)-amide amide (SEQ ID NO: 31), but in the presence of the activating peptide Z-Leu-Leu, both substrates as well as the unfolded protein, casein, were efficiently cleaved (FIGS. 1C-1D). The activating peptides and peptide aldehydes only induced peptidase activity if both ClpP1 and ClpP2 were present together. It is noteworthy that at 37° (under standard assay conditions used herein) the activation occurred without any noticeable delay after the addition of the peptide activator. Also, the activator had to be continually present for enzymatic activity. When the activator was removed by gel filtration or if its concentration was reduced by dilution, activity was lost, but it could be regained fully upon restoration of activator to its prior concentration (Table 3).

The strongest stimulation against Z-Gly-Gly-Leu-AMC, as well as other substrates, was found with Z-Leu-leucinal (Table 1, FIG. 2), but the longer aldehyde Z-Leu-Leu-leucinal was significantly less active. Several other hydrophobic dipeptide aldehydes (e.g. Z-Val-phenylalaninal), acidic peptide aldehydes (e.g. Z-Pro-Nle-aspartal) and alkyl aldehydes did not show any stimulatory capacity. The effective peptide aldehydes presumably should bind to at least some of the enzymes' fourteen active sites. However, the related peptide Z-Leu-Leu and its alcohol derivative Z-Leu-leucinol (which presumably should not bind strongly to the active sites) could also activate ClpP1P2, although only at much higher concentrations than the corresponding aldehydes. A much smaller stimulation was observed with blocked peptides Z-Leu, Z-Gly-Leu and Z-Gly-Leu-Leu (Table 1).

Figure 2:
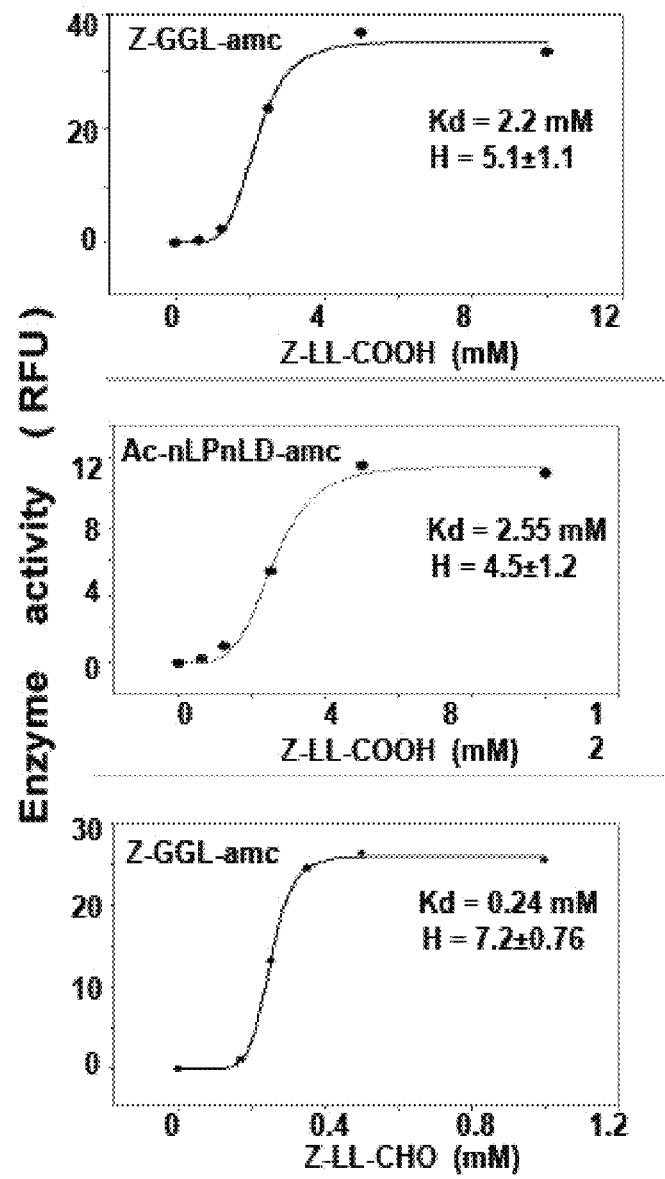
FIG. 2 demonstrates that certain short peptides and peptide aldehydes dramatically activate ClpP1P2 by binding to multiple sites. Determination of Hill coefficient of Z-Leu-Leu and Z-Leu-Leu-CHO in the hydrolysis of Z-Gly-Gly-Leu-amc and Ac-Nle-Pro-Nle-Asp-amc.

The concentration dependence for activation by, Z-Leu-leucinal (Kd=0.24 mM) and Z-Leu-Leu (Kd=2.2 mM), revealed a highly cooperative mechanism with a Hill coefficient of 5-7 (FIG. 2). Thus, multiple molecules probably bind to ClpP1P2 to stimulate its activity. Though substrate analogs, these activators are not cleaved, since upon incubation with ClpP1P2, no new amino groups could be detected using the sensitive fluorescamine assay. It is noteworthy that although the aldehyde had a higher affinity, at high concentrations, Z-Leu-Leu caused a greater activation than Z-Leu-leucinal (FIG. 2). Also because peptides are more stable and much less expensive than the corresponding aldehydes, in subsequent studies, we routinely induce Mtb ClpP1P2 activity using Z-Leu-Leu (referred to subsequently as the "activator").

Activation Involves Dissociation of ClpP1 and ClpP2 Tetradecamers and Formation of 2-Ring ClpP1P2 Complex.

Because the activators stimulate only ClpP1 and ClpP2 together (but not pure ClpP1 or ClpP2 (FIGS. 1C-1D), they probably activate by promoting the formation of a new mixed ClpP1P2 complex. How the presence of an activator affects the sizes of these different complexes was examined. Upon size exclusion chromatography, a mixture of ClpP1 and ClpP2 behaved as tetradecamers exactly like pure Mtb ClpP1 or ClpP2 and E. coli ClpP (FIG. 3A, upper panel). However, when the activator Z-Leu-Leu was present (FIG. 3A, lower panel), both ClpP1 and ClpP2 peaks were eluted as a single lower molecular weight peak, resembling in size β-globulin (150 kDa). Thus, the tetradecameric (presumably 2-ring) complexes composed of a single subunit type dissociated into heptamers. However, in the presence of the activator, the ClpP1/ClpP2 mixture was eluted as a 300 kDa peak that coincided with the peptidase activity and corresponded in size to ClpP tetradecamers (FIG. 3A, lower panel). The ClpP1P2 complexes were isolated from the peak using Ni-NTA (by His-tagged ClpP2) or anti-Myc (by Myc-tagged ClpP1) columns, and the presence of both proteins in resine-bound material was confirmed by MS.

Thus, the activating peptide causes the dissociation of ClpP1 and ClpP2 tetradecamers into heptamers and favors their subsequent association to form the active tetradecameric ClpP1P2 complex. By contrast, no changes in elution pattern were observed when E. coli ClpP was incubated with this activator.

Conformational Changes Accompanying Formation of ClpP1P2 Complex.

The dissociation and reassociation of multimeric ClpP1 and ClpP2 rings must involve activation-induced major changes in subunit conformation. Because ClpP1 (but not ClpP2) contains a Trp residue, it can be used to monitor conformational changes that may accompany the formation of an active ClpP1P2 complex from inactive ClpP1 and ClpP2 ones. Although no spectral changes were observed with dissociation of the ClpP1 tetradecamer upon addition of the activator, the formation of the active ClpP1P2 complex appears to involve changes in ClpP1's conformation, because the fluorescence of Trp174 in ClpP1 shifted its maximal fluorescence from 345 in pure ClpP1 to 338 nm. (FIG. 3B). Thus the interaction between ClpP1 and ClpP2 subunits leading to activation is associated with changes in subunits' conformation. It is noteworthy that similar changes in Trp174 fluorescence occurred when active-site mutants of ClpP1 and ClpP2 that lack enzymatic activity (see below) were mixed in the presence of the activator. Thus, enzymatic activity of both ClpPs is not necessary for their dissociation-reassociation and the major structural changes associated with this activation process.

To confirm that such a mixed ClpP1P2 complex actually exists in vivo, it was tested whether endogenous ClpP1 and ClpP2 associate in wild type M. smegmatis. As described in Example 2, mycobacterial recombineering was employed to add a C-myc tag to the C-terminus of genomic ClpP2. The C-myc-tagged ClpP2 was isolated together with associated proteins using an anti-myc resin, and the material eluted with the Myc peptide was resolved by SDS PAGE. Bands corresponding by size to ClpP2 and ClpP1 were analyzed by Mass Spectrometry, and the presence of both subunits was confirmed, indicating that mixed ClpP1P2 complexes are present in mycobacteria.

Mtb ClpP1P2 is Composed of One ClpP1 and One ClpP2 Heptameric Ring.

Figures 4A, 4B:
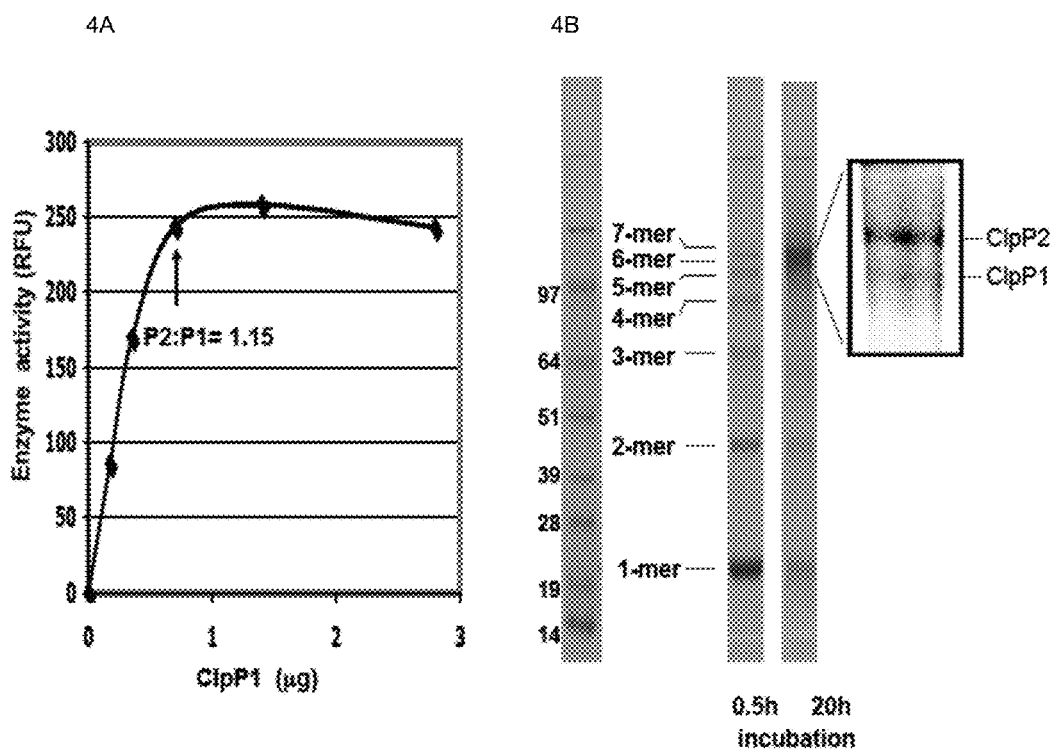
FIGS. 4A-4B demonstrate that ClpP1P2 has maximal activity at equimolar amounts of ClpP1 and ClpP2 and is composed of heptameric rings containing only ClpP1 or ClpP2 subunits.

To determine the subunit composition of this ClpP1P2 complex, the relative concentrations of ClpP1 and ClpP2 in the presence of an activator were varied (FIG. 4A). Upon increasing the amount of ClpP1 with a constant amount of ClpP2, peptidase activity gradually increased and reached its maximum when these components were present in close to equimolar amounts. Conversely, when ClpP1 content was held constant and the amount of ClpP2 increased, maximal activity was also obtained with equimolar concentrations. In different experiments using different ClpP1 and ClpP2 preparations, the optimal ClpP1/ClpP2 molar ratio ranged from 0.82 to 1.15. Thus, the active complex contains equal numbers of ClpP1 and ClpP2 subunits.

These findings and the rapidity of activation together strongly suggest that the active enzyme is composed of one ClpP1 and one ClpP2 ring. However, it is also possible that each heptameric ring contains a mixture of ClpP1 and ClpP2 subunits, as has been found for the cyanobacterium Synechococcus ClpP complexes (Andersson et al, 2009; Stanne et al, 2007). To determine the composition of the rings, the neighboring subunits in the active ClpP1P2 tetradecamer were cross-linked with glutaraldehyde in the presence of the activator (FIG. 4B). After a 0.5 hr of incubation, seven distinct cross-linked bands were evident on SDS PAGE corresponding to 1-, 2-, 3-4-, 5-, 6-, and 7-mers. As expected, the larger cross-linked structures were the least abundant. After an overnight incubation, when cross-linking went to completion, all 7 subunits, presumably comprising the rings, were cross-linked together, but still no band was observed with a molecular mass higher than that of a 7-mer. Thus, apparently, no cross-linking occurred between the two rings (which presumably requires a cross-linker with a longer spacer arm than glutaraldehyde). Analysis by mass spectrometry indicated that the cross-linked heptamers were composed only of ClpP1 or of ClpP2 subunits respectively and no peptides corresponding to ClpP1-ClpP2 cross-linked were found. Thus, each hepatmeric ring in the Mtb ClpP1P2 protease is homogenous in composition.

Substrate Specificity of Mtb ClpP1P2.

To define the substrate preference of the ClpP1P2 active sites, a variety of synthetic fluorescent peptides with hydrophobic, acidic, or basic residues in the P1 position were tested (Table 2). The best substrate was Z-Gly-Gly-Leu-AMC, while Suc-Ala-Ala-Phe-AMC and Ala-Ala-Phe-AMC also were readily cleaved. The failure of ClpP1P2 to degrade rapidly the widely used proteasome substrate Suc-Leu-Val-Tyr-AMC indicates major differences from enzymes in the mammalian cytosol. It is noteworthy that Z-Leu-Leu-AMC, the fluorescent peptide corresponding to the peptide activator employed routinely Z-Leu-Leu, was a poor substrate for the enzyme (Table 2), and conversely the peptides corresponding to the best substrates, Z-Gly-Gly-Leu or Z-Gly-Leu, were poor as activators (Table 1).

In addition to hydrophobic peptides, ClpP1P2 also efficiently hydrolyzes a peptide with acidic residues in the P1 position, Ac-Nle-Pro-Nle-Asp-AMC. (this substrate is degraded by E. coli ClpP, which had been reported to cleave after aspartate residues in model polypeptides (Thompson & Maurizi, 1994); data not shown). However, Mtb ClpP1P2 did not hydrolyze Z-Leu-Leu-Glu-AMC or peptides with basic P1 residue and was also inactive against a variety of unblocked amino acid-AMC substrates used to assay aminopeptidases (Table 2). ClpP1P2 also could cleave a variety of longer quenched fluorescent peptides (e.g. Mca-GNTQFKRR-Dpa(Dnp)-amide (SEQ ID NO: 27), Mca-GHQQYAMK-Dpa(Dnp)-amide (SEQ ID NO: 28), Mca-GNQQYKMK-Dpa(Dnp)-amide (SEQ ID NO: 29) and Mca-KKPTPIQLN-Dpa(Dnp)-amide (SEQ ID NO: 30)), and could degrade slowly the largely unstructured protein FITC-casein, provided an activator was present (FIG. 1D).

Though ClpP1 or ClpP2 Alone Lack Enzymatic Activity, their Catalytic Triads are Formed.

The sequences of both ClpP1 and ClpP2 appear to contain a Ser/His/Asp catalytic triad characteristic of serine proteases (FIG. 1B). Accordingly, Mtb ClpP1P2 was sensitive to most standard inhibitors of serine proteases (FIG. 5A), including agents that react with the active site serine (dichloroisocoumarin (Powers & Kam, 1994) and biotinylated derivative of fluoroethoxiphosphynil (FP-biotin) (Liu et al, 1999)), and peptide chloromethyl ketones (Szyk & Maurizi, 2006), which modify the catalytic histidine. By contrast, standard inhibitors of metalloproteases and cysteine proteases had no effect. Interestingly, the hydrolysis of both hydrophobic and acidic substrates was inhibited to similar extents by the peptide chloromethyl ketones, Z-LY-CMK or AAF-CMK.

To learn whether both gene products are enzymatically active in the complex, ClpP1, ClpP2 and the ClpP1/ClpP2 mixture were incubated with the biotinylated covalent modifier of active-site serines. As shown in FIG. 5B, ClpP1 and ClpP2 subunits were both covalently modified even in the enzymatically inactive ClpP1 or ClpP2 complexes. Thus, the catalytic triad appears functional in these complexes despite their lack of enzymatic activity. To test the possibility of a non-specific binding of biotinylated modifier, the mutant forms of ClpP1 or ClpP2 with active site Ser substituted for Ala were incubated with FP-biotin. As shown in FIG. 5B, no incorporation of the modifier in the mutant proteins occurred, thus confirming its specific reaction with the active sites.

It was possible that the activator would enhance the modification of the active-site serines by promoting active site formation. However, the presence of the activator did not stimulate the modification of either homogeneous ClpP1 or ClpP2 or the mixed complex. In fact, the activator even reduced slightly (but reproducibly) this reaction, as also occurred in the presence of a substrate. Similar inhibition was observed in the presence of a substrate. Thus some activator molecules, which are structurally related to peptide substrates, appear to bind to the active sites. In any case, because active site labeling occurred with ClpP1 and ClpP2 alone, these results prove that activation is not through formation of the catalytic triad, and instead that formation of the mixed tetradecamer probably enables the substrate to access and bind to the previously latent active sites.

ClpP1 and ClpP2 have Distinct Cleavage Specificities.

To estimate how ClpP1 and ClpP2 subunits contribute to enzymatic activity of the complex, pure ClpP1 or ClpP2 was inactivated by pretreatment with dichloroisocoumarin at concentrations that completely inhibit ClpP1P2. When the covalently inactivated ClpP1 or ClpP2 was incubated with its normal counterpart plus activator, the hydrolysis of hydrophobic and acidic peptide substrates, as well as casein, was significantly less than with untreated subunits (FIG. 5C). Thus, both types of subunits appear to function enzymatically and contribute to the activity of the complex. However, inactivation of ClpP1 caused a much greater loss of these activities than did inactivation of ClpP2, especially with the hydrophobic peptide substrate (FIG. 5C).

To confirm these different roles of each subunit, enzymatic complexes were reconstituted using wtClpP1 and an active-site mutant ClpP2 (Ser$^{110}$ to Ala) or with wtClpP2 and active site mutant ClpP1 (Ser$^{98}$ to Ala). The complexes containing only one type of active subunits showed lower peptidase activity than the wild type enzyme against both hydrophobic and acidic peptide substrates, and casein (FIG. 5C). As was found upon derivatization with isocoumarin, the lack of functional ClpP1 caused a greater loss of activity against these various substrates than did the loss of ClpP2, particularly with the hydrophobic substrate. These data indicate that ClpP1 and ClpP2 active sites have different substrate preferences and suggest that ClpP1 sites are more important than ClpP2's in cleaving the most abundant bonds in proteins.

The ClpC1 ATPase Complex Stimulates Protein Degradation by ClpP1P2 but Only in the Presence of Both an Activator and ATP.

Figures 13A, 13B, 13C, 13D:
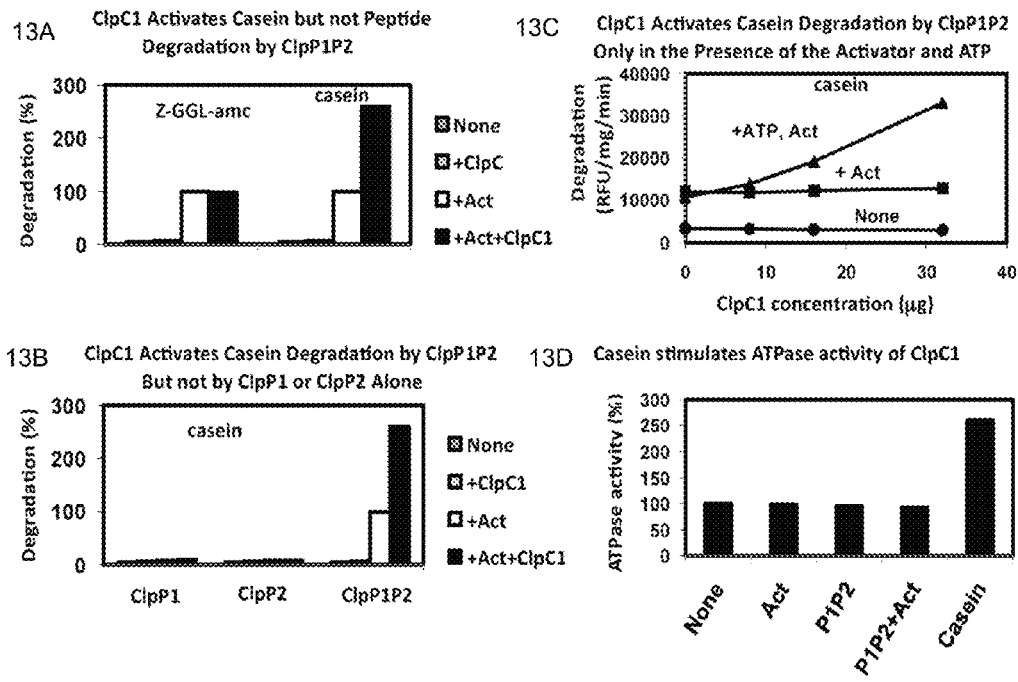
FIGS. 13A-13D demonstrate that ClpC1 activates degradation of casein, but not peptides, by ClpP1P2 only in the presence of activator and ATP.

The mechanism for the dramatic ClpP1P2 activation by small peptides uncovered here was surprising and unprecedented. One attractive possible mechanism would be that the conformational changes and complex formation induced by the activator resemble those changes caused by the binding of the Mtb regulatory ATPase complex, ClpC1 or ClpX, since in some ATP-dependent proteases (e.g. human mitochondrial ClpP), no peptidase activity was demonstrated in the absence of nucleotides and the regulatory ATPase. To address the possibility that the peptide activator mimicked the regulatory ATPases, the ClpC1 ATPase from Mtb was cloned, expressed in M. smegmatis, and tested to determine whether it can stimulate ClpP1P2 activity. As expected, the resulting complex was of high molecular weight and had ATPase activity. Unlike the dipeptide activator, addition of ClpC1 did not increase the hydrolysis of any of various fluorescent peptides assayed, nor did it enhance the effect of the activator on their degradation (FIG. 13A). However, when the ATPase was added in the presence of the activator, it markedly increased the degradation of the model protein, FITC-casein (FIG. 13A). This stimulation of protein degradation by ClpP1P2 was only observed when both the activator and ATP were present (FIG. 6C). Thus, ClpC1 and the activator must increase proteolysis by quite different, but clearly additive mechanisms.

It is noteworthy that ClpC1 did not stimulate proteolysis by ClpP1 or ClpP2 alone (FIG. 13B). Therefore, it is very likely that ClpC1 in vivo also functions only with the mixed ClpP1P2 complex and requires an additional factor resembling the activator for protein degradation. The peptide activator did not influence ATP hydrolysis by ClpC1. By contrast the protein substrate casein stimulated ClpC1's ATPase activity 2-fold (FIG. 13D) in a similar fashion to the activation by substrates of the homologous *E. coli* AAA ATPases, Lon (Waxman & Goldberg, 1982), ClpA (Hwang et al, 1988; Thompson & Maurizi, 1994) and HslU (Seol et al, 1997). Thus the peptide activator is necessary only for ClpP1P2 assembly, while ClpC1 binds casein directly and facilitates its degradation by ClpP1P2.

Discussion

Mtb ClpP1P2 is a Novel Enzyme Complex in Multiple Respects.

Several observations led to the hypothesis that ClpP1 and ClpP2 function together in a single complex. 1) initial attempts and those of others (Benaroudj et al, 2011; Ingvarsson et al, 2007) to isolate active ClpP1 or ClpP2 from Mtb were unsuccessful, even though they formed tetradecameric complexes similar in size to other ClpP family members, as shown in FIGS. 3A-3B and by others (Ingvarsson et al, 2007). 2) As shown in Example 2, clpP1 and clpP2 genes are both essential for growth and infectivity of Mtb, and thus, they cannot compensate for the loss of the other. 3) When ClpP1 and ClpP2 were co-expressed in *M. smegmatis*, they could be co-immunoprecipitated (see Example 2). Demonstrated herein is that neither purified ClpP1 nor ClpP2 alone is enzymatically active, but if they are both present, together with an activating peptide or peptide derivative, then mixed complexes are formed that show robust proteolytic activity. Furthermore, only when the mixed ClpP1P2 complex was formed in the presence of the activator, was casein degradation stimulated in an ATP-dependent manner by ClpC1 ATPase. Since this latter process resembles the conditions for protein degradation in vivo and since ClpC1 is also essential for viability, it seems very likely that the ClpP1P2 is the functional protease in vivo.

One initial approach that enabled the production of active ClpP1P2 was the use of an unusual expression system. Expressing the cloned Mtb ClpP1 and ClpP2 proteins in *E. coli* did not yield the mature, processed subunits, although some, limited processing of Mtb ClpP1 and ClpP2 (by ClpP1) has been recently reported in *E. coli* (Benaroudj et al, 2011). In the present studies, the closely related *mycobacterium, M. smegmatis*, was used, in which ClpP1 and ClpP2 underwent efficient N-terminal processing, which appears necessary for enzymatic activity. (Benaroudj et al, 2011). In fact, in the crystal structure of the inactive ClpP1 tetradecamer composed of unprocessed subunits, the distance between the active site Ser and His residue was too large to support the formation of the active catalytic triad (Ingvarsson et al, 2007). Once the the N-termini of the fully active ClpP1 and ClpP2 was identified, these shorter sequences were directly expresses, which yielded homogenous tetradecamers in *M. smegmatis* as well as in *E. coli*. Also, by using an *E. coli* mutant lacking endogenous ClpP, WT or mutant ClpP1 and ClpP2 was obtained without contamination by endogenous ClpP subunits. It is noteworthy that these ClpP1 tetradecamers composed only of "processed" subunits do contain a functional catalytic triad, although it is still unable to catalyze peptide hydrolysis. Such a lack of catalytic activity despite the presence of a functional catalytic triad has been previously shown for other pro-enzymes, such as trypsinogen, which though enzymatically inactive can react with various active site titrants (Smith et al, 1992). Its lack of enzymatic activity is attributed to an inability of substrates to access the active sites, and presumably a similar explanation accounts for the inactivity of pure ClpP1 and ClpP2 (see below).

Recently, Mtb ClpP2 and ClpC1 were reported to catalzye the degradation of an endogenous Mtb protein Rse A (Barik et al, 2010). While degradation of that substrate perhaps may not require formation of a ClpP1P2 complex (unlike casein or the peptides studied here), several features of that study are difficult to reconcile with our findings. For example, they expressed Mtb ClpP proteins in *E. coli*, which the inventors and others (Benaroudj et al, 2011; Ingvarsson et al, 2007) found to yield mostly non-processed inactive tetradecamers. Possibly, their use of WT *E. coli* for expression may have resulted in contamination by the highly active *E. coli* ClpP, as was reported by Benaroudj et al (Benaroudj et al, 2011). To avoid these problems, the mature Mtb proteins used herein were expressed only in *E. coli* strain lacking ClpP.

Very little is known about ClpP proteases from organisms that contain multiple clpP genes. In *Streptomyces lividans*, five clpP genes are organized in two operons (clpP1 and clpP2; clpP3 and clpP4), and one is monocistronic (Viala & Mazodier, 2002). Both ClpP1 and ClpP2 are required for degradation of the transcriptional activator PopR, which suggests that they also form a single mixed complex (Viala & Mazodier, 2002). ClpP3 and ClpP4 can also function together in PopR degradation, and their coordinate regulation suggests that they also comprise a mixed complex (Viala & Mazodier, 2002). In plant organelles, the organization of the ClpP proteases is much more complex (Peltier et al, 2004; Peltier et al, 2001); for example, tetradecameric ClpP complexes have been isolated from *Arabidopsis thaliana* that contain 5 different ClpP proteins and 6 different non-proteolytic ClpP homologs (ClpR) (Peltier et al, 2004). Although their composition and activities have not been studied, the different ClpP and ClpR proteins may be present in the same tetradecameric complex (Peltier et al, 2004). In fact, a novel form of ClpP has recently been characterized from the cyanobacterium *Synechococcus* that contains two identical heptameric rings, composed of three active ClpP3 and four inactive ClpR subunits (Andersson et al, 2009), which though inactive, are essential for the ClpC-dependent proteolytic activity.

The cross-linking experiments described herein demonstrate that Mtb ClpP1P2 heptameric rings are composed of seven identical subunits. Therefore, the active Mtb enzyme must be composed of one ClpP1 ring and one ClpP2 ring. Accordingly, optimal activity was obtained when ClpP1 and ClpP2 were present in a 1:1 molar ratio (FIG. 4A). This association of the ClpP1 and ClpP2 rings with each other causes conformational changes that allow both complimentary rings to become enzymatically active. By monitoring the changes in tryptophan fluorescence in ClpP1 that accompany activation, it was confirmed herein that the active ClpP1 conformation is achieved only in the presence of ClpP2 and a dipeptide activator. Interestingly, the ClpP1 and ClpP2 rings can activate each other, even if either or both were inactivated by mutation or derivatization of their active site serines.

Although only a limited number of peptide substrates were screened, Mtb ClpP1P2 clearly has a rather broad substrate specificity. In its preference for large hydrophobic residues in the P1 position, ClpP1P2 resembles chymotrypsin; however, it also cleaves a peptide with an acidic residue in the P1 position that is a typical substrate for caspases and the caspase-like site on the proteasome (Kisselev et al, 2006; Kisselev et al, 2003). The active sites on ClpP1 and ClpP2 clearly differ in their cleavage specificity. ClpP1 clearly is predominant in the hydrolysis of casein and after hydrophobic residues (which are highly abundant in cell proteins). Its loss also reduces the rate of hydrolysis of acidic peptides but ClpP2 rings also contribute significantly to this activity.

Activation of ClpP1P2 by Small Molecules.

The most unexpected and novel aspect of these findings is the discovery of small molecules that dramatically activate ClpP1P2 and enable it to degrade even unstructured polypeptides. In vitro, these agents were essential for both the appearance and the maintenance of enzyme activity. The most potent among these activators are short N-blocked peptide aldehydes, but the corresponding peptide alcohols and peptides also stimulate, though at higher concentrations (Z-Leu-Leu was used routinely here because it is inexpensive and yields the largest maximal activation.) All these compounds markedly stimulate hydrolysis of all peptide substrates tested, as well as casein. In fact, without this surprising finding, the remaining observations on ClpP1P2 would not have been possible because its inherent activity is too low for most studies.

Even though ClpP1 and ClpP2 were enzymatically inactive by themselves, their active sites, even in the absence of the activator, could react with agents that covalently modify active site serines or histidines, and did so as strongly as in the active enzyme (FIG. 5B). Thus, in the absence of activator, the catalytic triads appear to be functional in ClpP1 and ClpP2, unlike in the unprocessed ClpP1 (Ingvarsson et al, 2007). Presumably these sites are unable to hydrolyze peptides in the absence of the complementary ring, because of a failure of the substrate to enter the pure ClpP1 and ClpP2 complexes, as occurs with the latent form of the 20S proteasome, which is activated by a gating mechanism allowing substrate entry (Smith et al, 2007). Alternatively formation of the mixed complex may involve structural rearrangements that enable catalysis.

The exact site where the activator binds to ClpP1P2 remains uncertain, and several possibilities exist. The structures of the activators closely resemble those of some hydrophobic substrates (Table 1, Table 2), which suggests that the activators bind to the active sites. Accordingly, peptide aldehydes, which should bind tightly to active site serine, were the strongest activators, while related peptides (which resemble products of substrate cleavage) are about 10-times less potent. Another observation supporting binding to the active sites was that the addition of activators instead of increasing enzyme interaction with the active-site titrant, actually decreased the extent of this modification. Because the structural changes that accompany ClpP1P2 activation (dissociation of tetradecamers into heptamers, formation of mixed complexes and changes in Trp fluorescence) were also induced by the activator in the inactive ClpP1 and ClpP2 active site mutants, these activating dipeptides do not require interaction with the catalytic serines to induce dissociation-reassociation.

Although agents that bind to the active sites should be competitive inhibitors if they bind to all the active sites, in the tetradecameric HslV protease complex from *E. coli*, Chung and coworkers have shown that inactivation of about half the proteolytic sites can occur without a decrease in maximal proteolytic rate (Lee et al, 2009). Thus, in Mtb ClpP1P2 partial occupancy of active sites by activators probably could occur without reducing activity, while also perhaps inducing conformational changes in remaining subunits that favor formation of the active state. To induce these structural changes, the activators exhibit very strong cooperativity with a Hill coefficient between 5 and 7, which suggests that multiple molecules bind to either a fraction of the active sites (or to a distinct allosteric site) to induce the active conformation.

Although these activators resemble peptide substrates, there does not appear to be a simple correspondence between sequences that are preferentially hydrolyzed and ones that support activation. Peptides corresponding to the peptide activators were poor substrates for the enzyme (Table 2), and conversely the peptide corresponding to the best substrate was poor as an activator. Thus it is possible that these peptides activate by also binding to an additional regulatory site.

The active sites of the cylindrical proteases, such as ClpPs, HsUV, or proteasomes, are sequestered within the proteolytic chamber and by themselves cannot degrade protein substrates (Baumeister et al, 1998; Striebel et al, 2009; Yu & Houry, 2007). Activation of these compartmentalized proteases can occur if the binding of the ATPase alters the conformation of the active site as in HslUV system (Huang & Goldberg, 1997; Sousa et al, 2002; Yoo et al, 1996; Yu & Houry, 2007) or opens an entry channel to allow substrate access, as occurs in gating of proteasome (Groll et al, 2000; Rabl et al, 2008; Smith et al, 2007; Whitby et al, 2000) and proteases ClpXP or ClpAP (Grimaud et al, 1998; Kirstein et al, 2009; Lee et al, 2010b; Maurizi et al, 1998). The latter mechanism is important in action of acyldepsipeptide antibiotics, which are cytotoxic in *B. subtilis* and *E. coli* (Brotz-Oesterhelt et al, 2005; Kirstein et al, 2009) by causing activation of ClpP and excessive degradation of cellular proteins (Kirstein et al, 2009; Lee et al, 2010a). These molecules bind to the two ends of the ClpP tetradecamer in the cavities between adjacent ClpP monomers, which are the same sites to which loops of the regulatory ATPases bind (Bewley et al, 2006; Kim et al, 2001; Lee et al, 2010a; Lee et al, 2009). Thus, the acyldepsipeptides stimulate proteolysis by facilitating substrate access to the degradative chamber (Kirstein et al, 2009; Lee et al, 2010a), and prevent association of the protease with regulatory ATPases. (Kirstein et al, 2009; Lee et al, 2010a) Recently, additional activators have been identified that function by a similar mechanism (Leung et al, 2011).

Without wishing to be bound by theory, one initially attractive possible mechanism of the dipeptide activators described herein was that they function in a similar fashion as acyldepsipeptide antibiotics. However, the dipeptide activator and ClpC1 ATPase have very different effects on peptide degradation, and stimulation of casein degradation requires the presence of both an activator and ClpC1. Furthermore, in related studies using acyldepsipeptide ADEP2, the inventors found that these agents also can activate Mtb ClpP1P2 only in the presence of an activating peptide. It is therefore highly unlikely that the activator binds to the same regulatory cavities as ClpC1 or the ADEPs.

Without wishing to be bound by theory, the finding that ClpC1 functions only in the presence of a small molecule activator suggests that factors with similar activity exist in Mtb and allow ClpP1P2 association and function with ClpC1. In this respect, these activating dipeptides resemble a protein or "chemical" chaperone that prevents formation of inactive conformations and favors formation of the active enzyme. However, unlike a chaperone, the dipeptide activators, have to be continuously present to maintain the active ClpP1P2 complex. These findings imply that Mtb contains endogenous activators, either small molecules or perhaps protein(s), that promote the formation and the maintenance of ClpP1P2 mixed tetradecamers in vivo.

Figure 6:
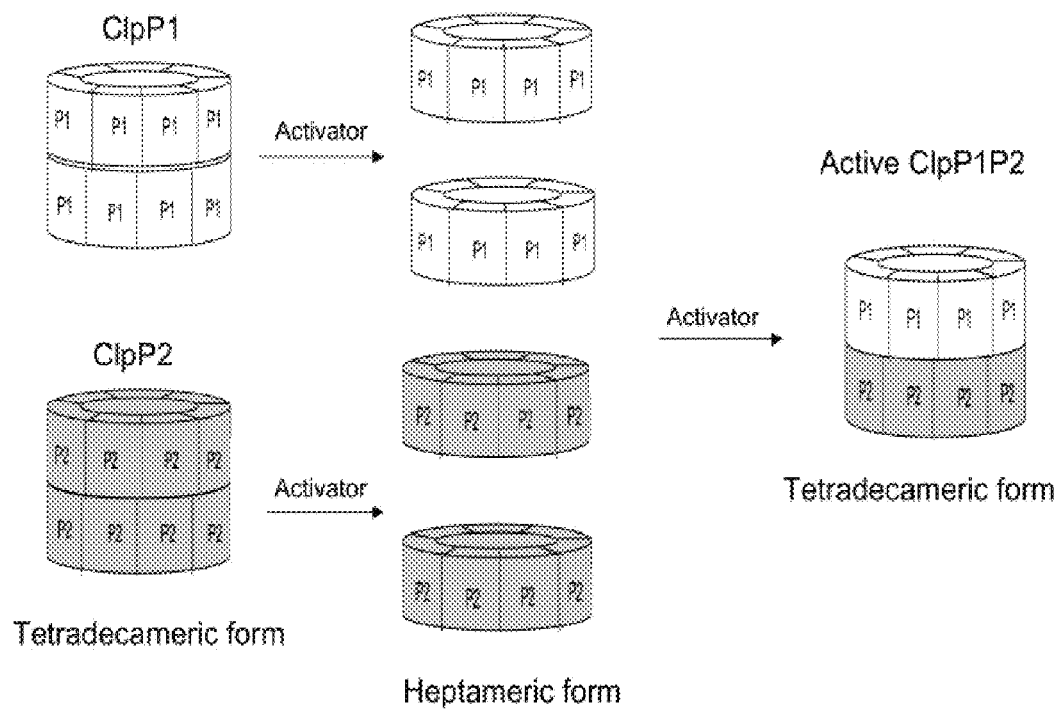
FIG. 6 depicts the mechanism of formation of functionally active ClpP1P2. The proposed mechanism is based on results in FIGS. 4A-4B showing that the optimal activity of ClpP1P2 is reached at the equal molar amounts of ClpP1 and ClpP2.

In human mitochondrial ClpP (unlike *E. coli* ClpP), the ClpX ATPase complex is necessary not only for substrate recognition and translocation, but also for the formation of the ClpP tetradecamers from inactive heptamers (Kang et al, 2005). This action resembles the second stage in the activation mechanism demonstrated here (FIG. 6). However, ClpC1 was unable by itself to induce activation of the Mtb enzyme. In Mtb, the expression of ClpC1 is regulated coordinately with ClpP1 and ClpP2 by ClgR factor (Sherrid et al, 2010); therefore it is very likely that ClpP1P2 functions in vivo together with ClpC1. Consequently, the finding described herein that ClpC1 ATPase promotes the degradation of casein only in the presence of an activator argues strongly that the activator serves a unique, essential function, and that in Mtb some endogenous factor serves a similar role in promoting assembly of the mixed complex.

ClpP1P2 is an Attractive Drug Target.

The present findings and our related in vivo observations (see Example 2) provide strong evidence that inhibition of ClpP1P2 is a promising new approach to combat tuberculosis. Not only is ClpP1P2 essential in Mtb, but no similar proteolytic complex exists in the mammalian cytosol, and its cleavage specificity, as defined with model peptides, clearly differs from those of the major mammalian cytosolic proteases (proteasomes). Furthermore, Mtb ClpP1P2 in structure and substrate specificity differs considerably from known ClpP family members in the mitochondria. Also, despite its unusual activation mechanism, ClpP1P2 is sensitive to typical inhibitors of serine proteases. It also seems likely that agents that activate Mtb ClpP1P2 may have therapeutic applications, since acyldepsipeptide antibiotics are toxic in many bacteria by activating ClpP and causing excessive proteolysis (Kirstein et al, 2009). Additionally, regulatory ATPases may also represent therapeutic targets.

Experimental Procedures

Materials.

Synthetic peptide substrates with C-terminal amc group and protease inhibitor were from Bachem (Switzerland), Sigma (USA) and Biomol International (USA). Peptide substrates for FRET assay, FITC-casein and glutaraldehyde were from Sigma (USA). Ni-NTA agarose and Sephacryl S-300 were from Qiagen and Pharmacia respectively. Black 96 wells micro plates used for enzyme assay were from Greiner (Germany). FP-Biotin (10-(fluoroethoxyphosphinyl)-N-(biotinamidopentyl)decanamide) was kindly provided by Dr. Francesco Parlati, Proteolix Inc.

Bacterial Strains, Plasmids, Expression and Growth of Cells.

*M. smegmatis* mc2155 were grown at 37° C. in Middlebrook 7H9 broth with 0.05% Tween 80 and ADC (0.5% BSA, 0.2% dextrose, 0.085% NaCl, 0.003 g catalase/1 L media) supplemented with hygromycin (50 μg/mL) and in case of inducible expression, with anhydrotetracycline (100 ng/mL). Full-length C-terminally 6xHis- (SEQ ID NO: 26), Myc- or 6xHis (SEQ ID NO: 26) and Myc tagged ClpP1 and ClpP2 proteins were expressed in *M. smegmatis* on pMV plasmid under the regulation of a constitutive GroEL promoter. For expression of shorter forms corresponding to processed ClpP1 (lacking 6 N-terminal amino acids) and ClpP2 (lacking 11 N-terminal amino acids), pTetOR plasmid, which has an inducible tetracycline promoter was used. After overnight induction with ATc (100 μg), cells were collected and kept −70° C.

Purification of Mtb ClpP1 and ClpP2.

All procedures of purification were done at 4° C. using the following buffers: Buffer A: 50 mM potassium phosphate buffer pH 7.6 containing 100 mM KCl, 5 mM MgCl2 and β-mercaptoethanol and 10% glycerol; Buffer B: 50 mM potassium phosphate buffer pH 7.6 containing 100 mM KCl, 5 mM MgCl2 and 5% glycerol. In a typical purification, frozen cells (5-10 g) of ClpP1 or ClpP2 were suspended in two volume of buffer A and broken by French press at 1500 psi. The obtained extract was centrifuged at 100,000×g and mixed with 5 ml Ni-NTA agarose previously equilibrated in buffer A. After gently shaking for 4 h, Ni-NTA agarose resin was transferred to empty column and proteins were eluted using step gradient ((0, 25, 50, 100 and 200 mM) of imidazole in buffer B. The fractions containing near homogeneous ClpP1 or ClpP2 proteins were combined, concentrated on Millipore MWCO 10,000 cut filter and purified further by gel filtration on Sephacryl S-300 column (1.5×12 cm) equilibrated in buffer B. High molecular weight protein peaks were combined, concentrated to ~3 mg/ml and kept at −70° C. The column was calibrated with Bio Rad molecular weight standards: thyroglobulin—670 kDa☐☐β-globulin—158 kDa and ovalbumin, and *E. coli* ClpP.

Determination of Enzyme Activity.

All assays were performed at 37° C. in 96 wells plate using Plate Reader SpectraMax M5 (Molecular Devices, USA). Wells contained 0.1 mM fluorescent peptide, 1-5 μg ClpP1P2, 0.5 mM Z-Leu-Leu-aldehyde or 5 mM ZLeu-Leu in 80 μl of 50 mM phosphate buffer pH 7.6 containing 5% glycerol, 100 mM NaCl. After shaking the samples for 20 sec, peptidase activities were assayed at 37° C. by continuously monitoring the rate of production of fluorescent 7-amino-4-methylcoumarin (amc) from fluorogenic peptide substrates at 460 nm (Ex at 380 nm). Cleavage of longer octa- and nano-peptides were measured using FRET assay using the conditions as above only quench substrates used were 2-5 μM and enzyme was 0.5-2 μg. Increase the fluorescence was monitored continuously at 405 nm (Ex at 340 nm). For measurement of FITC-casein degradation the substrate was purified using PD-10 column. Hydrolysis of 2-5 μg casein continuously monitored at 518 nm (Ex at 492 nm) All assays were performed in triplicate format and average results were presented. Deviations for amc and quench peptide substrate were less than 5% while in the case of FITC-casein it was less than 10%). Potential cleavage of enzyme activator Z-Leu-Leu was tested by fluorescamine method as described previously (Akopian et al., 1997).

ATPase activity of ClpC1 was measured in the buffer containing 50 mM TrisHCl pH 7.8, 50 mM KCl, 10% glycerol, 1 mM DTT, 2 mM ATP, 8 mM MgCl$_2$ The amount of generated orthophosphate was measured colorimetrically by Malachite Green method (Baykov et al, 1988). The deviation between the measurements was less than 5%.

Fluorescent Emission Spectra.

Emission spectra of ClpP1 and its complexes were performed in buffer B in micro plate format using SpectroMax M5 (USA) plate reader with a step of 1 nm. Preliminarily spectra registration indicated the max of excitation of Trp178 in ClpP1 environment is 279 nm in buffer B.

MS and N-Terminal Analysis.

Protein bands from SDS PAGE were digested by sequence grade trypsin (Promega) or chymotrypsin (Roche). Obtained peptides were analyzed by Thermo Electron LTQ-Orbitrap MassSpec after their separation by Agilent 1100 HPLC system. Automatic N-terminal sequencing of purified proteins (Edman degradation) was done using ABI 494 Protein Sequencers after transfer of proteins to PVDF membranes.

Cross Linking of Subunits.

Cross linking of ClpP1P2 was carried out with 0.125% glutaraldehyde in the buffer B containing activator Z-Leu- Leu. After 0.5 h and 20 h incubation at room temperature the reaction mixture was resolved by SDS PAGE, and proteins analyzed by MasSpec.

Plasmids.

For complementation studies, wildtype Mtb ClpP1 and ClpP2 were amplified from H37Rv genomic DNA by PCR, using primers RMR01-RMR04 in Table 6, and ligated into the constitutively expressing plasmid pMV762zeo. C terminal 6X his (SEQ ID NO: 26) or c-myc tags were added by PCR primers RMR05-RMR08 on Mtb ClpP1 and ClpP2 and recombined into the ATc inducible vector pTet using gateway recombination (Clontech). Site directed mutagenesis of ClpP1 and ClpP2 was carried out as described previously to generate various catalytic mutants used in the study. Catalytically inactive mutants were inserted into the ATc inducible vector pTet using gateway recombination. Processed Clp mutants were cloned into pTet or pMV762 vectors using primers listed above. The fusion GFP-SsrA was amplified from GFPmut3 wildtype DNA and cloned into pMV762zeo using primers RMR09-RMR12. Details of other plasmids used in this study can be found in Table 5.

Creation of Clp Knockdown Strains.

Mycobacterial recombineering was employed, as described previously (van Kessel and Hatfull, 2007), to create strains ptet_clpP1P2 and clpP2_ID. For strain ptet_clpP1P2, the tetracycline promoter, tetracycline repressor, and a hygromycin resistance marker were inserted into p96863 (Genscript). Both upstream and downstream of the insertion site, p96863 contained 200 bp fragments flanking either side of the native clpP promoter. A linear PCR product containing the regions of homology, the hygromycin resistance marker, and tetracycline repressor and promoter was generated using primers RMR13 and RMR14. Allelic exchange of the native promoter was carried out by transformation of this linear substrate into a Msm strain expressing mycobacteriophage recombinases gp60 and gp61 on a nitrile inducible, counter-selectable episomal plasmid. Counter selection on 10% sucrose led to loss of the recombineering plasmid. Successful integration of the desired sequence was confirmed by PCR, using primers RMR13 and RMR16. As RMR16 lies outside of the homology region used for recombineering, specific integration into the endogenous chromosome could be verified (FIG. 11B).

To create strain clpP2_ID, a linear DNA substrate was created in a similar fashion. The inducible degradation tag was inserted into p54689 (Genscript). Both upstream and downstream of the insertion site, p54689 contained 200 bp of homology to the C terminal end of clpP2 and the 3'-UTR of clpP2, respectively. A linear PCR product containing this homology and the inducible degradation tag was generated using primers RMR15 and RMR16. This PCR product was transformed into Msm as described above. Successful integration of the desired sequence was confirmed by PCR, using primers RMR13 and RMR16. As RMR13 lies outside of the homology region used for recombineering, specific integration into the endogenous chromosome could be verified (FIG. 11B).

To make the clpP2_ID strain, the tetracycline promoter and ClpP1 were inserted into the suicide plasmid, pSES. Constructs were electroporated into a Msm strain containing an integrated pMC1s vector constitutively expressing the tetR repressor (Ehrt et al., 2005). Integrants were screened by PCR using primers RMR17 and RMR18.

Inducible Degradation of ClpP2.

Mycobacterial recombineering was employed to insert the inducible degradation tag (ID-tag) directly downstream of the clpP2 open reading frame. Inducible degradation was performed as described previously. Briefly, strain clpP2_ID was transformed with an anhydrotetracycline inducible integrated plasmid carrying the HIV-2 protease. Stationary phase cultures were diluted 1000-fold, and induced with ATc (50 ng/mL). Cleavage by HIV-2 protease and subsequent protein degradation was monitored by epitope tags that flanked the ID-tag. To assess the role of the mycobacterial SsrA-tag, a constitutively expressing plasmid bearing GFP-SsrA was electroporated into clpP2_ID. Cultures were grown and induced as above, and increase in GFP upon HIV-2 protease induction was monitored by fluorescence (emission/excitation: 485/520) and by western blotting using anti-GFP.

REFERENCES

1. Akopian, T. N., Kisselev, A. F., and Goldberg, A. L. (1997). Processive degradation of proteins and other catalytic properties of the proteasome from *Thermoplasma acidophilum*. J Biol Chem 272, 1791-1798.
2. Bewley, M. C., Graziano, V., Griffin, K., and Flanagan, J. M. (2006). The asymmetry in the mature amino-terminus of ClpP facilitates a local symmetry match in ClpAP and ClpXP complexes. J Struct Biol 153, 113-128.
3. Butler, S. M., Festa, R. A., Pearce, M. J., and Darwin, K. H. (2006). Self-compartmentalized bacterial proteases and pathogenesis. Mol Microbiol 60, 553-562.
4. Flanagan, J. M., Wall, J. S., Capel, M. S., Schneider, D. K., and Shanklin, J. (1995). Scanning transmission electron microscopy and small-angle scattering provide evidence that native *Escherichia coli* ClpP is a tetradecamer with an axial pore. Biochemistry 34, 10910-10917.
5. Hoskins, J. R., Pak, M., Maurizi, M. R., and Wickner, S. (1998). The role of the ClpA chaperone in proteolysis by ClpAP. Proc Natl Acad Sci 95, 12135-12140.
6. Hwang, B. J., Park, W. J., Chung, C. H., and Goldberg, A. L. (1987). *Escherichia coli* contains a soluble ATP-dependent protease (Ti) distinct from protease La. Proc Natl Acad Sci 84, 5550-5554.
7. Ingvarsson, H., Mate, M. J., Hogbom, M., Portnoi, D., Benaroudj, N., Alzari, P. M., Ortiz-Lombardia, M., and Unge, T. (2007). Insights into the inter-ring plasticity of caseinolytic proteases from the X-ray structure of *Mycobacterium tuberculosis* ClpP1. Acta Crystallogr D Biol Crystallogr 63, 249-259.
8. Ishikawa, T., Beuron, F., Kessel, M., Wickner, S., Maurizi, M. R., and Steven, A. C. (2001). Translocation pathway of protein substrates in ClpAP protease. Proc Natl Acad Sci 98, 4328-4333.
9. Kang, S. G., Dimitrova, M. N., Ortega, J., Ginsburg A., and Maurizi, M. R. (2005). Human mitochondrial ClpP is a stable heptamer that assembles into a tetradecamer in the presence of ClpX. J Biol Chem 280, 35424-35432.
10. Katayama-Fujimura, Y., Gottesman, S., and Maurizi, M. R. (1987). A multiple-component, ATP-dependent protease from *Escherichia coli*. J Biol Chem 262, 4477-4485.
11. Kim, Y. I., Levchenko, I., Fraczkowska, K., Woodruff, R. V., Sauer, R. T., and Baker, T. A. (2001). Molecular determinants of complex formation between Clp/Hsp100 ATPases and the ClpP peptidase. Nat Struct Biol 8, 230-233.
12. Kirstein, J., Hoffmann, A., Lilie, H., Schmidt, R., Rubsamen-Waigmann, H., Brotz-Oesterhelt, H., Mogk, A., and Turgay, K. (2009). The antibiotic ADEP reprogrammes ClpP, switching it from a regulated to an uncontrolled protease. EMBO Mol Med 1, 37-49.

13. Kress, W., Maglica, Z., and Weber-Ban, E. (2009). Clp chaperone-proteases: structure and function. Res Microbiol 160, 618-628.
14. Lee, B. G., Park, E. Y., Lee, K. E., Jeon, H., Sung, K. H., Paulsen, H., Rubsamen-Schaeff, H., Brotz Oesterhelt, H., and Song, H. K. (2010). Structures of ClpP in complex with acyldepsipeptide antibiotics reveal its activation mechanism. Nat Struct Mol Biol 17, 471-478.
15. Lee, J. W., Park, E., Jeong, M. S., Jeon, Y. J., Eom, S. H., Seol, J. H., and Chung, C. H (2009). HslVU ATP-dependent protease utilizes maximally six among twelve threonine active sites during proteolysis. J Biol Chem 284, 33475-33484.
16. Maurizi, M. R. (1991). ATP-promoted interaction between Clp A and Clp P in activation of Clp protease from *Escherichia coli*. Biochem Soc Trans 19, 719-723.
17. Maurizi, M. R., Clark, W. P., Katayama, Y., Rudikoff, S., Pumphrey, J., Bowers, B., and Gottesman, S. (1990a). Sequence and structure of ClpP, the proteolytic component of the ATP-dependent Clp protease of *Escherichia coli*. J Biol Chem 265, 12536-12545.
18. Maurizi, M. R., Clark, W. P., Kim, S. H., and Gottesman, S. (1990b). ClpP represents a unique family of serine proteases. J Biol Chem 265, 12546-12552.
19. Maurizi, M. R., Singh, S. K., Thompson, M. W., Kessel, M., and Ginsburg, A. (1998). Molecular properties of ClpAP protease of *Escherichia coli*: ATP-dependent association of ClpA and clpP. Biochemistry 37, 7778-7786.
20. Maurizi, M. R., Thompson, M. W., Singh, S. K., and Kim, S. H. (1994). Endopeptidase Clp: ATP-dependent Clp protease from *Escherichia coli*. Methods Enzymol 244, 314-331.
21. Ortega, J., Singh, S. K., Ishikawa, T., Maurizi, M. R., and Steven, A. C. (2000). Visualization of substrate binding and translocation by the ATP-dependent protease, ClpXP. Mol Cell 6, 1515-1521.
22. Peltier, J. B., Ripoll, D. R., Friso, G., Rudella, A., Cai, Y., Ytterberg, J., Giacomelli, L., Pillardy, J., and van Wijk, K. J. (2004). Clp protease complexes from photosynthetic and non-photosynthetic plastids and mitochondria of plants, their predicted three-dimensional structures, and functional implications. J Biol Chem 279, 4768-4781.
23. Peltier, J. B., Ytterberg, J., Liberles, D. A., Roepstorff, P., and van Wijk, K. J. (2001). Identification of a 350 kDa ClpP protease complex with 10 different Clp isoforms in chloroplasts of *Arabidopsis thaliana*. J Biol Chem 276, 16318-16327.
24. Porankiewicz, J., Wang, J., and Clarke, A. K. (1999). New insights into the ATP-dependent Clp protease: *Escherichia coli* and beyond. Mol Microbiol 32, 449-458.
25. Powers, J. C., and Kam, C. M. (1994). Isocoumarin inhibitors of serine peptidases. Methods Enzymol 244, 442-457.
26. Reid, B. G., Fenton, W. A., Horwich, A. L., and Weber-Ban, E. U. (2001). ClpA mediates directional translocation of substrate proteins into the ClpP protease. Proc Natl Acad Sci 98, 3768-3772.
27. Sassetti, C. M., Boyd, D. H., and Rubin, E. J. (2003). Genes required for mycobacterial growth defined by high density mutagenesis. Mol Microbiol 48, 77-84.
28. Sherrid, A. M., Rustad, T. R., Cangelosi, G. A., and Sherman, D. R. (2010). Characterization of a Clp protease gene regulator and the reaeration response in *Mycobacterium tuberculosis*. PLoS One 5, e 11622.
29. Shin, D. H., Lee, C. S., Chung, C. H., and Suh, S. W. (1996). Molecular symmetry of the ClpP component of the ATP-dependent Clp protease, an *Escherichia coli* homolog of 20S proteasome. J Mol Biol 262, 71-76.
30. Socha, A. M., Tan, N. Y., LaPlante, K. L., and Sello, J. K. (2010). Diversity-oriented synthesis of cyclic acyldepsipeptides leads to the discovery of a potent antibacterial agent. Bioorg Med Chem 18, 7193-7202.
31. Viala, J. and Mazodier, P. (2002) ClpP-dependent degradation of PopR allows tightly regulated expression of the clpP3 clpP4 operon in *Streptomyces lividans*. Mol Microbiol 44, 633-643.
32. Viala, J., Rapoport, G., and Mazodier, P. (2000) The clpP multigenic family in *Streptomyces lividans*: conditional expression of the clpP3 clpP4 operon is controlled by PopR, a novel transcriptional activator. Mol Microbiol 38, 602-612.
33. Wang, J., Hartling, J. A., and Flanagan, J. M. (1997) The structure of ClpP at 2.3 A resolution suggests a model for ATP-dependent proteolysis. Cell 91, 447-456.
34. Yu, A. Y., and Houry, W. A. (2007) ClpP: a distinctive family of cylindrical energy-dependent serine proteases. FEBS Lett 581, 3749-3757.

Example 2: In *Mycobacterium tuberculosis*, ClpP and ClpP2 Form a Single Protease Complex Essential for Viability and Virulence In most bacteria, ClpP is a conserved, non-essential protease that regulates the response to various stresses. *Mycobacterium tuberculosis* (Mtb), unlike most prokaryotes, encodes two ClpP homologs, ClpP1 and ClpP2 in a single operon. A transposon-based mutagenesis screen for essential genes in Mtb predicted that ClpP2 and the ATPase adapters ClpC1 and ClpX, were required for normal growth (Sassetti et al., 2003). Through inducible expression of ClpP1 and ClpP2, it is demonstrated herein that both genes are essential for growth and that depletion of either subunit results in cell death. Also demonstrated herein is that the ClpP1P2 protease is required for the degradation of SsrA-tagged proteins. ClpP1P2 appears important in degrading missense and prematurely terminated peptides since partial depletion of ClpP2 reduced growth especially in the presence of antibiotics that increase errors in translation. Using active site mutants of ClpP1 and ClpP2, it is shown herein that the activity of each subunit is required for normal growth of Mtb in vitro and for virulence in a murine model of infection. These observations suggest that the ClpP1P2 protease could serve as an ideal target for antimycobacterial therapy.

Results

ClpP1 and ClpP2 Subunits Interact In Vivo and In Vitro.

Figure 7A:
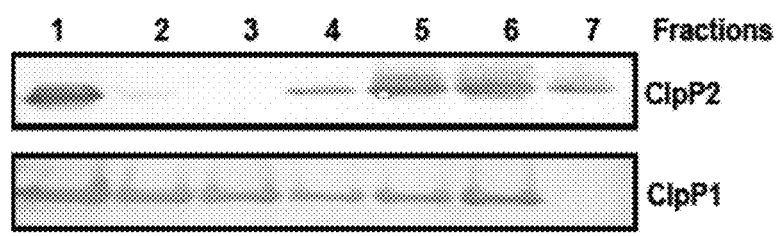

Mycobacterial genomes contain two highly homologous ClpP protease genes, clpP1 and clpP2, arranged in a putative operon. To investigate whether the two proteins may function together in a complex in vivo, Mtb ClpP1 and ClpP2 were co-expressed, each containing a different C terminal epitope tag, in *Mycobacterium smegmatis* (Msm). Affinity chromatography with nickel resin was used to isolate 6x-His (SEQ ID NO: 26) tagged Mtb ClpP2 together with associated proteins from the Msm cell lysate. As shown in FIG. 7A, while some ClpP1 was observed in the flow through, a fraction of the c-myc tagged ClpP1 bound to the Ni column and co-eluted with ClpP2.

Figure 7B:
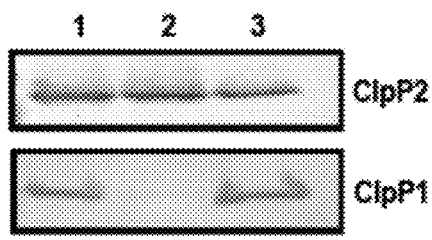

To verify that ClpP1 and ClpP2 co-eluted from the Ni column may be associated in a complex, the fraction from the Ni column containing both proteins was applied to an anti-c-myc agarose column and analyzed by SDS PAGE. FIG. 7B shows that a large fraction of the ClpP2 was associated with the column along with ClpP1. Incidentally, expression of the Mtb proteins in Msm also led to the co-isolation of Msm ClpP1 and ClpP2, as shown by tandem mass spectrometry of the purified complex. In each case, peptides present uniquely in Mtb or Msm ClpP1 and ClpP2 were detected (FIG. 7C).

Figure 7D:
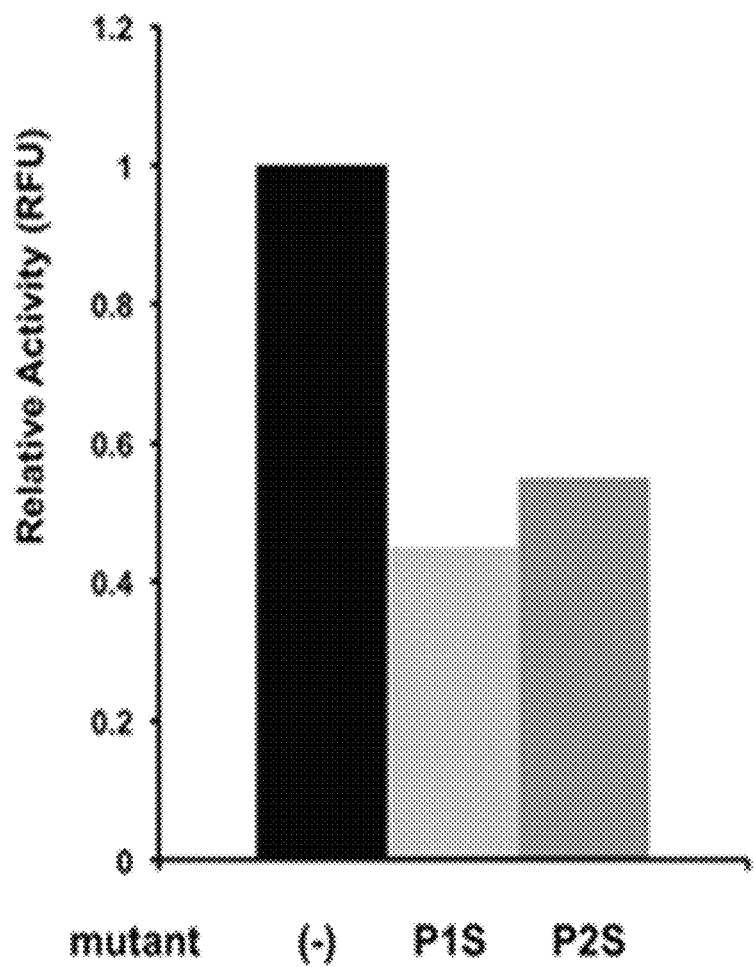

Since ClpP1 and ClpP2 can form a single proteolytic complex (as described elsewhere herein) it was reasoned that mutations blocking the catalytic activity of one subunit might reduce that activity of the enzyme. Likely active site residues of ClpP1 and ClpP2 were identified by mapping the Mtb proteins onto E. coli ClpP and locating the catalytic triad of Asp-His-Ser, which is characteristic of serine proteases. In both cases, the serine likely to be responsible for nucleophilic attack was replaced by an alanine (ClpP1-Ser98Ala and ClpP2-Ser110Ala). To analyze the effects of these mutations, these proteins or the wildtype ClpP1 and ClpP2 were expressed and isolated, and assayed the enzymes assayed as described elsewhere herein. As seen in FIG. 7D, addition of an excess of mutated ClpP1 or ClpP2 to the active wildtype ClpP1P2 complex inhibited proteolytic cleavage of a fluorescent peptide substrate, presumably by replacing the wildtype subunits. These in vitro results support the conclusion that the ClpP1 and ClpP2 subunits interact to form a single proteolytic complex, that each active site is important for activity, and that these mutations can be used as dominant negative inhibitors in vivo.

Both ClpP1 and ClpP2 are Required for Normal Growth In Vitro.

Three complementary strategies were employed to determine if ClpP1 and ClpP2 are required for normal growth in mycobacteria. First, using mycobacterial recombineering (van Kessel and Hatfull, 2008), the endogenous promoter of clpP1 and clpP2 in Msm was replaced with a tetracycline-inducible promoter (FIG. 8A, FIGS. 11A-11B). Introduction of a tetracycline repressor resulted in a strain (ptet_clpP1P2) that could only be maintained in the presence of the inducer anhydrotetracycline (ATc) (FIG. 8B). In the absence of this compound, growth did not occur, but could be restored by the presence of an episomal plasmid containing both clpP1 and clpP2.

Figure 8C:
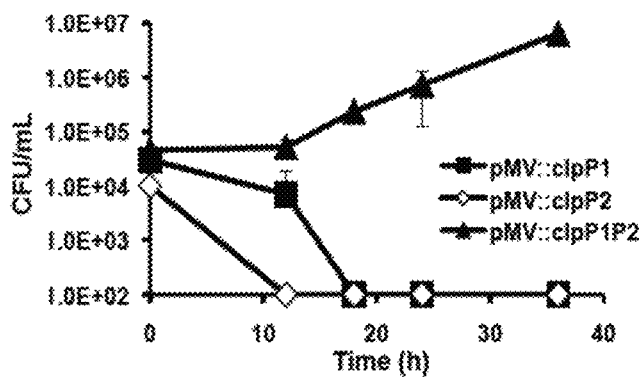
Figure 8D:
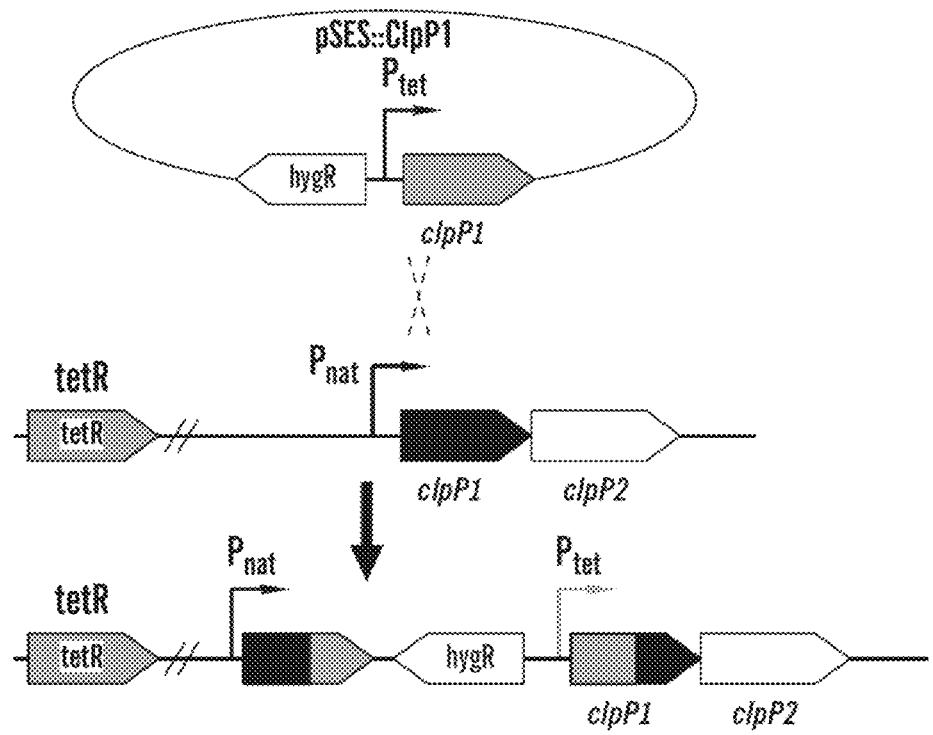
Figure 8E:
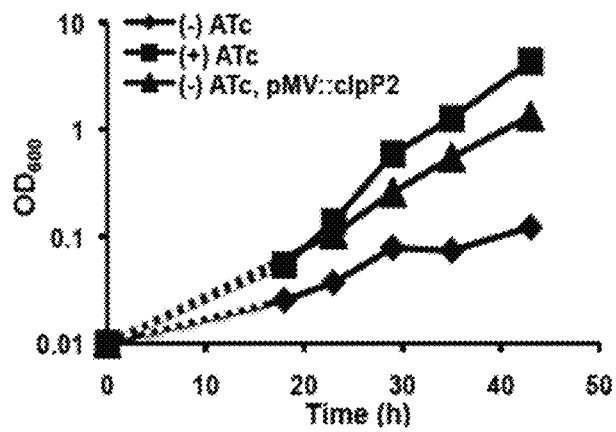

Plasmids expressing only clpP1 or clpP2 alone could not rescue growth and depletion of either subunit resulted in bacterial death (FIG. 8C). Since complementation was conducted with Mtb homologs, the ClpP1P2 complex must be very similar in Msm and Mtb, as was also indicated above by formation of mixed complexes containing both species' subunits. Second, a tetracycline inducible promoter was inserted upstream of the clpP1P2 operon via homologous recombination in Msm creating a strain in which ClpP2 was inducibly expressed (FIG. 8D), and ClpP1 was under the control of its native promoter (ptet_clpP2). In accord with the previous findings, the growth of this strain was dramatically inhibited in the absence of ATc (FIG. 8E).

Figure 8F:
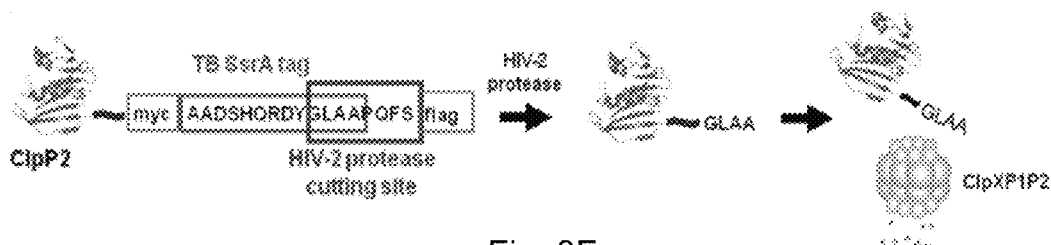
Figure 8G:
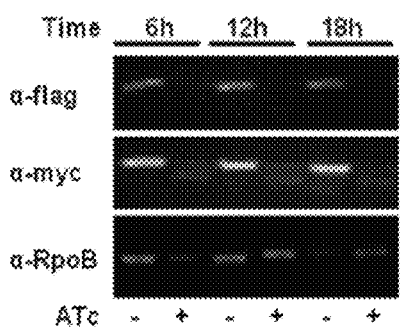
Figure 8H:
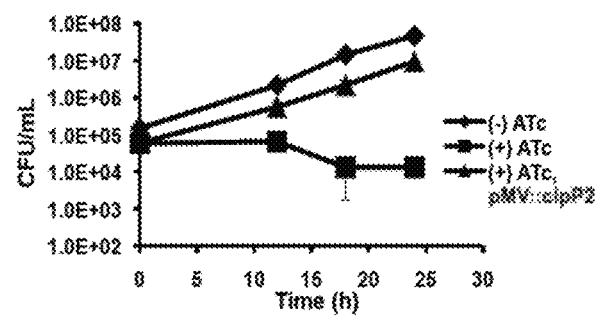

Third, a novel system of inducible protein degradation recently developed in *Mycobacterium smegmatis* (FIG. 8F) (Wei et al., 2010) was used. Briefly, mycobacterial recombineering was employed to add an inducible degradation (ID) tag to the C-terminus of ClpP2 (clpP2_ID). Upon cleavage of the tag by inducibly expressed HIV-2 protease, an SsrA sequence is revealed on the substrate which directs degradation of the protein. By inserting epitope tags C-terminally to the HIV-2 protease recognition motif (flag) and N-terminally to the SsrA tag (c-myc), it was possible to monitor the amount of ClpP2 by Western blot. As shown in FIG. 8G, induction of HIV-2 protease resulted in degradation of ClpP2 and inhibited bacterial growth (FIG. 8H). Depletion of ClpP2, as measured by Western blot, was rapid and reached near completion within hours. Furthermore, the growth defect was complemented by constitutive expression of Mtb clpP2. A similar approach with ClpP1 was unsuccessful as extended C-terminal tagging was not tolerated, and the ID tag was indiscriminately cleaved. Collectively, these results confirm that both ClpP1 and ClpP2 gene products are required for normal growth in mycobacteria, presumably because they function together in the ClpP1P2 complex.

Mycobacterial Clp Protease Plays a Role in Protein Quality Control.

Figures 9A, 9B, 9C:
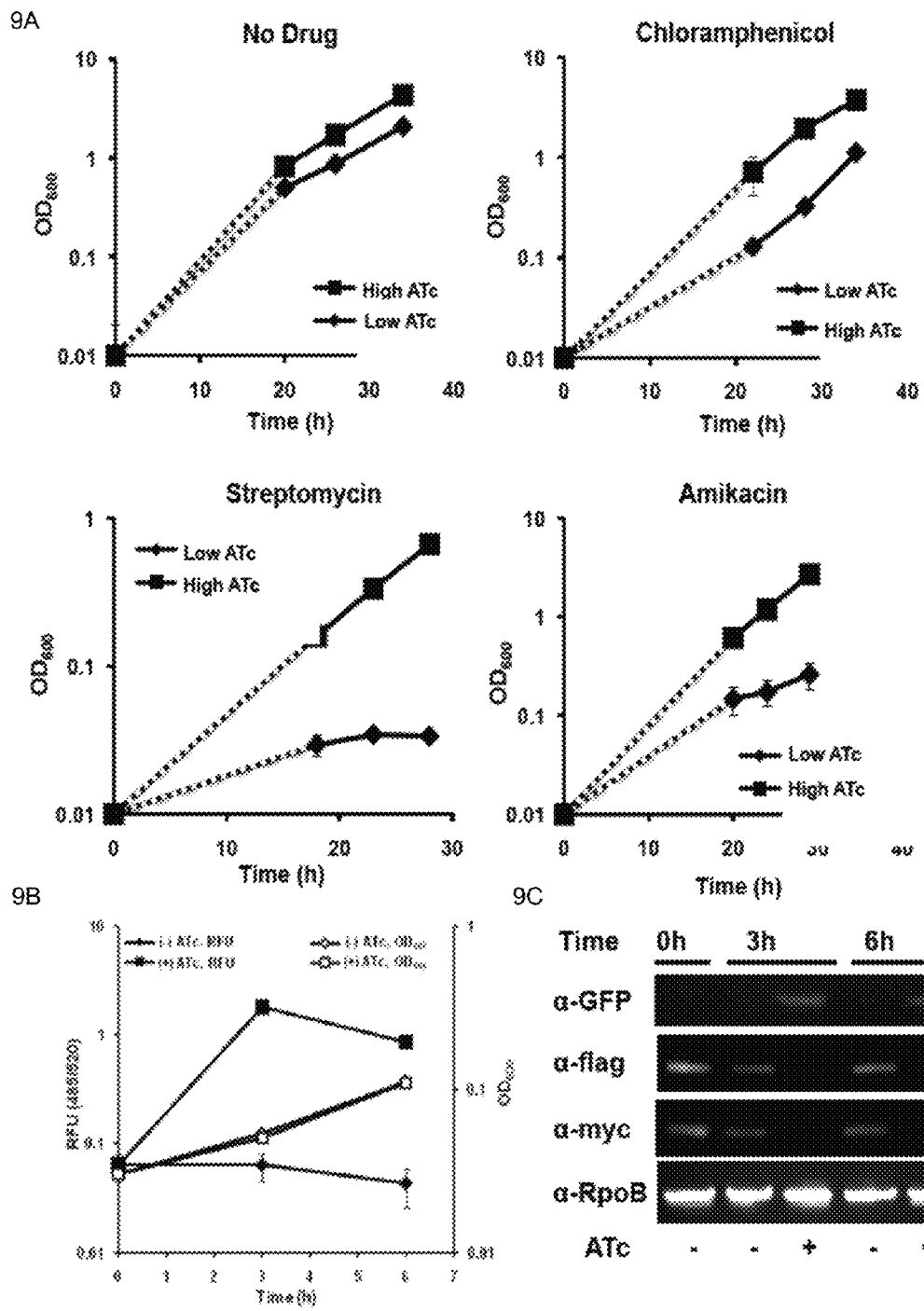
FIGS. 9A-9C demonstrate that Clp protease is required for degradation of abnormal proteins and SsrA-tagged proteins in mycobacteria.

In other bacteria, ClpP plays a role in degrading abnormal proteins such as SsrA-tagged peptides that stall on the ribosome (Frees and Ingmer, 1999). To determine the importance of ClpP1P2 protease in the degradation of misfolded proteins, antibiotics that alter protein synthesis in distinct ways were used, including chloramphenicol, which blocks protein elongation without increasing mistranslation rates (Hahn et al., 1955), and streptomycin and amikacin, which induce translational errors resulting in missense or prematurely-terminated polypeptides (Wyka and St John, 1990). The strain ptet_ClpP2, in which ClpP2 expression is regulated by anhydrotetracycline, was found to grow well in low or high concentrations of ATc, 1 to 100 ng/mL (FIG. 9A, top left). Treatment with sublethal concentrations of chloramphenicol resulted in no difference in viability between bacteria maintained on low or high concentrations of ATc (FIG. 9A, top right). In contrast, sub-MIC concentrations of the aminoglycosides streptomycin and amikacin significantly inhibited the growth of strains incubated in low concentrations of ATc, while they had no effect on growth of the strain maintained in high concentrations of ATc (FIG. 9A, bottom). Together, these results suggest that ClpP1P2 protease protects against error-prone translation by catalyzing the degradation of misfolded proteins.

Figure 12:
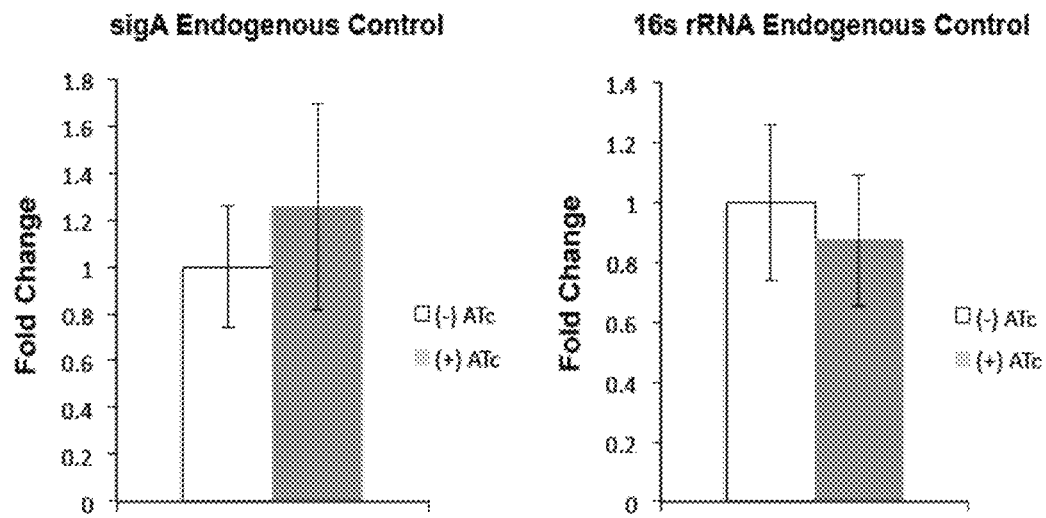
FIG. 12 depicts graphs of quantitative PCT demonstrating that the rise of GFP-SSrA in FIGS. 9A-9C is not due to transcriptional activation of the gene. The left panel shows the expression level of GFP-SSrA normalized to a sigA control and the right panel shows the expression level of GFP-SSrA normalized to a 16s rRNA endogenous control. White bars represent untreated cells while grey bars represent cells treated with ATc. Quantitative PCR of clpP2_ID was carried out to determine if increase in GFP-SsrA was due to transcriptional activation. RNA was isolated from clpP2_ID four hours after induction with ATc (+ ATc), and a culture of equal $OD_{600}$ that was left uninduced (− ATc). Using both sigA (left) and 16s rRNA (right) as endogenous controls, there was no significant difference in transcription of GFP-SsrA between induced and uninduced cultures. Data are represented as mean fold change +/− standard deviation, with values normalized to those of the uninduced culture.

To specifically assess whether ClpP1P2 is responsible for the removal of SsrA-tagged proteins in mycobacteria, the mycobacterial SsrA-tag was fused to the C-terminus of GFP (GFP7 SsrA) and expressed the construct constitutively on an episomal plasmid. This construct was introduced into the strain clpP2_ID, in which ClpP2 degradation was regulated. In the presence of ClpP2, there were no detectable amounts of GFP in the cells. However, upon depletion of ClpP2, there was a substantial rise within four hours in the amount of GFP-SsrA, as measured by both fluorescence and Western blot analysis (FIGS. 9B, 9C). Quantitative PCR showed that the rise of GFP-SsrA was not due to transcriptional activation of the gene (FIG. 12). The rate of accumulation of GFP was consistent with the time course of ClpP2 depletion, which occurred over the course of six hours, as shown by Western blot. Thus, functional ClpP1P2 protease is vital for the rapid clearance of SsrA-tagged substrates in mycobacteria.

Functional ClpP Protease is Required for Growth of Mtb In Vitro and During Infection.

As shown above and in the accompanying paper, catalytically inactive forms of ClpP1 and ClpP2 inhibit proteolysis by the wildtype enzyme, apparently by replacement of wildtype subunits with inactive ones. To assess whether ClpP1P2 activity is required for the growth of Mtb, two different catalytically inactive forms of Mtb ClpP1, ClpP1-Ser98Ala and ClpP1-His123Ala, were expressed on an tetracycline-inducible plasmid in wildtype Mtb. Addition of ATc led to expression of these catalytically inactive mutant proteins and resulted in a significant inhibition of growth (FIG. 10A) while overexpression of wildtype Mtb ClpP1 had no effect.

Figures 10A, 10B:
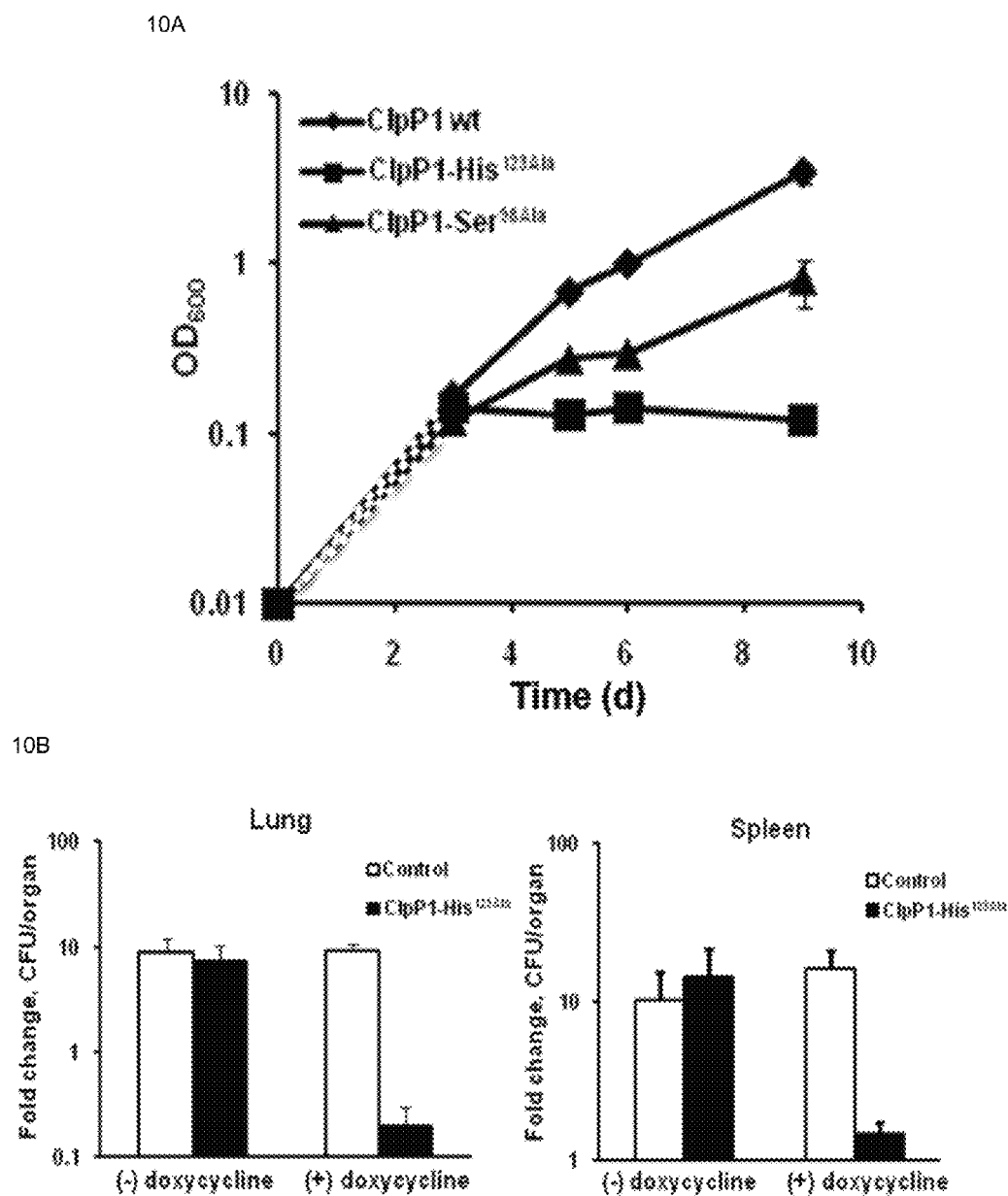
FIGS. 10A-10B demonstrate that catalytically inactive ClpP alleles inhibit Mtb growth in vitro and in vivo.

To determine if these dominant negative mutants of ClpP1 affected ClpP1P2 function in vivo during Mtb infection, mice were infected with a 1:1 mixture of wildtype Mtb (containing control vector) and Mtb expressing ClpP1-His123Ala on a tetracycline inducible plasmid. Mice were fed either normal chow or chow infused with the inducer doxycycline. Growth of Mtb in vivo was monitored by comparing the fold increase in CFU/organ between day 1 and day 27 of infection. There were no differences in the growth of wildtype Mtb between the two groups. However, growth of the ClpP1-His123Ala mutant was much lower in the lungs and spleen of mice fed with doxycycline, than in mice fed with normal chow (FIG. 10B). Our results prove that functional ClpP1P2 protease is required for the growth of Mtb both in vitro and in vivo during infection.

Discussion

The results described herein demonstrate that the mycobacterial ClpP1P2 protease has two quite unusual properties that distinguish it from other members of the ClpP family. First, as described above, the protease consists of distinct types of subunits, each of which is arranged in a heptameric ring and required for activity. Second, unlike in most bacteria that have been studied, ClpP1P2 activity is absolutely required for normal growth. This requirement is particularly striking as mycobacteria contain several cytoplasmic ATP-dependent proteolytic complexes, including as FtsH, and the proteasome (Darwin et al., 2003; Kiran et al., 2009 Smith et al., 1999). Clearly, the mycobacterial ClpP1P2 protease complex has unique roles that are important for viability.

The ClpP protease complexes characterized biochemically in other bacteria and mitochondria are all tetradecameric complexes containing a single type of subunit. In mycobacteria, however, two different protein species contribute to protease activity. Although Mtb ClpP1 forms a tetradecameric complex, a crystal structure of Mtb ClpP1 lacks appropriate active site geometry to support proteolysis (Ingvarsson et al., 2007). One likely explanation for this non-ideal arrangement may be the absence of ClpP2 in this structure. As shown herein, both ClpP1 and ClpP2 subunits are necessary to produce a functionally active enzyme. Interestingly, the Mtb proteasome is composed of a single type of subunit, and the presence of distinct subunits comprising a single proteolytic core is rare among prokaryotes.

As shown herein, ClpP1P2 protease is required for the clearance of SsrA-tagged proteins. These tagged polypeptides are generated under conditions when protein synthesis is stalled and are required for recycling of ribosomes. Without wishing to be bound by theory, in the absence of ClpP1P2-mediated proteolysis, protein synthesis might eventually be inhibited. In addition, ClpP1P2 protease is necessary for degrading abnormal proteins, such as those produced in the presence of certain antibiotics. Accumulation of such non-functional misfolded proteins might result in cellular stress in the absence of an effective system for their removal (Goldberg, 1972). Clearance of damaged proteins might be particularly important in Mtb during infection, when cells are exposed to multiple oxidative and nitrosoative radicals that can induce protein damage. In fact, a transcriptional activator of the clpP1P2 operon, clgR, is critically activated during reaeration of hypoxic Mtb, and during Mtb parasitism within the (Estorninho et al., 2010; Sherrid et al., 2010). The essentiality of ClpP1P2 protease in mycobacteria provides strong evidence for the importance of post-translational regulation of protein abundance. Degradation of pre-existing proteins during such stressful transitions may be the initial event that triggers adaptation, and facilitates the bacterium's ability to handle a wide array of environmental challenges.

The essential nature of ClpP1P2 protease makes it an attractive target for antibiotic development, particularly because the proteases are a well understood type of enzyme and a number of therapeutic agents are protease inhibitors used in the treatment of HIV, hepatitis, and cancer (Rang et al., 2007). In organisms where ClpP is not essential, uncontrolled activation of ClpP activity can be toxic. For example, in E. coli, acyldepsipeptide compounds (ADEPs) reorganize the ClpP proteolytic core, causing dissociation from ATPase adapters, and indiscriminate protein degradation (Kirstein et al., 2009). Compounds that produce a similar effect should result in toxicity in a broad range of organisms. In mycobacteria, where ClpP1P2 protease activity is required and depletion of either subunit is bactericidal, either non-specific activation or inhibition could effectively limit bacterial growth. In fact, an example of a ClpP inhibitor with potential therapeutic activity already exists. In S. aureus, beta-lactones have been found to inhibit ClpP protease activity and decrease the virulence of the organism (Bottcher and Sieber, 2008). Furthermore, the synergistic nature of ClpP1P2 protease depletion with aminoglycosides, a class of drugs already used to treat tuberculosis, points to a potential combination therapy against Mtb. Small molecule modulators of ClpP1P2 activity would target a critical aspect of Mtb physiology, and might prove useful in the face of growing multi-drug resistance in one of the world's most successful pathogens.

Prior attempts (Sassetti, et al (2003) Mol Microbiol 48, 77-84) to isolate and characterize mycobacterial ClpP protease were unsuccessful. However, described herein, is the expression and purification of this novel enzyme and characterization of its highly unusual structural, enzymatic and regulatory properties. Further described herein, is that 1) products of two M. tuberculosis genes, clpP1 and clpP2, are essential for growth of mycobacteria (unlike ClpP homologs in other bacterial species) and for M. tuberculosis infection of mice; 2) ClpP1 and ClpP2 form a mixed ClpP1P2 14-subunit proteolytic complex protease; 3) purification and characterization of mature N-terminally processed active forms of ClpP1 and ClpP2; 4) reconstitution of an active complex and identification of certain short peptides that dramatically activate ClpP1P2 against peptides and proteins; 5) elucidation of a highly unusual mechanism of activation through dissociation of ClpP1 and ClpP2 14-mers into 7-mers and their subsequent re-association into the active ClpP1P2 complex, 6) demonstration that M. tuberculosis ClpP1P2 is composed of one ClpP1 and one ClpP2 heptameric ring. 7) demonstration that ClpP1 and ClpP2 both possess chymotrypsin and caspase like activities, but ClpP1's active sites are much more important in proteolysis than ClpP2's; 8) construction of a specific fluorescent protein substrate for Mtb ClpP1P2 that will allow monitoring of ClpP1P2 activity in living mycobacteria and will serve as an important tool in evaluating the uptake and efficacy of inhibitors generated in in vitro screens. In summary, the data described herein clearly demonstrate that ClpP1P2 is an unusual proteolytic complex, quite different from any known mammalian or bacterial protease and thus represents an attractive drug target.

Experimental Procedures

Bacterial Strains and Plasmids.

Msm mc2155 (Msm) or Mtb H37Rv were grown at 37° C. in Middlebrook 7H9 broth with 0.05% Tween 80 and ADC (0.5% BSA, 0.2% dextrose, 0.085% NaCl, 0.003 g catalase/1 L media). Mtb was additionally supplemented with oleic acid (0.006%). For growth curves, overnight cultures were diluted into the appropriate media and growth was either measured by $OD_{600}$ or colony forming units per mL.

Protein Purification and In Vitro Peptidase Assay.

The C-terminally 6xHis-tagged (SEQ ID NO: 26) wildtype ClpP1, wildtype ClpP2, ClpP1Ser98Ala, and ClpP2Ser110Ala subunits were overexpressed in Msm using an anhydrotetracycline (ATc) inducible expression system. After overnight induction with ATc (100 ng/mL), cells were lysed by French press, and lysates were centrifuged for 1h at 100,000 g. The subunits were purified from the supernatant by nickel affinity chromatography as per the manufacturer's protocol (Qiagen). Eluted fractions were pooled and further purified by size exclusion chromatography.

Equal amounts of ClpP1 and ClpP2 (1 µg each) were mixed in the reaction buffer (50 mM $KPO_4$ pH 7,5, 100 mM $KCl_2$, 10% glycerol, 2 mM BME, 1 mM Z-Leu-Leu) and peptidase activity was measured by a rise in fluorescence (485/520) with 0.1 mM Z-Gly-Gly-Leu-amc as a substrate. To measure dominant negative effect of active site mutants, same reaction was carried out in the presence of 5 µg of the mutant proteins.

Animal Infections.

Six to eight week old C57/B16 mice (Jackson Laboratory) were used for animal infections. Mice were injected intravenously with 1×106 CFU each of a 1:1 mixture of Mtb pTet::ClpP1-His123Ala and Mtb pTet::GFP (wildtype Mtb transformed with a control pTet plasmid containing GFP). Mice were fed with chow with or without inducer doxycycline. At the end of 24 h or 27 days after infection mice were sacrificed, spleens and lungs were homogenized and appropriate dilutions were plated on 7H10 plates containing hygromycin or kanamycin to select for the Clp mutant or the control respectively.

REFERENCES

1. Bottcher, T., and Sieber, S. A. (2008). Beta-lactones as specific inhibitors of ClpP attenuate the production of extracellular virulence factors of *Staphylococcus aureus*. J Am Chem Soc 130, 14400-14401.
2. Burns, K. E., Pearce, M. J., and Darwin, K. H. (2010). Prokaryotic ubiquitin-like protein provides a two-part degron to *Mycobacterium* proteasome substrates. J Bacteriol 192, 2933-2935.
3. Cerda-Maira, F. A., Pearce, M. J., Fuortes, M., Bishai, W. R., Hubbard, S. R., and Darwin, K. H. (2010) Molecular analysis of the prokaryotic ubiquitin-like protein (Pup) conjugation pathway in *Mycobacterium tuberculosis*. Mol Microbiol.
4. Darwin, K. H., Ehrt, S., Gutierrez-Ramos, J. C., Weich, N., and Nathan, C. F. (2003). The proteasome of *Mycobacterium tuberculosis* is required for resistance to nitric oxide. Science 302, 1963-1966.
5. Ehrt, S., Guo, X. V., Hickey, C. M., Ryou, M., Monteleone, M., Riley, L. W., and Schnappinger, D. (2005). Controlling gene expression in mycobacteria with anhydrotetracycline and Tet repressor. Nucleic Acids Res 33, e2 1.
6. Estorninho, M., Smith, H., Thole, J., Harders-Westerveen, J., Kierzek, A., Butler, R. E., Neyrolles, O., and Stewart, G. R. (2010). ClgR regulation of chaperone and protease systems is essential for *Mycobacterium tuberculosis* parasitism of the macrophage. Microbiology.
7. Farrell, C. M., Grossman, A. D., and Sauer, R. T. (2005). Cytoplasmic degradation of ssrA-tagged proteins. Mol Microbiol 57, 1750-1761.
8. Frees, D., and Ingmer, H. (1999). ClpP participates in the degradation of misfolded protein in *Lactococcus lactis*. Mol Microbiol 31, 79-87.
9. Frees, D., Savijoki, K., Varmanen, P., and Ingmer, H. (2007). Clp ATPases and ClpP proteolytic complexes regulate vital biological processes in low GC, Gram-positive bacteria. Mol Microbiol 63, 18 1285-1295.
10. Gaillot, O., Bregenholt, S., Jaubert, F., DiSanto, J. P., and Berche, P. (2001). Stress-induced ClpP serine protease of *Listeria monocytogenes* is essential for induction of listeriolysin O-dependent protective immunity. Infect Immun 69, 4938-4943.
11. Gaillot, O., Pellegrini, E., Bregenholt, S., Nair, S., and Berche, P. (2000). The ClpP serine protease is essential for the intracellular parasitism and virulence of *Listeria monocytogenes*. Mol Microbiol 35, 1286-1294.
12. Glickman, M. H., and Ciechanover, A (2002). The ubiquitin-proteasome proteolytic pathway: Destruction for the sake of construction. Physiol Rev 82, 373-428.
13. Goldberg, A. L. (1972) Degradation of abnormal proteins in *E. coli*. Proc Natl Acad Sci 69, 422-426.
14. Goldberg, A. L. (2003). Protein degradation and protection against misfolded or damaged proteins. Nature 426, 895-899.
15. Hahn, F. E., Wisseman, C. L., Jr., and Hopps, H. E. (1955). Mode of action of Zchloramphenicol. III. Action of chloramphenicol on bacterial energy metabolism. J Bacteriol 69, 215-223.
16. Hwang, B. J., Park, W. J., Chung, C. H., and Goldberg, A. L. (1987). *Escherichia coli* contains a soluble ATP-dependent protease (Ti) distinct from protease La. Proc Natl Acad Sci 84, 5550-5554.
17. Ingmer, H., and Brondsted, L. (2009). Proteases in bacterial pathogenesis. Res Microbiol 160, 704-710.
18. Ingvarsson, H., Mate, M. J., Hogbom, M., Portnoi, D., Benaroudj, N., Alzari, P. M., Ortiz-Lombardia, M., and Unge, T. (2007). Insights into the inter-ring plasticity of caseinolytic proteases from the X-ray structure of *Mycobacterium tuberculosis* ClpP1. Acta Crystallogr D Biol Crystallogr 63, 249-259.
19. Jenal, U., and Fuchs, T. (1998). An essential protease involved in bacterial cell-cycle control. EMBO J 17, 5658-5669.
20. Katayama-Fujimura, Y., Gottesman, S., and Maurizi, M. R. (1987). A multiple-component, ATP-dependent protease from *Escherichia coli* J Biol Chem 262, 4477-4485.
21. Kenniston, J. A., Baker, T. A., Fernandez, J. M., and Sauer, R. T. (2003). Linkage between ATP consumption and mechanical unfolding during the protein processing reactions of an AAA+ degradation machine. Cell 114, 511-520.
22. Kiran, M., Chauhan, A., Dziedzic, R., Maloney, E., Mukherji, S. K., Madiraju, M., and Rajagopalan, M (2009). *Mycobacterium tuberculosis* ftsH expression in response to stress and viability. Tuberculosis (Edinb) 89 Suppl 1, S70-73.
23. Kirstein, J., Hoffmann, A., Lilie, H., Schmidt, R., Rubsamen-Waigmann, H., Brotz-Oesterhelt, H., Mogk, A., and Turgay, K. (2009). The antibiotic ADEP reprogrammes ClpP, switching it from a regulated to an uncontrolled protease. EMBO Mol Med 1, 37-49.
24. Mogk, A., Dougan, D., Weibezahn, J., Schlieker, C., Turgay, K., and Bukau, B. (2004). Broad yet high substrate specificity: the challenge of AAA+ proteins. J Struct Biol 146, 90-98.
25. Pruteanu, M., and Baker, T. A. (2009). Controlled degradation by ClpXP protease tunes the levels of the excision repair protein UvrA to the extent of DNA damage. Mol Microbiol 71, 912-924.

26. Quon, K. C., Marczynski, G. T., and Shapiro, L. (1996). Cell cycle control by an essential bacterial two-component signal transduction protein. Cell 84, 83-93.

27. Rang, H. P., Dale, M. M., Ritter, J. M., and Flower, R. J. (2007). Rang and Dale's Pharmacology, Vol 1, 6th edition edn (Philadelphia, Churchill Livingstone Elsevier).

28. Sassetti, C. M., Boyd, D. H., and Rubin, E. J. (2003). Genes required for mycobacterial growth defined by high density mutagenesis. Mol Microbiol 48, 77-84.

29. Sherrid, A. M., Rustad, T. R., Cangelosi, G. A., and Sherman, D. R. (2010). Characterization of a Clp protease gene regulator and the reaeration response in *Mycobacterium tuberculosis*. PLoS One 5, e11622.

30. Smith, C. K., Baker, T. A., and Sauer, R. T. (1999). Lon and Clp family proteases and chaperones share homologous substrate-recognition domains. Proc Natl Acad Sci 96, 6678-6682.

31. Van Kessel, J. C., and Hatfull, G. F. (2007). Recombineering in *Mycobacterium tuberculosis*. Nat Methods 4, 147-152.

32. Wang J., Hartling J. A., and Flanagan J. M. (1997). The structure of ClpP at 2.3 A resolution suggests a model for ATP-dependent proteolysis. Cell 91, 447-456.

33. Van Kessel, J. C., and Hatfull, G. F. (2008). Mycobacterial recombineering. Methods Mol Biol 435, 203-215.

34. Wei, J. R., Krishnamoorthy, V., Murphy, K. C., Kim, J. H., Schnappinger, D., Alber, T., Sassetti, C. M., Rhee, K. Y., and Rubin, E. J. (2010). Antibiotic targets vary in their sensitivity to inhibition by depletion. Manuscript submitted.

35. Wyka, M. A., and St John, A. C. (1990). Effects of production of abnormal proteins on the rate of killing of *Escherichia coli* by streptomycin. Antimicrob Agents Chemother 34, 534-538.

TABLE 1

Certain Short Peptide Aldehydes and Peptides Dramatically Activate Mtb ClpP1P2. Peptidase activity was measured with ZGly-Gly-Leu-amc. Maximal activation by Z-Leu-Nle-aldehyde was taken as 100%. "Suc-Leu-Leu-Val-Tyr-amc" disclosed as SEQ ID NO: 32, "Suc-Ala-Leu-Pro-Phe-amc" disclosed as SEQ ID NO: 33, and "Suc-Ala-Ala-Pro-Ala-amc" disclosed as SEQ ID NO: 34.

| COMPOUND | RELATIVE ACTIVITY (%) |
|---|---|
| Peptide Aldehydes (0.5 mM) | |
| Z-Leu-Nle-aldehyde | 100.0 |
| Z-Leu-Leu-aldehyde | 77.6 |
| Z-Val-Phe-aldehyde | 1.9 |
| Z-Phe-Tyr-aldehyde | 1.3 |
| Z-Pro-Nlee-Asp-aldehyde | 1.2 |
| Z-Ala-Pro-Nle-Asp-aldehyde | 0.8 |
| Peptide Derivatives (1 mM) | |
| Z-Leu-Leu-aldehyde | 100.0 |
| Z-Leu-Leu | 18.5 |
| Z-Leu | 5.3 |
| Z-Leu-Leu-alcohol | 17.6 |
| Z-Leu-alcohol | 2.4 |
| Z-Gly-Leu | 4.8 |
| Z-Gly-Gly-Leu | 3.7 |

TABLE 2

Mtb ClpP1P2 Preferentially Hydrolyses Peptides with Hydrophobic and Acidic P1 Residues.

| PEPTIDE SUBSTRATE | RELATIVE RATES OF HYDROLYSIS (%) |
|---|---|
| Hydrophobic P1 Residue | |
| Z-Gly-Gly-Leu-amc | 100.0 |
| Suc-Leu-Leu-Val-Tyr-amc | 0.8 |
| Suc-Leu-Tyr-amc | 11.5 |
| Z-Leu-Leu-Leu-amc | 0.15 |
| Z-Leu-Leu-amc | 4.7 |
| Z-Ala-Ala-Ala-amc | 3.6 |
| Suc-Ala-Leu-Pro-Phe-amc | 0.12 |
| Suc-Ala-Ala-Pro-Ala-amc | 0.08 |
| Ala-Ala-Phe-amc | 87.0 |
| Suc-Ala-Ala-Phe-amc | 42.0 |
| Acidic P1 Residue | |
| Ac-Nle-Pro-Nle-Asp-amc | 36.0 |
| Z-Leu-Leu-Glu-amc | 0.35 |
| Basic P1 Residue | |
| Z-Leu-Leu-Arg-amc | 0.25 |
| Z-Gly-Gly-Arg-amc | 0.55 |
| Z-Phe-Val-Arg-amc | 0.18 |
| Aminopeptidase Substrates | |
| Ala-amc | 0.78 |
| Leu-amc | 0.36 |
| Phe-amc | 0.26 |
| Asp-amc | 0.1 |

TABLE 3

Activation of ClpP1P2 by Z-Leu-Leu is Readily Reversible

| Active Enzyme, Diluted (200x) | Relative Activity (%) |
|---|---|
| With activator | 100.0 |
| Without activator | 1.2 |
| Without activator, then activator re-added | 96.0 |

TABLE 4

Preferred Tripeptide Fluorescent Substrates of Mtb ClpP1P2. Comparison of Kcat/Km with ClpP from *E. coli* and *B. Subtilis*. These new substrates are hydrolyzed much faster by ClpP1P2 (as well as by ClpP from *B. subtilis* and *E. coli*) than standard published substrate Suc-LY-amc. In fact, these three novel peptides are degraded 400-1300 times faster by ClpP1P2 than Suc-LY-amc

| | Kcat/Km ($M^{-1} sec^{-1}$) | | |
|---|---|---|---|
| Substrate Ac-(P3P2P1)-amc | *M. tuberculosis* ClpP1P2 | *B. subtilis* ClpP | *E. coli* ClpP |
| Chymotryptic like | | | |
| Ac-PKM-amc | 1327 | 176 | 2632 |
| Ac-PWM-amc | 1155 | 520 | 4745 |
| Ac-ARM-amc | 410 | 526 | 1553 |
| Suc-LY-amc | 1 | 50 | 721 |

TABLE 5

Main plasmids used in this study:

| Plasmid | Properties/Uses |
| --- | --- |
| pTetOR::clpP1-myc | Inducible expression of c-myc-tagged Mtb ClpP1 (to assess in vivo interaction with ClpP2) |
| pTetOR::clpP2-his | Inducible expression of 6xHis-tagged (SEQ ID NO: 26) Mtb ClpP2 (to assess in vivo interaction with ClpP1) |
| pTetOR::clpP1wt | Inducible expression of Mtb ClpP1 (for in vitro degradation assay) |
| pTetOR::clpP1S | Inducible expression of Mtb ClpP1-Ser$^{98A}$ (for in vitro degradation assay, and overexpression in Mtb) |
| pTetOR::clpP2S | Inducible expression of Mtb ClpP2-Ser$^{110A}$ (for in vitro degradation assay, and overexpression in Mtb) |
| pTetOR::clpP1H | Inducible expression of Mtb ClpP1-His$^{123A}$ (for overexpression in Mtb) |
| p96863 | Non-expressing, synthesized plasmid (Genscript) containing regions of homology to ClpP1 5'UTR and ORF. Used to generate linear PCR product for recombineering to create Msm ptet_clpP1P2 |
| pKM339 | Plasmid used to obtain tetracycline promoter, repressor, and hygromycin resistance marker, which were cut and inserted into p96863 for recombineering to create Msm ptet_clpP1P2 |
| p54689 | Non-expressing, synthesized plasmid (Genscript) containing regions of homology to ClpP2 ORF and 3'UTR. Used to generate linear PCR product for recombineering to create Msm clpP2_ID |
| puc57::inhA-ID | Plasmid used to obtain inducible degradation tag, which was cut and inserted into p54869 for recombineering to create Msm clpP2_ID |
| pSES::ptet_clpP1 | Plasmid used for homologous recombination to create Msm ptet_clpP2 |
| pMV762zeo::clpP1 | Constitutively expressing plasmid expressing Mtb ClpP1 for complementation studies |
| pMV762zeo::clpP2 | Constitutively expressing plasmid expressing Mtb ClpP2 for complementation studies |
| pMV762zeo::clpP1P2 | Constitutively expressing plasmid expressing the entire clpP1clpP2 operon for complementation studies |
| pMV762zeo::GFP-SsrA | Constitutively expressing plasmid expressing the fusion construct GFP-SsrA to assess role of Clp protease in degradation of SsrA-tagged substrates |
| pSES::ClpP1 | Plasmid used for homologous recombination event to create strain, pTet_clpP2 |
| pNit::Che9c | Plasmid expressing mycobacteriophage recombinases, used in mycobacterial recombineering |

TABLE 6

Main primers used in this study:

| Primer Name | Primer Sequence (5' to 3') | SEQ ID NO | Use |
| --- | --- | --- | --- |
| RMR01 | GCACTGTTAATTAAGAAGGAGATATACCTATGCGTTCGAACTCGCAG | 7 | Cloning of processed Mtb ClpP1 into pTetOR, pmv (forward) |
| RMR02 | AGTATACAGCTGTCACTGTGCTTCTCCATTGACCTG | 8 | Cloning of processed Mtb ClpP1 into pTetOR (reverse) |
| sRMR03 | GCACTGTTAATTAAGAAGGAGATATACCTATGCGCTACATCCTGCCGTC | 9 | Cloning of processed Mtb ClpP2 into pTetOR, pmv (forward) |
| RMR04 | AGTATACAGCTGTCAGGCGGTTTGCGCGGA | 10 | Cloning of processed Mtb ClpP2 into pTetOR, pmv (reverse) |
| RMR05 | AGTATACAGCTGTCACAGGTCCTCCTCCGAGATCAGCTTCTGCTCCTGTGCTTCTCCATTGACCTG | 11 | Cloning of processed Mtb ClpP1-myc into pTetOR (reverse) |
| RMR06 | AGTATACAGCTGGTGGTGGTGGTGGTGCTGTGCTTCTCCATTGACCTG | 12 | Cloning of processed Mtb ClpP1-his into pTetOR (reverse) |
| RMR07 | AGTATACAGCTGTCACAGGTCCTCCTCCGAGATCAGCTTCTGCTCGGCGGTTTGCGCGGA | 13 | Cloning of processed Mtb ClpP2-myc into pTetOR, pmv (reverse) |
| RMR08 | AGTATACAGCTGGTGGTGGTGGTGGTGGGCGGTTTGCGCGGA | 14 | Cloning of processed Mtb ClpP2-his into pTetOR, pmv (reverse) |

TABLE 6-continued

Main primers used in this study:

| Primer Name | Primer Sequence (5' to 3') | SEQ ID NO: | Use |
|---|---|---|---|
| RMR09 | GATCCGCATGCTTAAT TAAGAAGGAG | 15 | Cloning of GFP-ssrA into pmv (forward) |
| RMR10 | GTGGTGGTGATGGATG GTGTTTGTATAGTTCAT CCATGCCATG | 16 | Cloning of GFP-ssrA into pmv (reverse, first round) |
| RMR11 | CTGATGTGAATCGGCG TGGTGGTGATGATGGT GTTTCTATAG | 17 | Cloning of GFP-ssrA into pmv (reverse, second round to add first portion SsrA-tag) |
| RMR12 | CGGAATATCGATCTAG GCAGCGAGAGCGTAGT CGCGCTGATGTGAATCGGC | 18 | Cloning of GFP-ssrA into pmv (reverse, third round to add remaining portion SsrA-tag) |
| RMR13 | CCGCCGTGGCCTGACCATC | 19 | Generation of linear PCR product from p96863 to recombineer strain ptet_clpP1P2 (forward) |
| RMR14 | TCTTCCGCCGACAGCAACAGG | 20 | Generation of linear PCR product from p96863 to recombineer strain ptet_clpP1P2 (reverse) |
| RMR15 | CATCCAGGGCCAGTTCTC | 21 | Generation of linear PCR product from p54689 to recombineer strain clpP2_ID (forward) |
| RMR16 | CGTGGTGTTTGCCGTTCT | 22 | Generation of linear PCR product from p54689 to recombineer strain clpP2 _ID (reverse) |
| RMR17 | GCACGGCATACATCAT TTCGACGCCG | 23 | Used in screening for pTet_clpP2 strain (forward). Binds to the tetracycline promoter. |
| RMR18 | GGCGGTTTGCGCGGAGAGC | 24 | Used in screening for pTet_clpP2 strain (reverse). Binds to the 3'-end of clpP2. |

Example 3: Cleavage Specificity of Mtb Clpp1p2 Established Using Tripeptide Substrates Library (Ac-P3-P2-P1-Amc)

The ClpP1P2, essential enzyme in *Mycobacterium tuberculosis* (Mtb) is a potential drug target for the development of anti Mtb therapeutics. An N-acetyl tripeptide-aminomethylcoumarin (Ac-P3-P2-P1-amc) library was used to elucidate the preferable P1, P2 and P3 positions at cleavage sites.

Figures 14A, 14B:
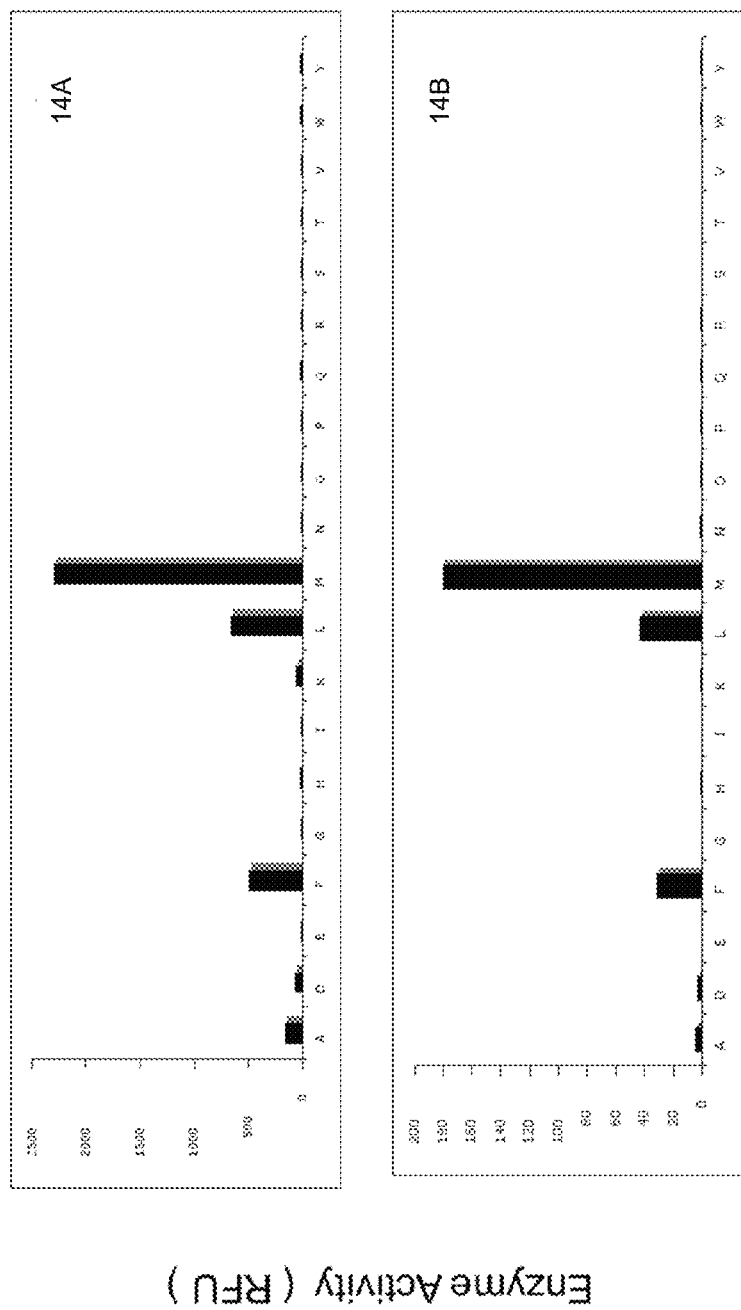
FIGS. 14A-14B depict graphs of the cleavage specificity of Mtb ClpP1P2 at P1 position using Ac-P3-P2-P1-amc library
Figure 15:
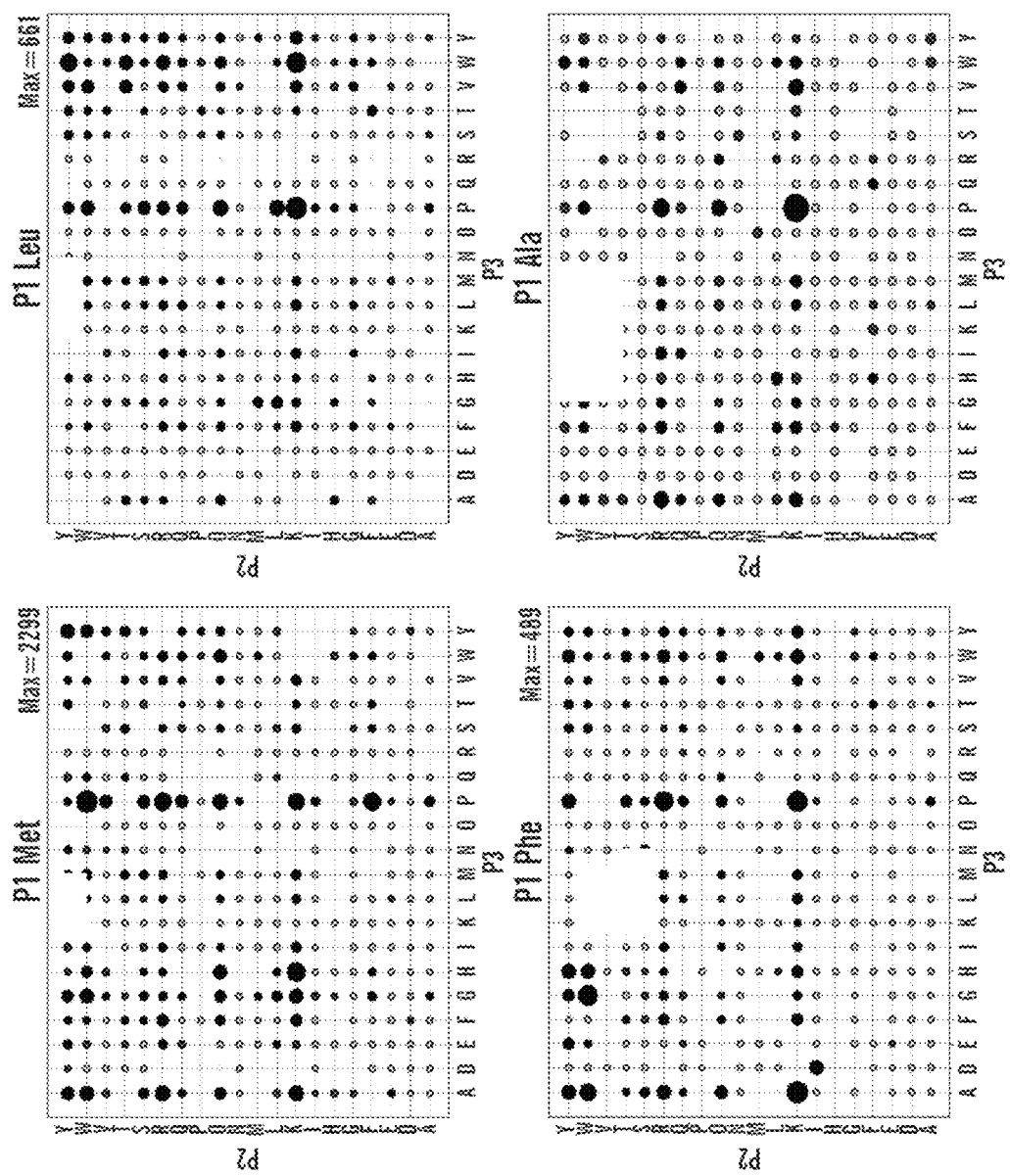
FIG. 15 depicts graphs of the finding of Preferred P2 and P3 Positions for MtbClpP1P2.

Mtb ClpP1P2 was distinctive in preferring Met at P1 position, particularly in combination with Lys and Pro in P2 and P3 position correspondingly. Enzyme also cleaves (but less efficiently) the peptides containing Leu, Phe, Ala and in few cases Asp and Lys at P1 position (FIGS. 14A-14B, 15 and Table 7). Screening results were confirmed by synthesis and kinetic analysis of sixteen substrates. The determined Kcat/Km value indicates that indeed the enzyme prefers the peptide substrates possessing Met at P1, basic at P2 and Pro at P3. The new substrates identified in this study are up to 1000-fold more efficient that substrates currently in use by scientific community (Table 8). Comparative studies indicate that Mtb ClpP1P2 mainly possesses similar specificity with *B. subtilis* and *E. coli* ClpP but differ from human and proteasome (Table 9). The observed distinctive specificity of Mtb ClpP1P2 can be used as basis for the design and synthesis of strong inhibitors with potential anti-tuberculosis activity.

Example 4: Mtb Clpc1/Clpp1p2 Degradative System is Verified as Drug Target

ClpP by itself is able to hydrolyze only small peptides, but not large peptides or globular proteins, whose degradation requires the association with the regulatory AAA ATPase ring complex. The ATPases bind selectively certain protein substrates, unfold them, and translocate polypeptides into the ClpP proteolytic chamber for degradation. Incidentally, both Clp ATPases present in Mtb (ClpC1 and ClpX) are essential for viability and therefore also represent attractive drug targets.

As described herein, once of these ATPases (ClpC1) has been isolated and characterized. It has a number of unusual properties, e.g. unlike other AAA ATPases, it obtains oligomeric functional structure only in the presence of ATP, while in the absence of ATP it exists in the monomeric form. Most importantly, the data described herein establish that ClpC1 functions together with ClpP1P2 protease in the newly-developed in vitro protein degradation assay and stimulates proteolysis several fold (FIG. 16).

Since ClpC1 is an integral part of the essential Clp degradation system and is also an essential protein in Mtb, it represents an attractive drug target. Three different approaches were used to identify inhibitors of ClpC1 function.

Approach 1.

A screening of the library of ATP analogs that inhibit protein kinases (Nathanael Gray, HMS) was used to identify inhibitors of ATPase activity of ClpC1. Two hits have been identified that inhibit ClpC1 activity at ~25-50 uM range.

Approach 2.

Figure 17:
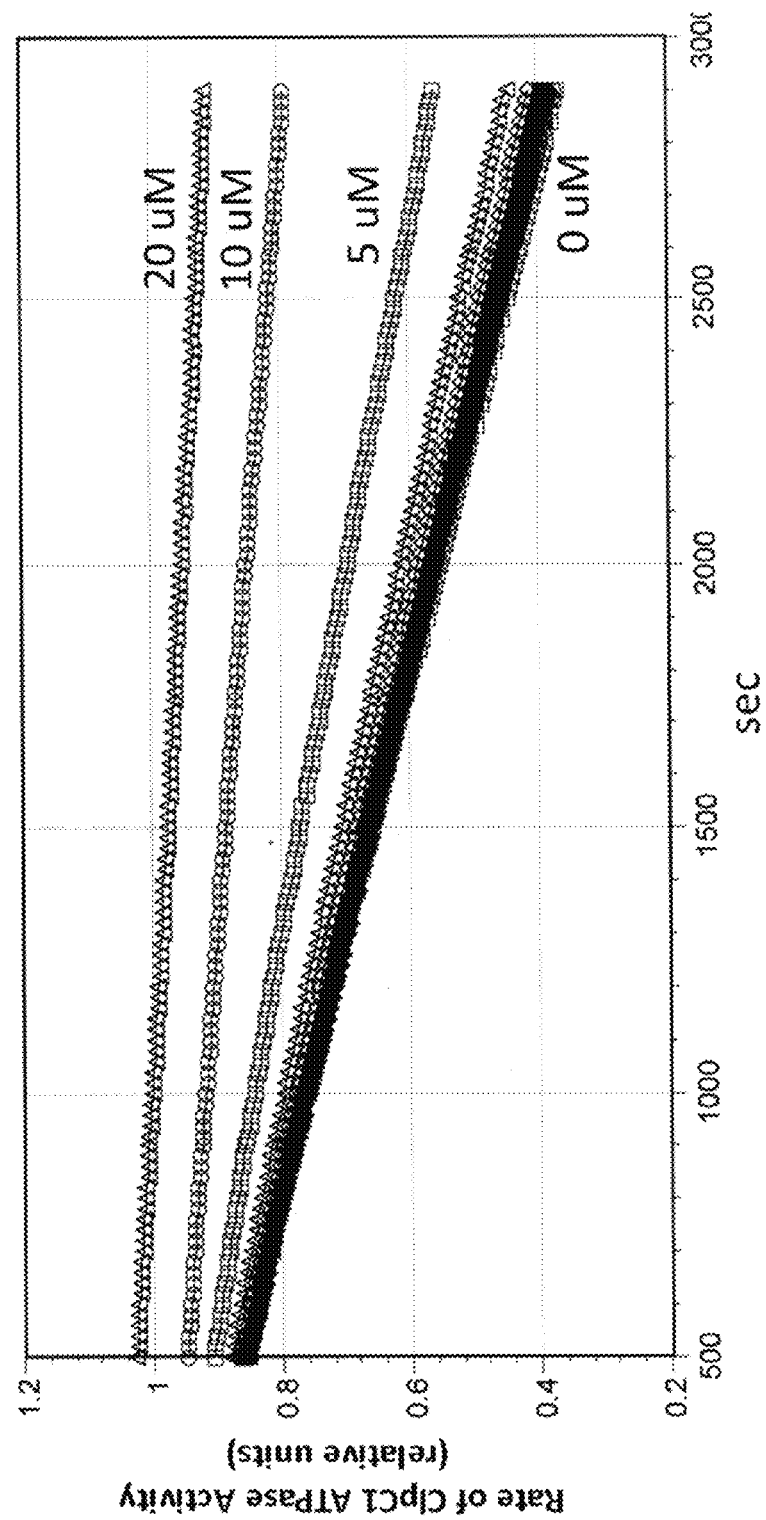
FIG. 17 depicts a graph demonstrating that p97 inhibitor (hexachlorophene) inhibits ClpC1 ATPase activity but not that of other bacterial ATPases or mammalian 26S proteasome.

A second approach involved testing a collection of inhibitors of the related AAA ATPase, p97, (collection of inhibitors identified by Deshaies R J, California Institute of Technology, is publically available), to identify inhibitors of ATPase activity of ClpC1. At least one promising hit has been identified (hexachlorophene, commercially available) that works at 5-10 mM concentration with Ki ~2-5 mM (FIG. 17).

Approach 3.

An antibiotic known as Novo23, a compound produced by *Kribbella jejuensis* K1356 and *Lentzea kentuckyensis* R0978, was tested. Novo23 exclusively kills Mycobacteria with MIC <1 ug/ml.

Figure 18:
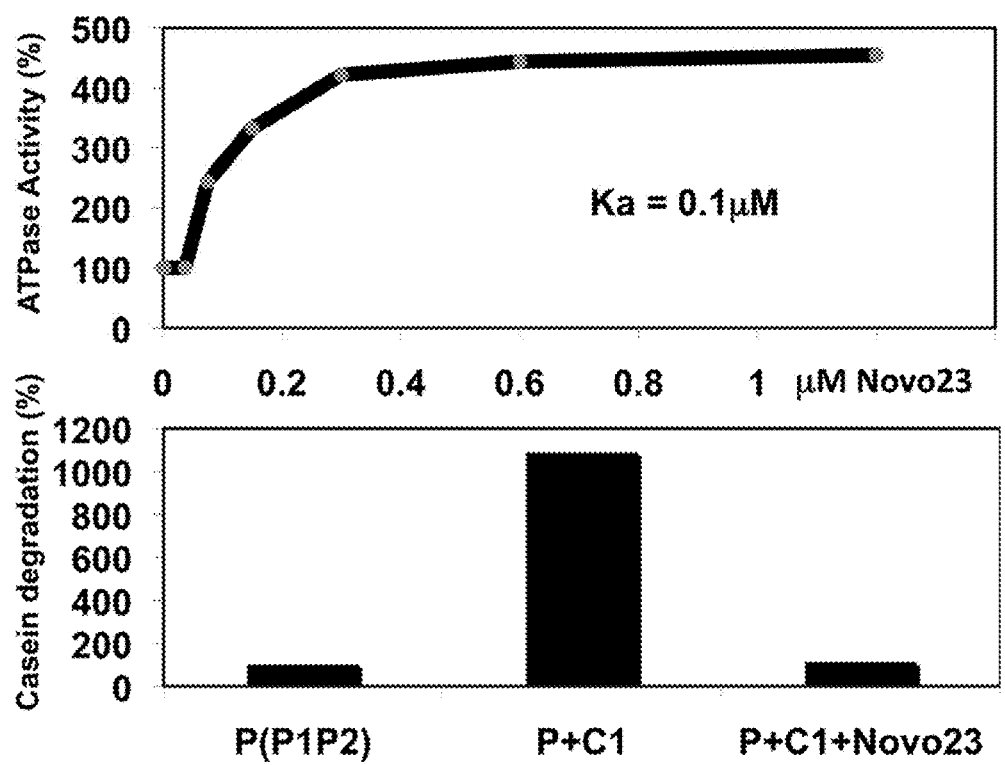
FIG. 18 depicts graphs demonstrating that Novo23 stimulates ATPase activity of ClpC1 but blocks the activation of casein degradation by ClpP1P2.

Using our in vitro ATPase assay and protein degradation assay (a novel system that includes ClpP1P2 protease and ClpC1 ATPase), it was verified that ClpC1/ClpP1P2 is a target for Novo23. Surprisingly, Novo23 did not inhibit ClpC1 ATPase activity, but instead stimulated it several fold (FIG. 18). Nevertheless, Novo23 completely blocked the activation of ClpP1P2-dependent protein degradation by ClpC1. Without wishing to be bound by theory, the data suggests that the Novo23-activated ClpC1 ATPase is unable to form the degradative complex with ClpP1P2. Such dissociation of the protease and ATPase functions is a novel and unique mechanism of inhibition of proteolysis.

Materials and Methods.

ATPase activity of ClpC1 was measured in the buffer containing 50 mM TrisHCl pH 7.8, 50 mM KCl, 10% glycerol, 1 mM DTT, 2 mM ATP, 8 mM $MgCl_2$. The amount of generated orthophosphate was measured colorimetrically by Malachite Green method. Alternatively, ATPase activity was measured continuously by PK/LDH method.

Determination of Enzymatic Activities.

Degradation of FITC-casein by ClpP1 (2.5 µg), ClpP2 (2.9 µg), or ClpP1P2 (2.7 µg) and ClpC1 (5-16 µg) was measured at 37° in 96 wells plate using Plate Reader SpectraMax M5 (Molecular Devices, USA). Wells contained FITC casein (2-5 µg), ClpP1P2, 0.5 mM Z-Leu-Leu-aldehyde or 5 mM Z-Leu-Leu in 80 µl of 50 mM phosphate buffer pH 7.6 with 5% glycerol and 100 mM KCl. FITC-casein was purified using PD-10 column, and its hydrolysis was continuously monitored at 518 nm (Ex at 492 nm). All assays were performed in triplicate and average results presented. Deviations in the measurements of FITC-casein was less than 10%.

TABLE 7

P3P2 sequences for 10 best substrates containing Met, Leu. Phe and Ala at P1 position. For P3: more than 75% cases (31 from 40) the efficient substrates have small amino acid residue particularly Pro (18 from 31). For P2: 70% cases (28 from 40) the efficient substrates have positive charged residue particularly Lys (14 from 28). Theoretical best efficient substrate must be N-acetyl-PKM-amc. Measuring the Kcat/Km of newly synthesized N-acetyl-PKM-amc indicates that it is the best substrate amongst efficient substrates (PWM, HKM, PFM and PRM) determined by library screening.

| P3P2P1 | P3 | P2 | P1 | Norm RFU |
|---|---|---|---|---|
| PWM | P | W | M | 2299 |
| HKM | H | K | M | 1957 |
| PFM | P | F | M | 1754 |
| PRM | P | R | M | 1712 |
| PKM | P | K | M | 1497 |
| POrM | P | Or | M | 1459 |
| ARM | A | R | M | 1294 |
| AKM | A | K | M | 1267 |
| AWM | A | W | M | 1230 |
| GKM | G | K | M | 1177 |
| PKL | P | K | L | 661 |
| WKL | W | K | L | 591 |
| WYL | W | Y | L | 478 |
| PLL | P | L | L | 385 |
| POrL | P | Or | L | 374 |
| PWL | P | W | L | 347 |
| WRL | W | R | L | 347 |
| PRL | P | R | L | 306 |
| YKL | Y | K | L | 276 |
| PSL | P | S | L | 272 |
| AKF | A | K | F | 489 |
| PKF | P | K | F | 454 |
| GWF | G | W | F | 440 |
| PRF | P | R | F | 423 |
| AWF | A | W | F | 320 |
| AYF | A | Y | F | 269 |
| PYF | P | Y | F | 265 |
| WKF | W | K | F | 238 |
| ARF | A | R | F | 235 |
| WYF | W | Y | F | 206 |
| PKA | P | K | A | 158 |
| PRA | P | R | A | 101 |
| VKA | V | K | A | 87 |
| ARA | A | R | A | 52 |
| POrA | P | Or | A | 45 |
| AKA | A | K | A | 43 |
| FKA | F | K | A | 24 |
| AOrA | A | Or | A | 21 |
| PWA | P | W | A | 18 |
| IRA | I | R | A | 11 |

TABLE 8

Kinetic constant Kcat/Km for Mtb ClpP1P2 and other bacterial ClpPs using individual acetylated tripeptide amc substrates. "Suc-LLVY-amc" disclosed as SEQ ID NO: 32.

| Substrate | Kcat/Km ($M^{-1}$ $sec^{-1}$) | | |
|---|---|---|---|
| Ac-(P3P2P1)-amc | M. tuberculosis | B. subtilis | E. coli |
| PKM | 1327 | 176 | 2632 |
| PKNle | 411 | 239 | 2464 |
| KM | 144 | 36 | 630 |
| PWM | 1155 | 520 | 4745 |
| WM | 612 | 268 | 4095 |
| ARM | 410 | 526 | 1553 |
| HKM | 169 | 6 | 695 |
| PKL | 199 | 234 | 2021 |
| PQL | 63 | 247 | 2886 |
| PYL | 32 | 598 | 3302 |
| PAL | 42 | 282 | 1804 |
| PKF | 320 | 132 | 634 |
| PAF | 68 | 97 | 605 |
| PKA | 40 | 76 | 812 |
| Z-GGL | 31 | 9 | 188 |
| Z-LLL | 0 | 0 | 46 |
| Z-LL | 0 | 2 | 58 |
| Suc-LY | 1 | 50 | 721 |
| Suc-LLVY | 2 | 1 | |

TABLE 9

Kinetic Constant Kcat/Km for Mtb ClpP1P2 and human proteasome using individual N-protected tripeptide amc substrates. "Suc-LLVY-amc" disclosed as SEQ ID NO: 32.

| Substrate Ac-(P3P2P1)-amc | Kcat/Km (M⁻¹ sec⁻¹) | |
|---|---|---|
| | *M. tuberculosis* ClpP1P2 | Human Proteasome (20S) |
| Chymotyptic like | | |
| PKM | 1327* | 5.6 |
| PWM | 1155 | 47.5 |
| ARM | 410 | 1.3 |
| HKM | 169 | 7.4 |
| PKL | 199 | 2.1 |
| PQL | 63 | 3.9 |
| PAL | 42 | 4.3 |
| PKF | 320 | 5.6 |
| PAF | 68 | 2.6 |
| PKA | 40 | 0.9 |
| Z-GGL | 31 | 765 |
| Suc-LY | 1 | 136 |
| Suc-LLVY | 2 | 2297* |
| Caspase like | | |
| Z-NLPnID | 14 | 180 |
| LWD | 2 | 125 |
| Trypsin-like | | |
| Z-LLR | 5 | 207 |
| Z-LRR | 4 | 46 |

*M. tuberculosis* ClpP1 amino acid sequence
SEQ ID NO: 01
MSQVTDMRSNSQGLSLTDSVYERLLSERIIFLGSEVNDEIANRLCAQILL
LAAEDASKDISLYINSPGGSISAGMAIYDTMVLAPCDIATYAMGMAASMG
EFLLAAGTKGKRYALPHARILMHQPLGGVTGSAADIAIQAEAFAVIKKEM
FRLNAEFTGQPIERIEADSDRDRWFTAAEALEYGFVDHIITRAHVNGEAQ

*M. tuberculosis* ClpP2 amino acid sequence
SEQ ID NO: 02
MNSQNSQIQPQARYILPSFIEHSSFGVKESNPYNKLFEERIIFLGVQVDD
ASANDIMAQLLVLESLDPDRDITMYINSPGGGFTSLMAIYDTMQYVRADI
QTVCLGQAASAAAVLLAAGTPGKRMALPNARVLIHQPSLSGVIQGQFSDL
EIQAAEIERMRTLMETTLARHTGKDAGVIRKDTDRDKILTAEEAKDYGII
DTVLEYRKLSAQTA Sequencing results of Mtb ClpP1 band
SEQ ID NO: 03
VSQVTDMRSNSQGLSLTDSVYERLLSERIIFLGSEVNDEIANRLCAQILL
LAAEDASKDISLYINSPGGSISAGMAIYDTMVLAPCDIATYAMGMAASMG
EFLLAAGTKGKRYALPHARILMHQPLGGVTGSAADIAIQAEQFAVIKKEM
FRLNAEFTGQPIERIEADSDRDRWFTAAEALEYGFVDHIITRAHVNGEAQ Sequencing results of Msm ClpP1 band
SEQ ID NO: 04
VYQDVVESRYPVVTDMRGTGQGLNLVDSVYERLLAERIIFLGSQVDDDIA
NRLCAQILLLSAEDPTKDIHLYINSPGGSISAGMAIYDTMVLAPCDIATY
AMGMAASMGEFLLAAGTKGKRYALPHARILMHQPLGGVTGSAADIAIQAE
QFAVIKKEMFRLNAEFTGQPIERIEADSDRDRWFTAQEALEYGFVDHIIT
SASVNGEGPGAGLDK Sequencing results of Mtb ClpP2 band
SEQ ID NO: 05
VNSQNSQIQPQARYILPSFIEHSSFGVKESNPYNKLFEERIIFLGVQVDD
ASANDIMAQLLVLESLDPDRDITMYINSPGGGFTSLMAIYDTMQYVRADI
QTVCLGQAASAAAVLLAAGTPGKRMALPNARVLIHQPSLSGVIQGQFSDL
EIQAAEIERMRTLMETTLARHTGKDAGVIRKDTDRDKILTAEEAKDYGII
DTVLEYRKLSAQTA Sequencing results of Msm ClpP2 band
SEQ ID NO: 06
MSNIHPSLDARLQPQARYILPSFIEHSSFGVKESNPYNKLFEERIIFLGV
QVDDASANDIMAQLLVLESLDPDRDITMYINSPGGSFTSLMAIYDTMQYV
RADIQTVCLGQAASAAAVLLAAGTPGKRLALPNARVLIHQPALSGVIQGQ
FSDLEIQAAEIERMRTLMETTLARHTGKDPAQIRKDTDRDKILTAEEEAKE
YGIIDTVLQYRKLSAQTS Amino acid sequence of *M. tuberculosis* ClpC1
SEQ ID NO: 37
mferftdrar rvvvlaqeea rmlnhnyigt ehillglihe
gegvaaksle slgislegvr sqveeiigqg qqapsghipf
tprakkvlel slrealqlgh nyigtehill gliregegva
aqvlvklgae ltrvrqqviq llsgyqgkea aeeagtggrgg
esgspstslv ldqfgrnlta aamegkldpv igrekeierv
mqvlsrrtkn npvligepgv gktavvegla qaivhgevpe
tlkdkqlytl dlgslvagsr yrgdfeerlk kvlkeintrg
diilfidelh tlvgagaaeg aidaasilkp klargelqti
gattldeyrk yiekdaaler rfqpvqvgep tvehtieilk
glrdryeahh rvsitdaamv aaatladryi ndrflpdkai
dlideagarm rirrmtappd lrefdekiae arrekesaid
agdfekaasl rdrektlvaq raerekqwrs gdldvvaevd
deqiaevlgn wtgipvfklt eaettrllrm eeelhkriig
qedavkavsk airrtraglk dpkrpsgsfi fagpsgvgkt
elskalanfl fgdddaliqi dmgefhdrft asrlfgappg
yvgyeeggql tekvrrkpfs vvlfdeieka hqeiynsllq
vledgrltdg qgrtvdfknt vliftsnlgt sdiskpvglg
fskgggendy ermkqkvnde lkkhfrpefl nriddiivfh
qltreeiirm vdlmisrvag qlkskdmalv ltdaakalla
krgfdpvlga rplrrtiqre iedqlsekil feevgpgqvv
tvdvdnwdge gpgedavftf tgtrkppaep dlakagahsa
ggpepaar

What is claimed herein is:

1. A method of treating a *Mycobacterium tuberculosis* infection comprising administering, to a subject having a *Mycobacterium tuberculosis* infection, a composition comprising at least one of:
   a) Novo23; or
   b) a ClpP1 polypeptide comprising the amino acid sequence of SEQ ID NO: 1, wherein the amino acid sequence comprises a Ser98Ala or His123Ala mutation.

2. The method of claim 1, further comprising administering to a subject a composition comprising a further antibiotic.

3. The method of claim 2, wherein the antibiotic is an aminoglycoside.

* * * * *

UNITED STATES PATENT AND TRADEMARK OFFICE
CERTIFICATE OF CORRECTION

PATENT NO. : 9,925,251 B2  
APPLICATION NO. : 14/352440  
DATED : March 27, 2018  
INVENTOR(S) : Akopian et al.

Page 1 of 1

It is certified that error appears in the above-identified patent and that said Letters Patent is hereby corrected as shown below:

In the Specification

At Column 1, under the heading GOVERNMENT SUPPORT:
"This invention was made in part with U.S. Government support from grants GM51923-13 and R21NS067598 from the National Institutes of Health and grant 5RO1A71881-02 from the National Institute of Allergy and Infectious Diseases. The U.S. Government has certain rights in the invention."

Should be replaced with:
—This invention was made with government support under GM051923, AI071881, and NS067598 awarded by the National Institutes of Health. The government has certain rights in the invention.—

Signed and Sealed this  
Twelfth Day of May, 2020

Andrei Iancu  
*Director of the United States Patent and Trademark Office*